(12) United States Patent
Kularatne et al.

(10) Patent No.: US 11,964,965 B2
(45) Date of Patent: Apr. 23, 2024

(54) METHODS OF MANUFACTURE AND SYNTHESIS OF FLUORESCENT DYE COMPOUNDS AND USES THEREOF

(71) Applicant: On Target Laboratories, LLC, West Lafayette, IN (US)

(72) Inventors: Sumith A. Kularatne, West Lafayette, IN (US); Pravin Gagare, West Lafayette, IN (US)

(73) Assignee: On Target Laboratories, LLC, West Lafayette, IN (US)

( * ) Notice: Subject to any disclaimer, the term of this patent is extended or adjusted under 35 U.S.C. 154(b) by 0 days.

(21) Appl. No.: 16/879,569

(22) Filed: May 20, 2020

(65) Prior Publication Data

US 2021/0347766 A1 Nov. 11, 2021

Related U.S. Application Data

(60) Provisional application No. 63/022,247, filed on May 8, 2020.

(51) Int. Cl.
*C07D 405/14* (2006.01)
*C07D 403/08* (2006.01)
*C07D 487/04* (2006.01)

(52) U.S. Cl.
CPC ......... *C07D 405/14* (2013.01); *C07D 403/08* (2013.01); *C07D 487/04* (2013.01)

(58) Field of Classification Search
CPC ... C07D 405/14; C07D 487/04; C07D 403/08
USPC ....................................................... 514/249
See application file for complete search history.

(56) References Cited

U.S. PATENT DOCUMENTS

| 10,456,482 B2 | 10/2019 | Kularatne et al. |
| 2010/0267937 A1 | 10/2010 | West et al. |
| 2015/0011731 A1 | 1/2015 | Blanchard et al. |
| 2017/0281801 A1 | 10/2017 | Kularatne et al. |

FOREIGN PATENT DOCUMENTS

| CN | 101440282 A * | 5/2009 | |
| EP | 430244 A1 * | 6/1991 | ......... C09B 23/0008 |
| EP | 580145 A2 * | 1/1994 | ............ G03C 1/832 |
| WO | WO-2010091243 A1 * | 8/2010 | ............... A61B 6/00 |
| WO | WO-2015064786 A1 * | 5/2015 | ......... A61K 49/0032 |

OTHER PUBLICATIONS

PCT, International Search Report regarding PCT Application No. PCT/US2020/52382, dated Dec. 18, 2020, 8 pages.
PCT, International Preliminary Report on Patentability regarding PCT Application No. PCT/US2020/52382, dated Nov. 17, 2022, 6 pages.

* cited by examiner

*Primary Examiner* — Kahsay Habte
(74) *Attorney, Agent, or Firm* — McAndrews, Held & Malloy, Ltd.

(57) ABSTRACT

The present disclosure relates to synthesizing and utilizing fluorescent dye compounds or pharmaceutically acceptable salts thereof. Conjugation of amino acid groups to the fluorescent dyes increase specificity and detection of the compound. Methods of manufacture and synthesis of the compounds for use thereof in diagnostic imaging are contemplated.

6 Claims, 14 Drawing Sheets

METHODS OF MANUFACTURE AND SYNTHESIS OF FLUORESCENT DYE COMPOUNDS AND USES THEREOF

RELATED APPLICATIONS

The present patent application is related to and claims the priority benefit of U.S. Provisional Patent Application Ser. No. 63/022,247, filed May 8, 2020, the content of which is hereby incorporated by reference in its entirety into this disclosure.

FIELD OF THE INVENTION

The present disclosure is in the area of diagnostics. This disclosure provides methods of synthesizing and utilizing fluorescent dye compounds or pharmaceutically acceptable salts thereof. Conjugation of amino acid groups to the fluorescent dyes increases specificity and detection of the compound. Methods of manufacture and synthesis of the compounds for use thereof in diagnostic imaging are contemplated.

BACKGROUND OF THE INVENTION

Surgical removal of malignant disease constitutes one of the most common and effective therapeutic for primary treatment for cancer. Resection of all detectable malignant lesions results in no detectable return of the disease in approximately 50% of all cancer patients and may extend life expectancy or reduce morbidity for patients in whom recurrence of the cancer is seen. Not surprisingly, surgical methods for achieving more quantitative cytoreduction are now receiving greater scrutiny.

Given the importance of total resection of the malignant lesions, it is beneficial to ensure that the malignant lesions are accurately and completely identified. Three methods currently accomplish the identification of malignant tissue during surgery. First, many tumor masses and nodules can be visually detected based on abnormal color, texture, and/or morphology. Thus, a tumor mass may exhibit variegated color, appear asymmetric with an irregular border, or protrude from the contours of the healthy organ. A malignant mass may also be recognized tactilely due to differences in plasticity, elasticity, or solidity from adjacent healthy tissues. Finally, a few cancer foci can be located intraoperatively using fluorescent dyes that flow passively from the primary tumor into draining lymph nodes. In this latter methodology, fluorescent (sentinel) lymph nodes can be visually identified, resected, and examined to determine whether cancer cells have metastasized to these lymph nodes.

While non-targeted fluorescent dyes have been shown to passively accumulate in some tumors, the resulting tumor-to-background ratios are often poor and the boundaries between malignant and healthy tissues can be difficult to define. Although ligand targeted fluorescence dyes (e.g., EC17: Folate-EDA-FITC) have been used for imaging a tissue, those dyes have been ineffective as they would not penetrate deep tissue and hence only identified the specific cells on the surface of a tissue rather than deeper within the tissue sample. In addition, it has been shown that the excitation and emission spectra of these previous fluorescence dyes were such that it produced significant background noise such that the targeted tissue was not easily detected. In addition, as discussed in the background above, fluorescein-based dyes have the disadvantages of low shelf-life stability. EC17 easily decomposes as a result of the instability of the thiourea bridge in that compound. In addition, EC17 uses fluorescein, which has the drawback of a relatively high level of nonspecific background noise from collagen in the tissues surrounding the imaging site. Moreover, the absorption of visible light by biological chromophores, in particular hemoglobin, further limits the usefulness of dyes that incorporate fluorescein. This means that conventional dyes cannot readily detect tumors that may be buried deeper than a few millimeters in the tissue. Furthermore, fluorescence from fluorescein is quenched at low pH (below pH 5).

In order for a dye material to be useful in detecting and guiding surgery or providing other tissue imaging, it would be beneficial to overcome these drawbacks.

Thus, there remains a need for the synthesis and purification of a dye substance that can be used to specifically target diseased tissue and has increased stability and brightness for use in vivo for tissue imaging.

BRIEF SUMMARY OF THE INVENTION

One aspect of the present technology is a compound of the formula selected from the group consisting of:

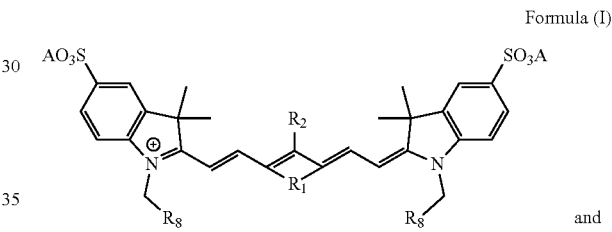

Formula (I)

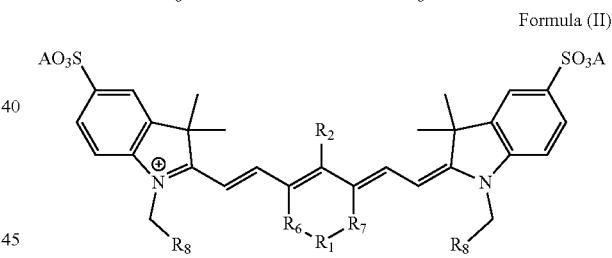

Formula (II)

wherein:

$R_1 = (CH_2)_n$ and $n = 0, 1, 2, 3, \ldots$ $R_2 =$ Halogen such as Cl, Br, I or X—$R_3$ $X = (CH_2)_m$, NH, O, S, Se and $m = 0, 1, 2, 3, \ldots$ $R_3 = [CH_2]_p CH(R_4)COOH$ or $C_6H_4$—$[CH_2]_p CH(R_4)COOH$ or $(CH_2)_p COOH$ or $(CH_2)_p NH_2$ and $p = 0, 1, 2, 3, \ldots$ $R_4 = H$, $NHR_5$ $R_5 = H$, alkyl group, amine protecting group, sugar $R_6$, $R_7 = CH_2$, NH, O, S, Se, or combination of them $R_8 = (CH_2)_q SO_3H$ and $q = 0, 1, 2, 3, \ldots$ A = counter cation.

In another aspect, the counter cation is selected from the group consisting of sodium, potassium, calcium, magnesium, lithium, cholinate, lysinium, ammonium, or hydrogen.

Another aspect of the present technology is a compound selected from the group consisting of

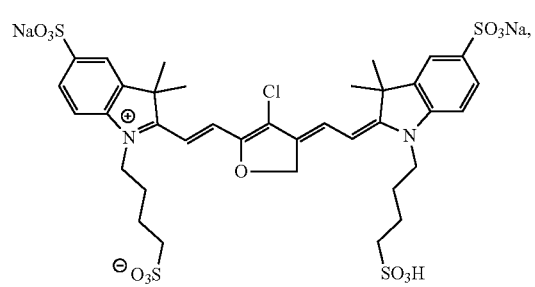
106
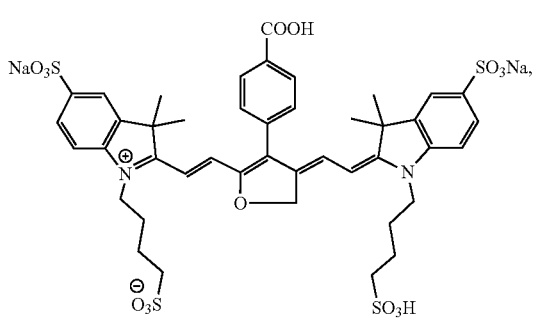
107
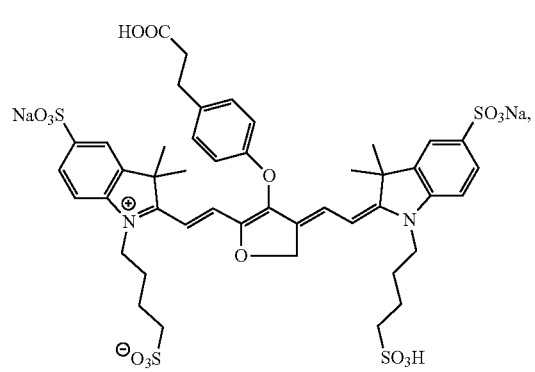
108
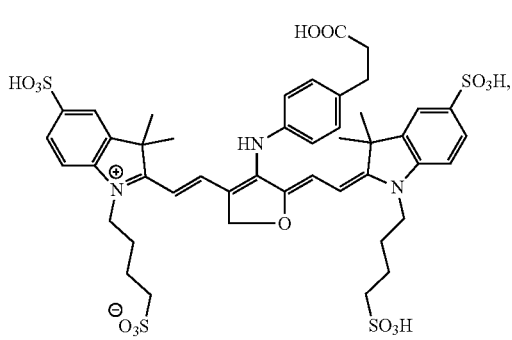
109
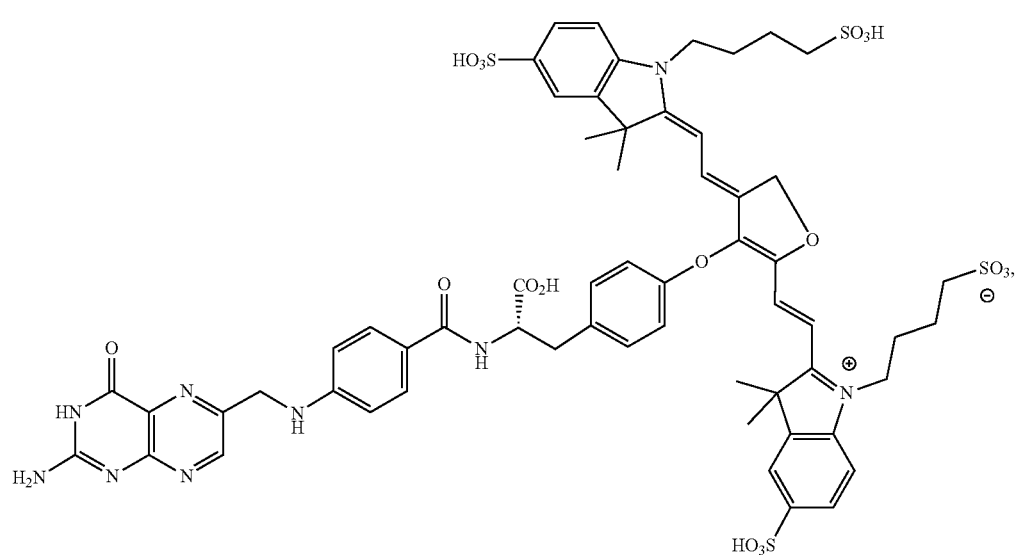
110
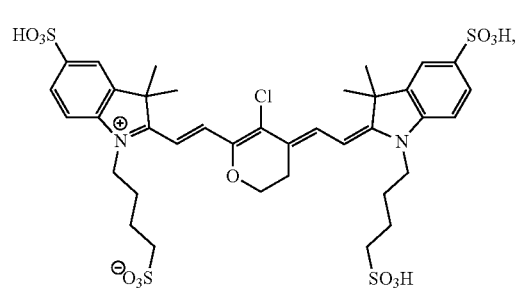
115
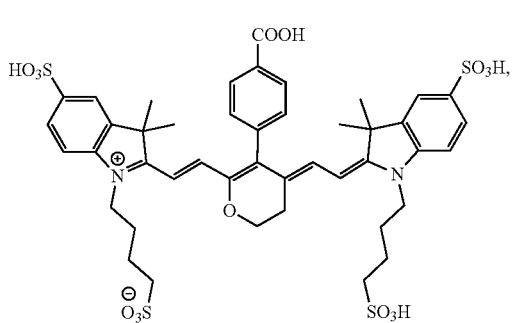
116

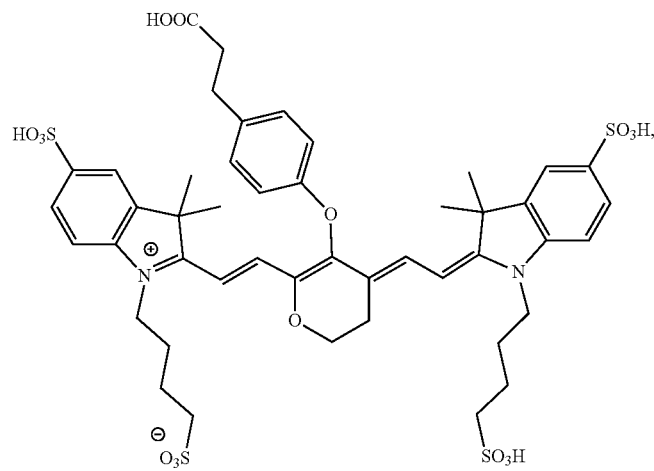
117
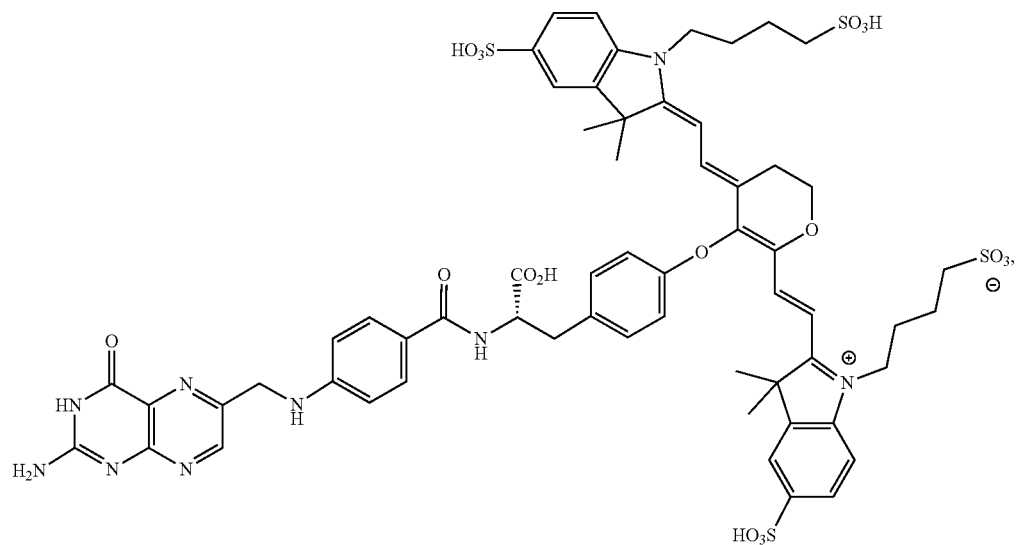
118
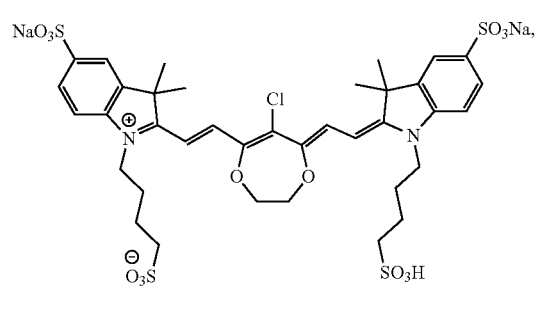
120
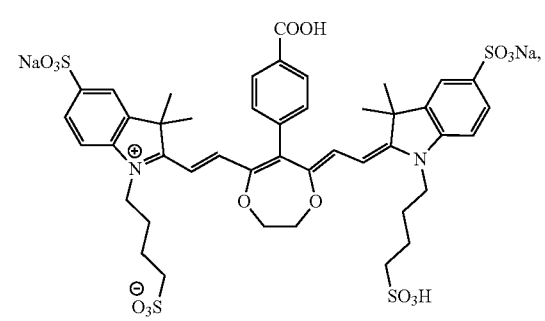
121

-continued
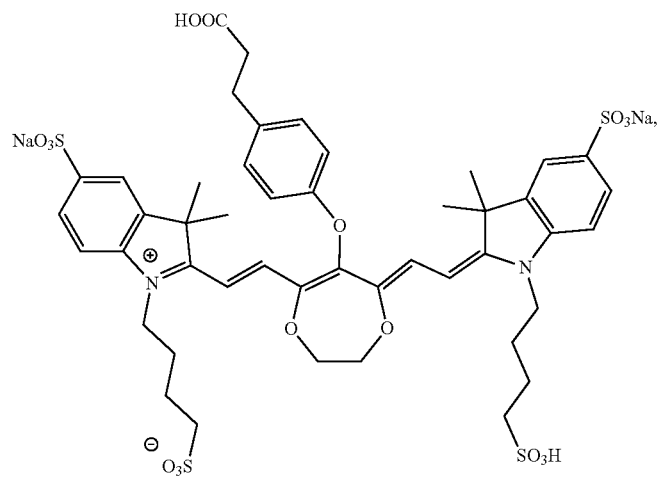
122
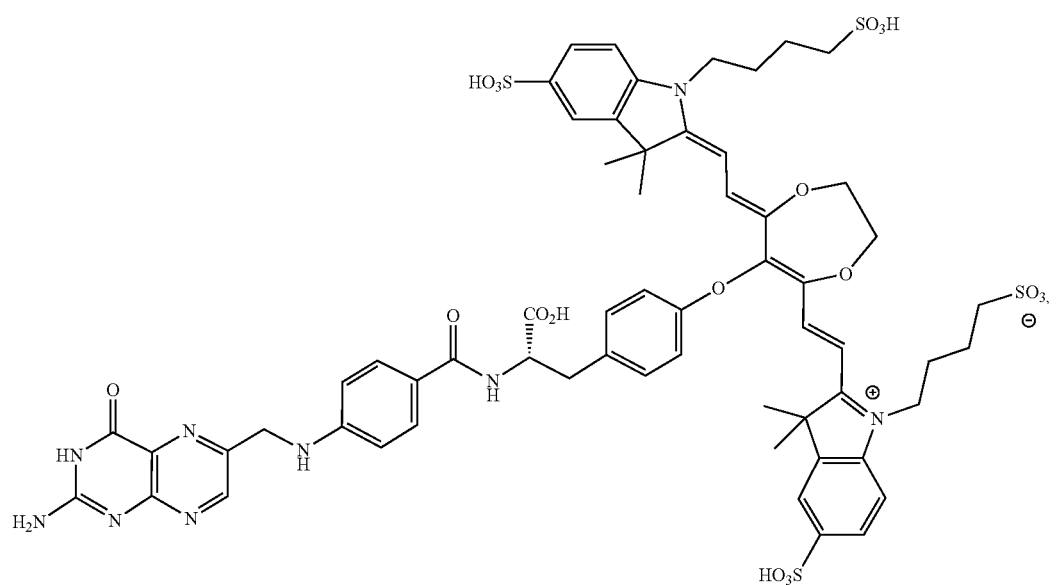
123
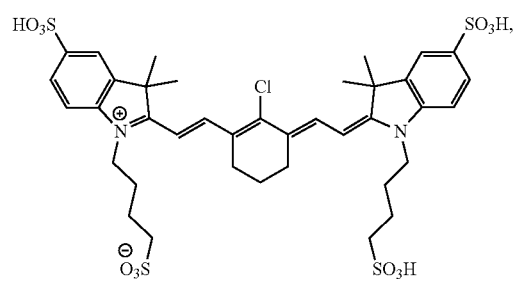
125
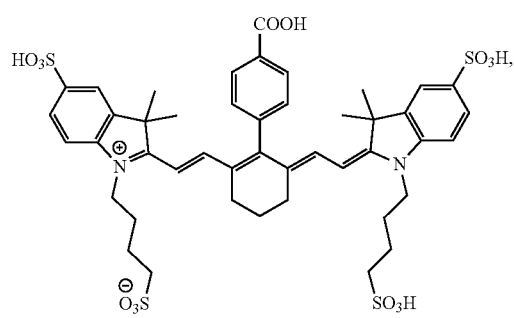
126

-continued
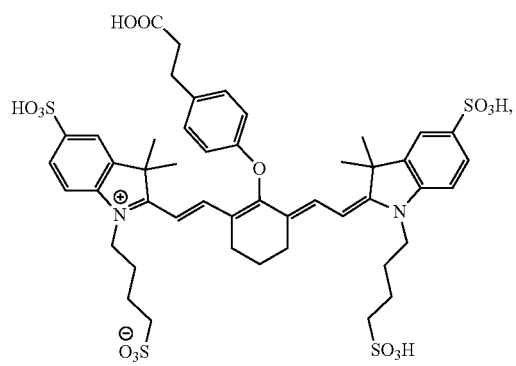
127
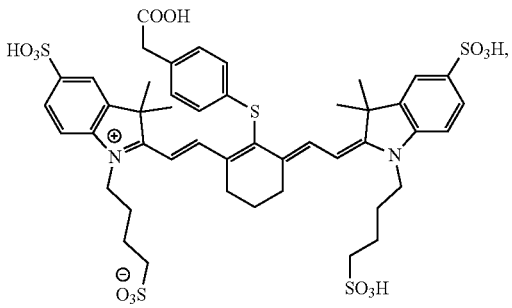
128
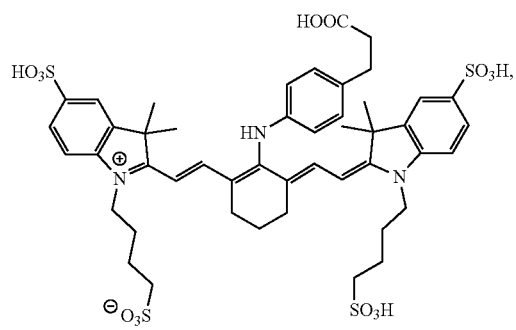
129
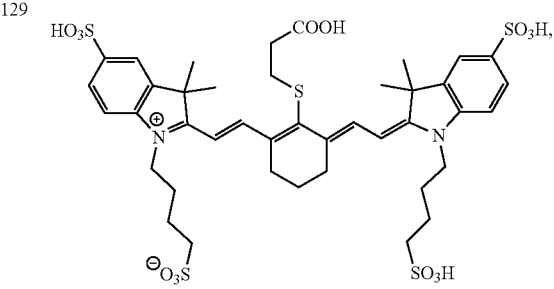
130
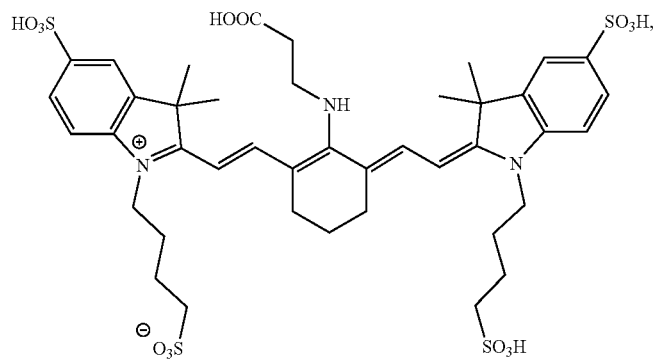
131
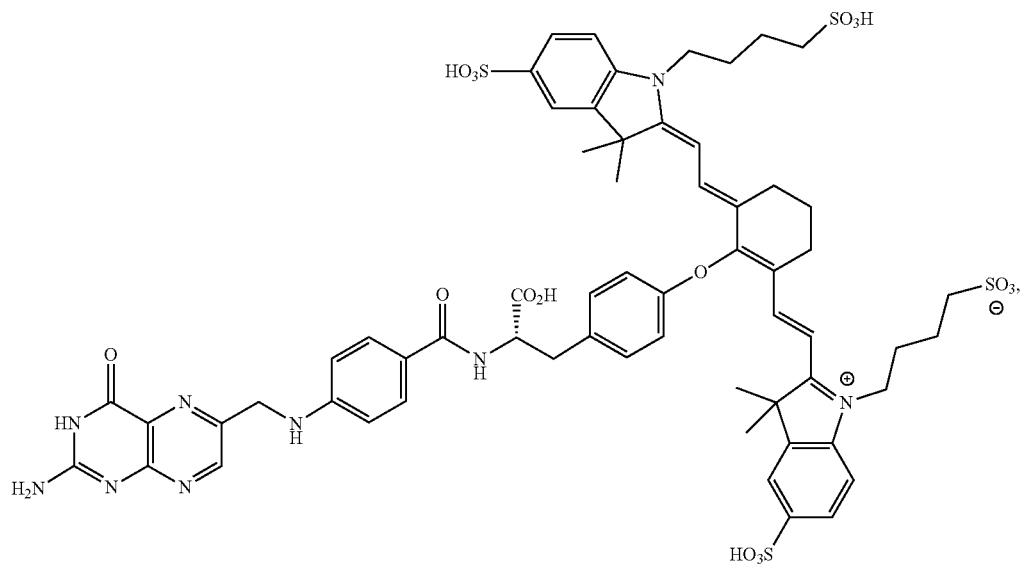
132

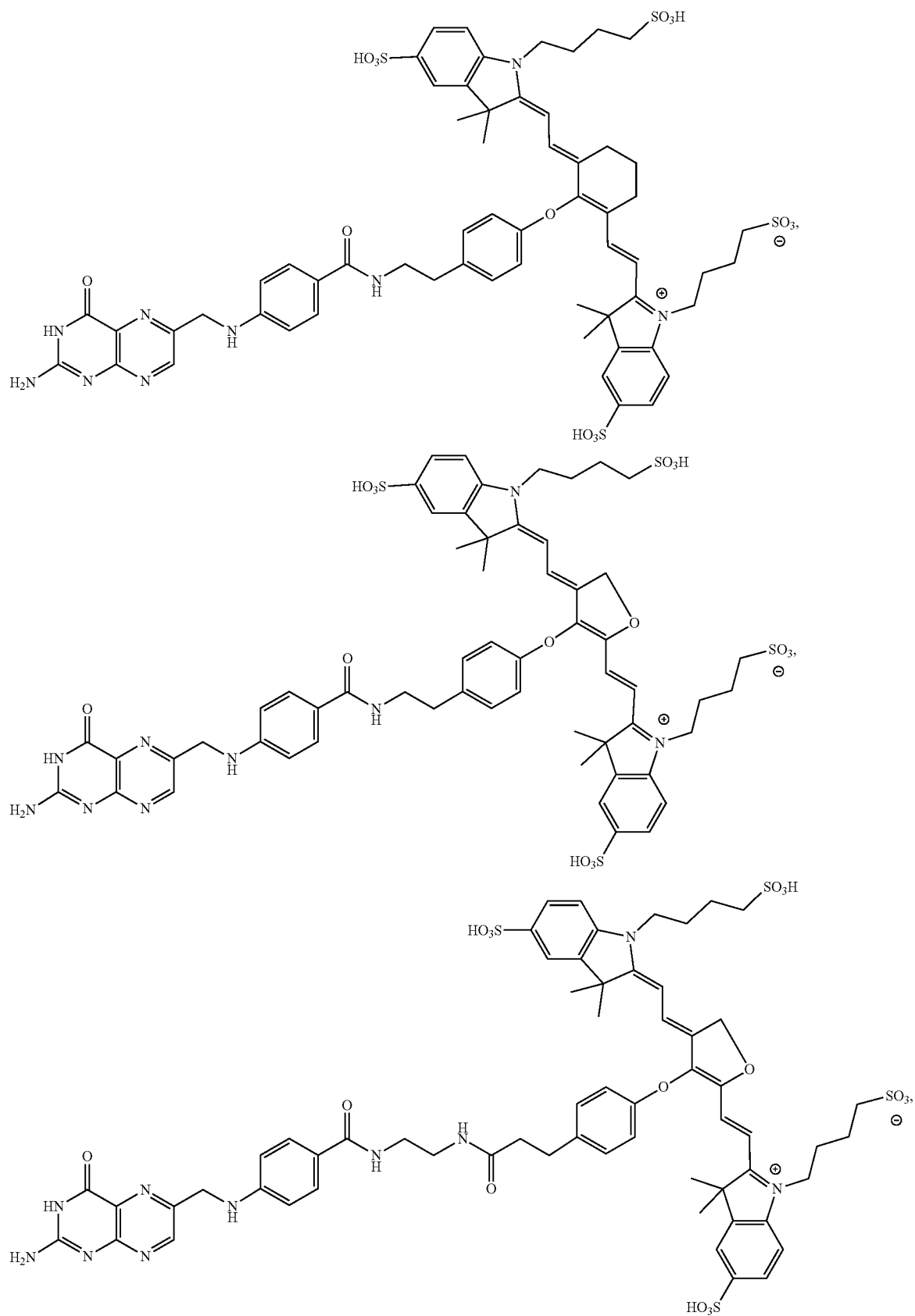

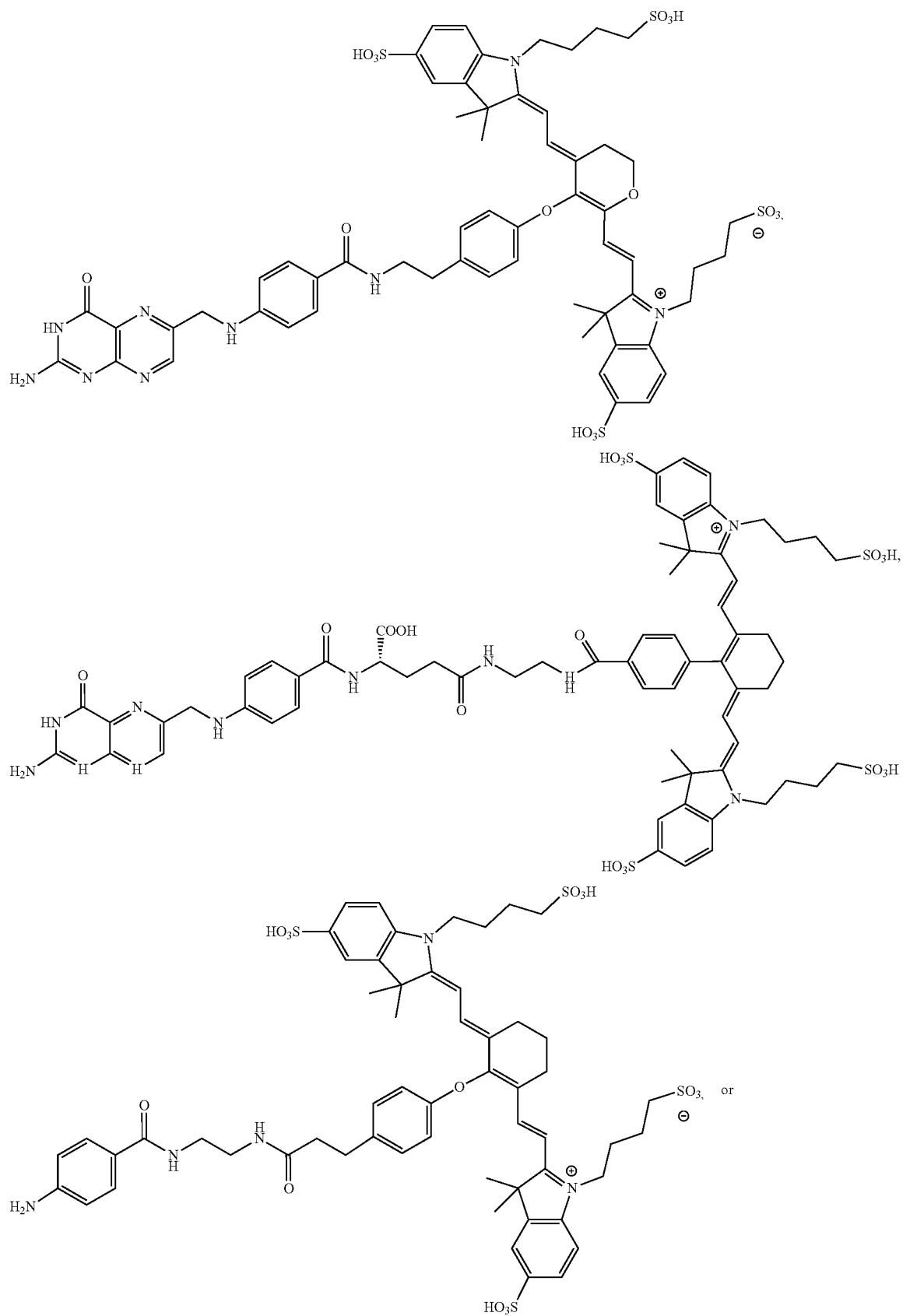

-continued

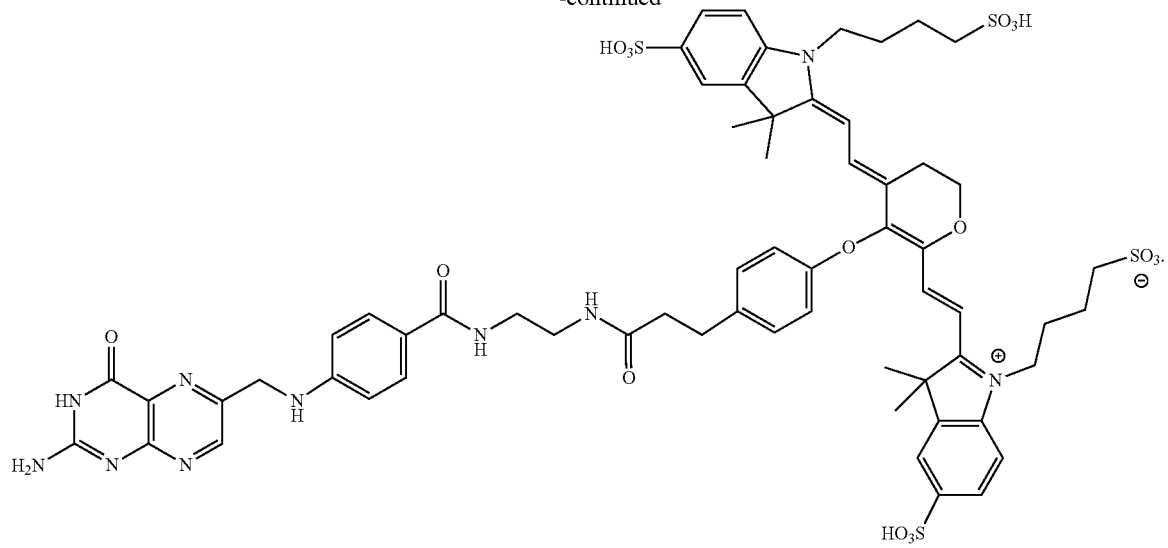

Another aspect of the present technology is a method for synthesizing a compound selected from the group Formula (I)

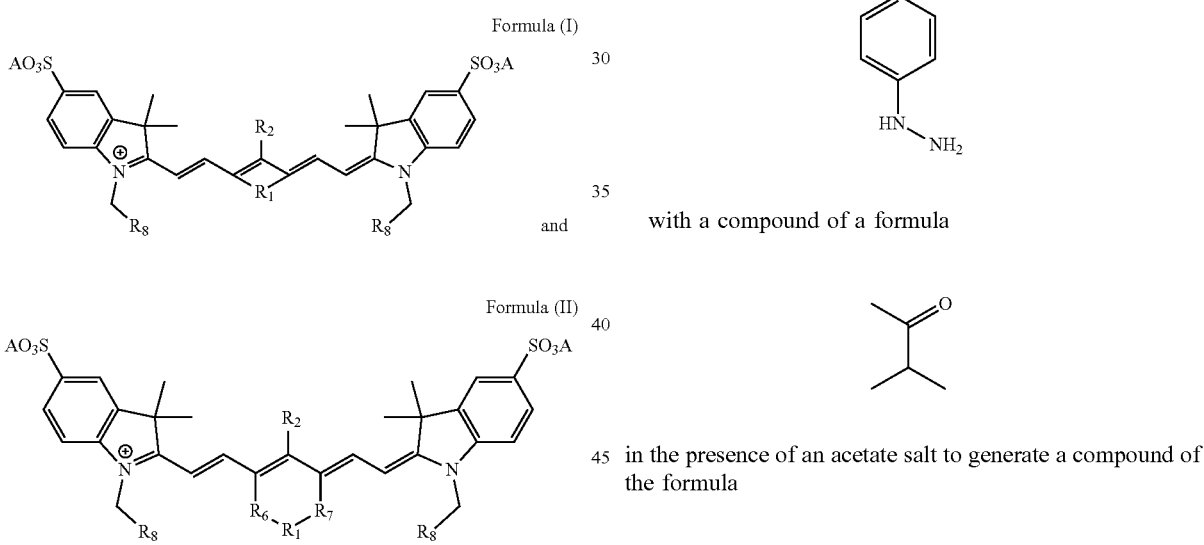

Formula (II)

wherein:
$R_1 = (CH_2)_n$ and $n = 0, 1, 2, 3, \ldots$
$R_2 =$ Halogen such as Cl, Br, I or X—$R_3$
$X = (CH_2)_m$, NH, O, S, Se and $m = 0, 1, 2, 3, \ldots$
$R_3 = [CH_2]_p CH(R_4)COOH$ or $C_6H_4$—$[CH_2]_p CH(R_4)COOH$ or $(CH_2)_p COOH$ or $(CH_2)_p NH_2$ and $p = 0, 1, 2, 3, \ldots$
$R_4 = H, NHR_5$
$R_5 = H$, alkyl group, amine protecting group, sugar
$R_6, R_7 = CH_2$, NH, O, S, Se, or combination of them
$R_8 = (CH_2)_q SO_3H$ and $q = 0, 1, 2, 3, \ldots$
$A =$ counter cation comprising the steps of
(a) reacting a compound of a formula with a compound of a formula

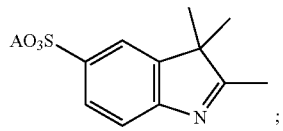

in the presence of an acetate salt to generate a compound of the formula (b) reacting the resulting compound with a compound of the formula

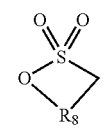

in the presence of non-polar solvent to generate a compound of the formula

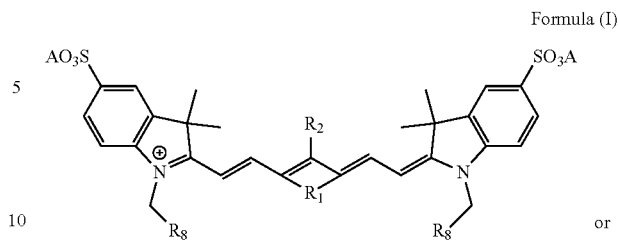

Formula (I)

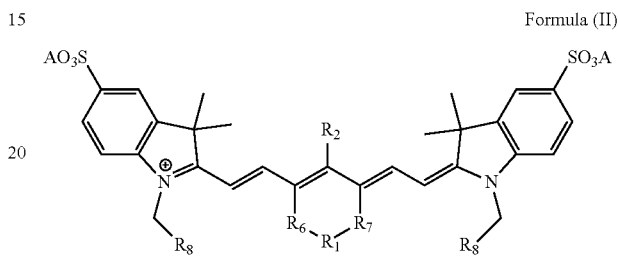

Formula (II)

(c) reacting a compound of the formula

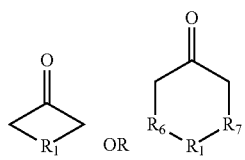

in the presence of an acetate salt, sultone, and a nonpolar solvent to generate a compound of the formula

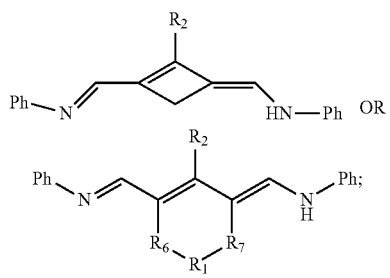

(d) reacting the compound of the formula

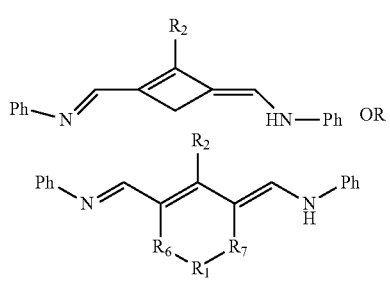

with a compound of the formula

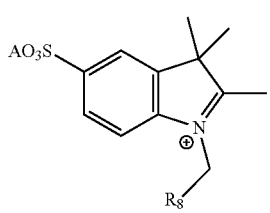

in the presence of an acetate salt to generate a compound of the formula

In one aspect, the method further comprises step (e) wherein the compound of the formula

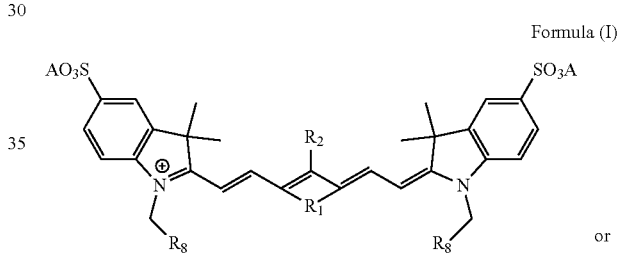

Formula (I)

or

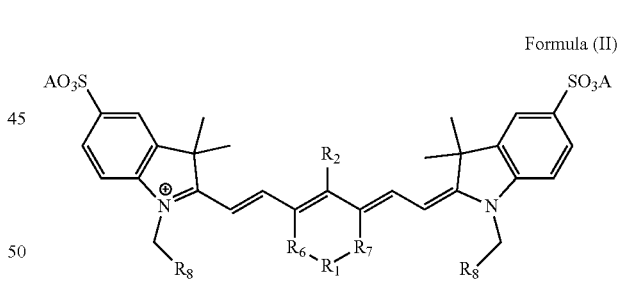

Formula (II)

is reacted with X—R in polar solvent, wherein X=OH, NH2, SH, or SeH to generate a compound of the formula

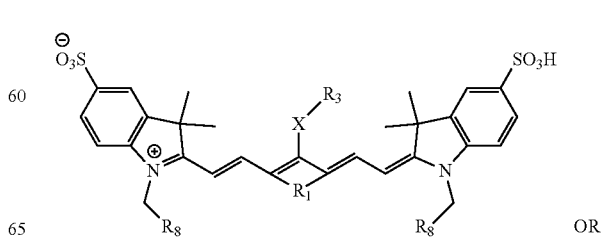

OR

-continued

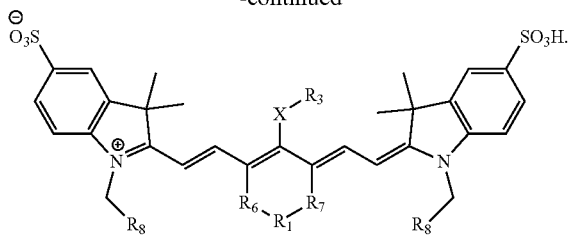

In another aspect, the method further comprises reacting the resulting compound of step (e) with a base and a compound of the formula Ligand-Linker-Z, wherein the Ligand is an antibody, small molecule, aptamer, protein, or peptide and wherein Z is COOH, NH2, OH, or SH.

In another aspect, the resulting compound in step (d) or step (e) is precipitated using a non-polar solvent or purified by chromatographic methods or crystallization method. In another aspect, the yield of the resulting compound in step (d) or step (e) is at least 60%, at least 65%, at least 70%, at least 75%, at least 80%, at least 85%. In yet another aspect, the purity of the resulting compound in step (d) or step (e) is at least 90%, at least 91%, at least 92%, at least 93%, at least 94%, at least 95%, at least 96%, at least 97%, at least 98%, at least 99%, at least 99.5%.

In another aspect, the non-polar solvent or polar solvent is an organic solvent.

In another aspect, the resulting compound is selected from the group consisting of:

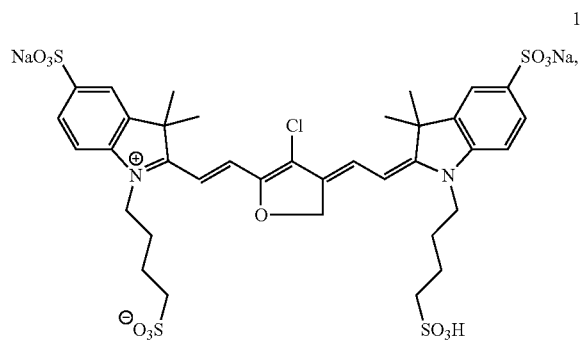

106

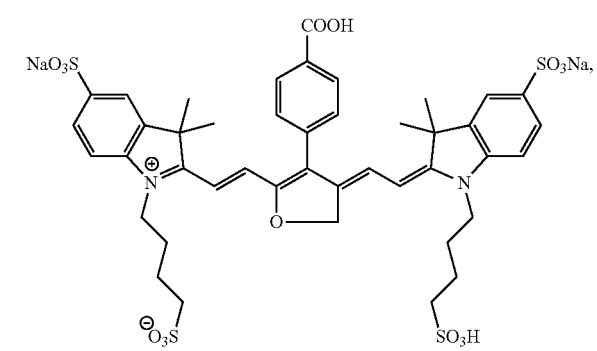

107

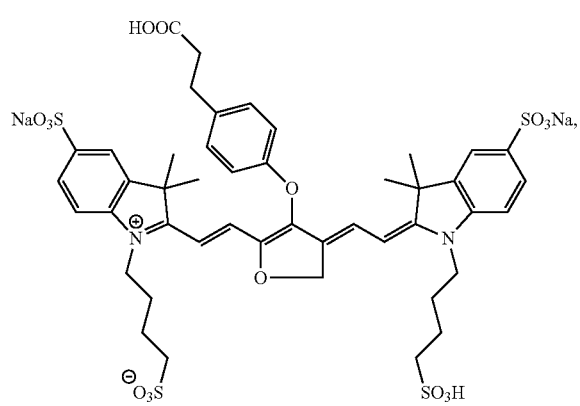

108

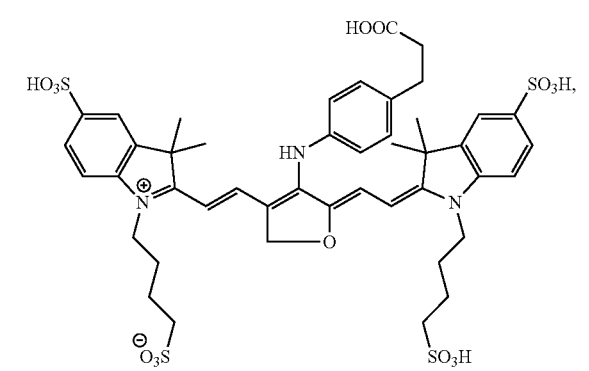

109

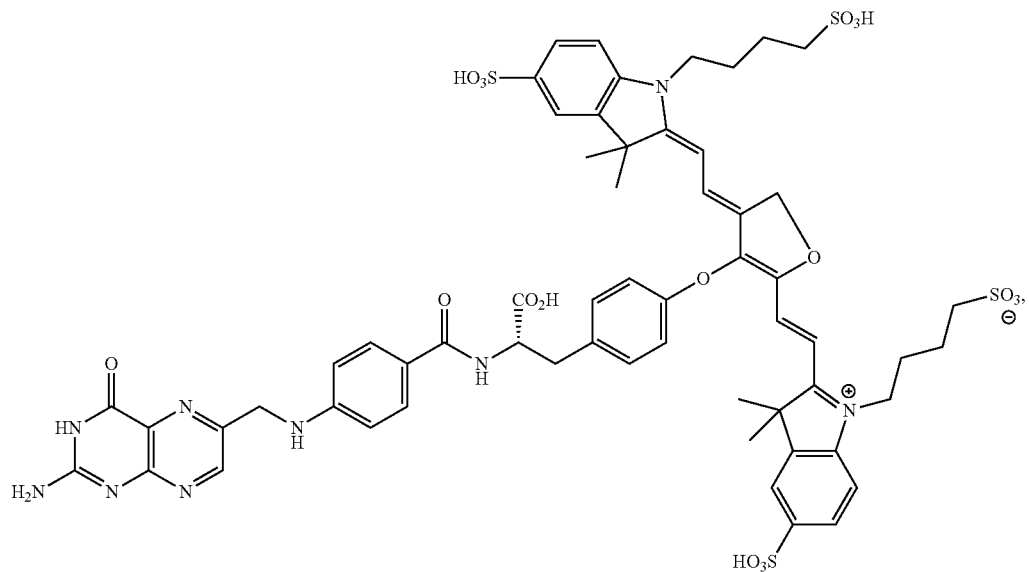
110
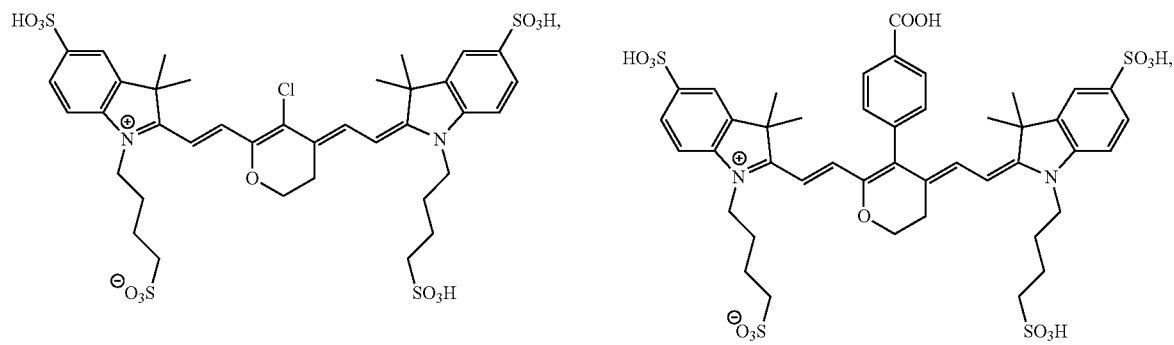
115 116
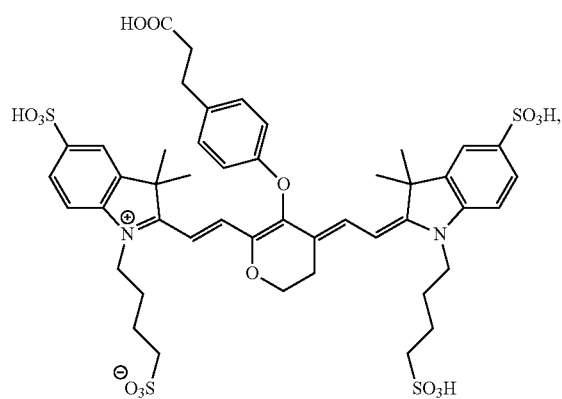
117

-continued
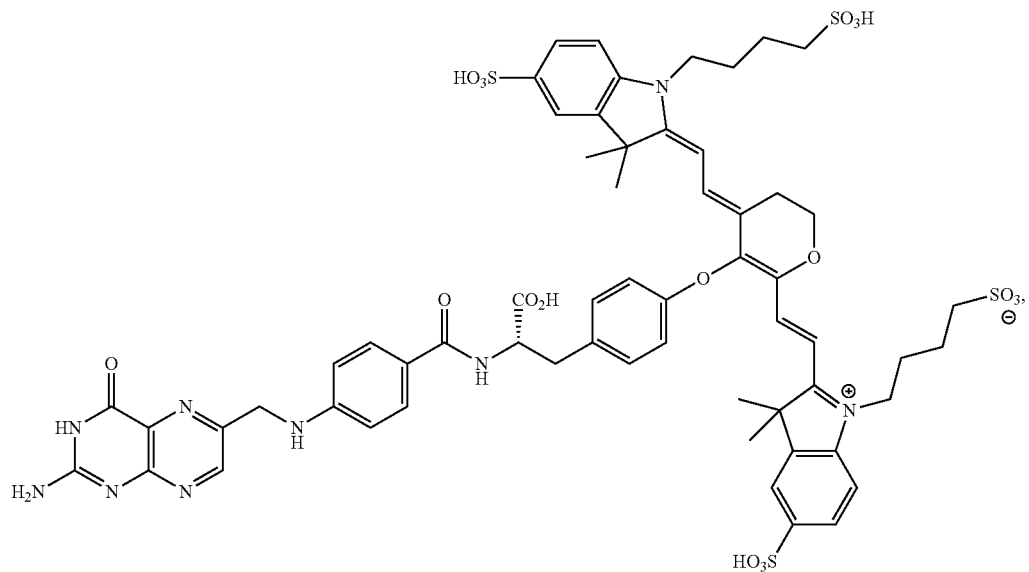
118
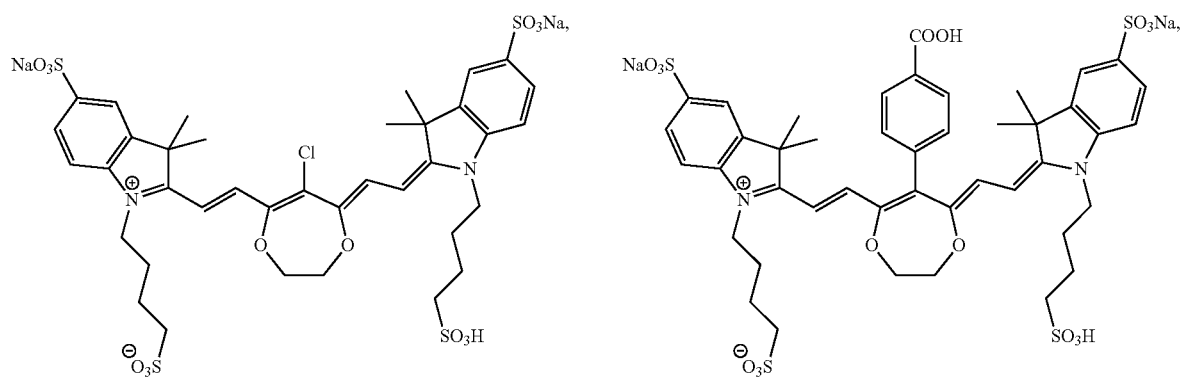
120    121
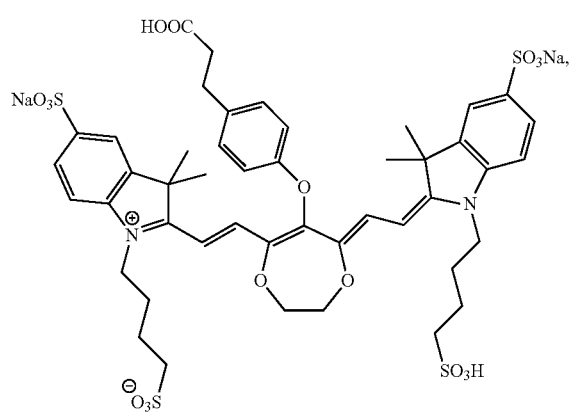
122

123
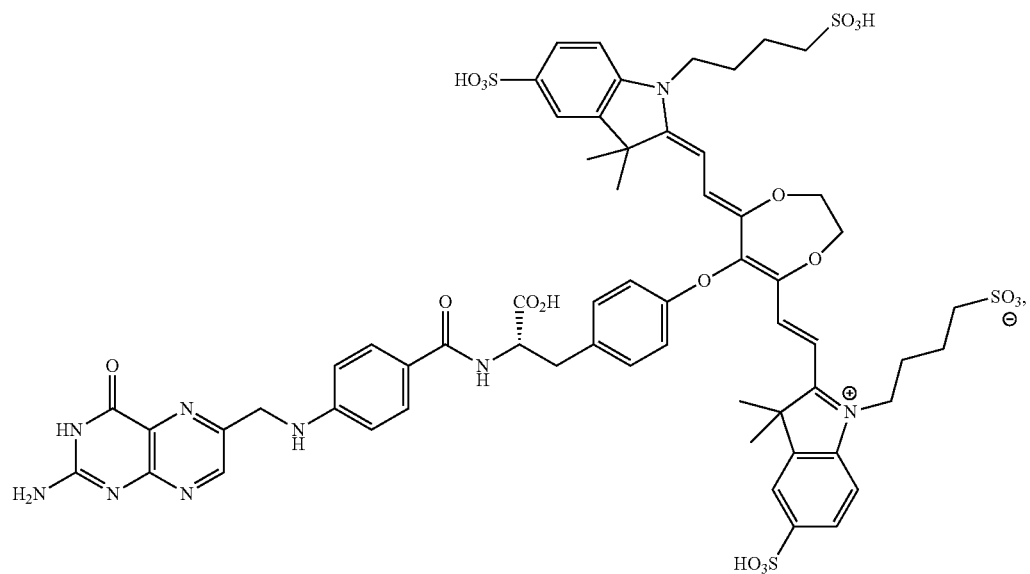
125
126
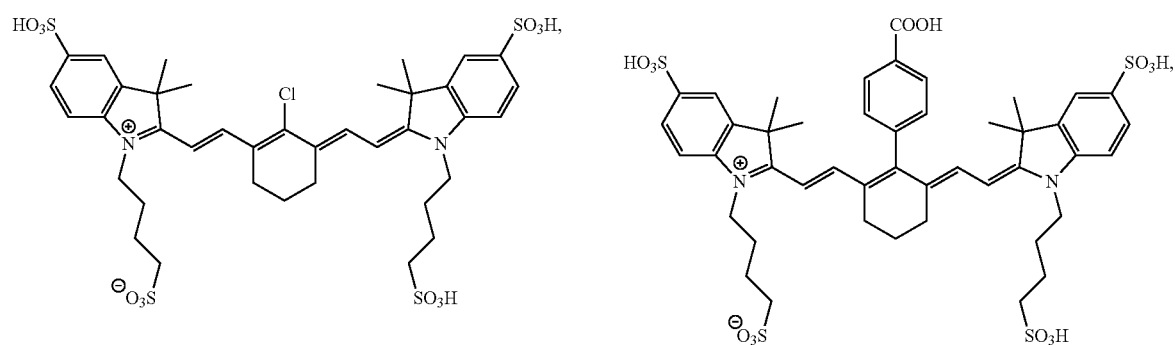
127
128
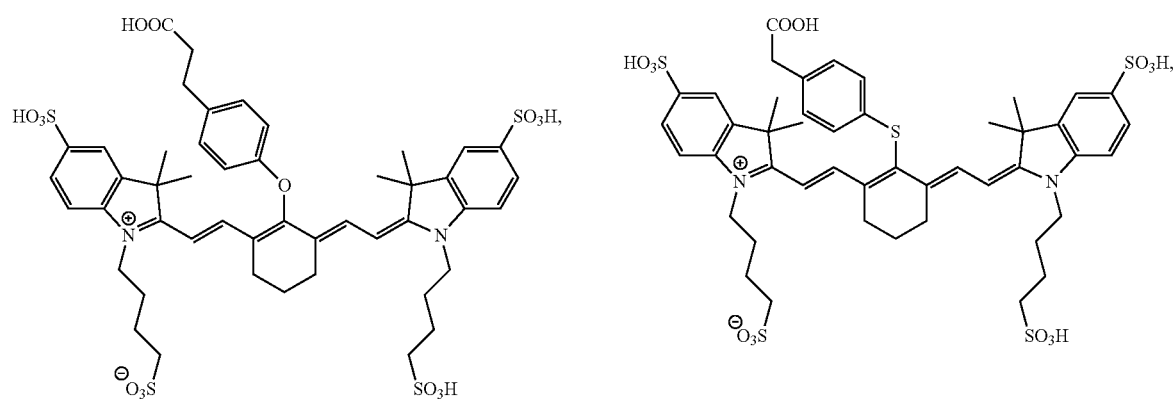

129
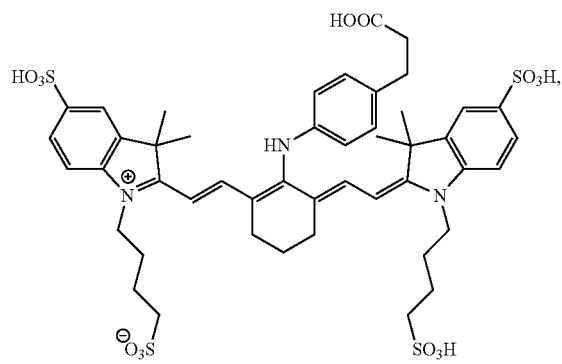
130
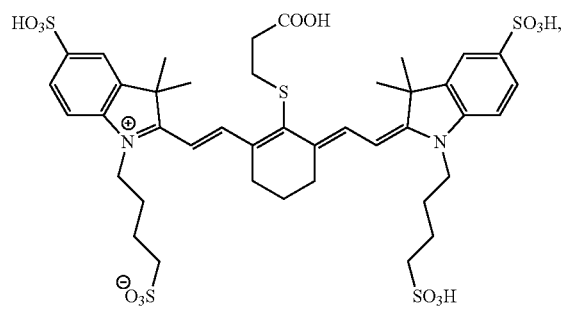
131
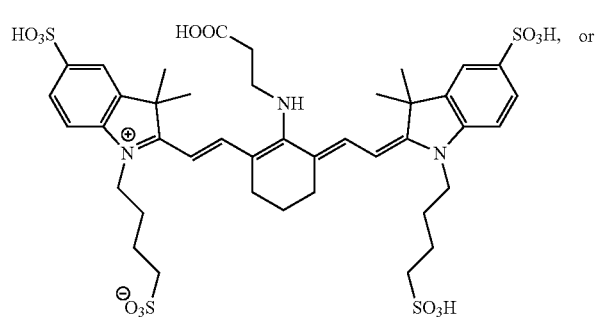
, or
132
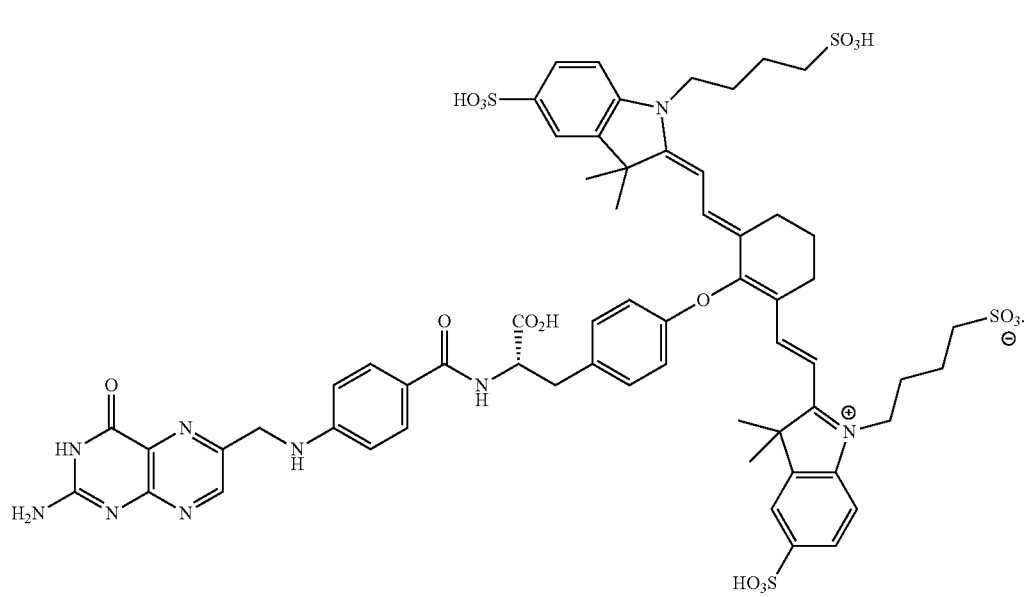

In another aspect, the resulting compound is selected from the group consisting of:
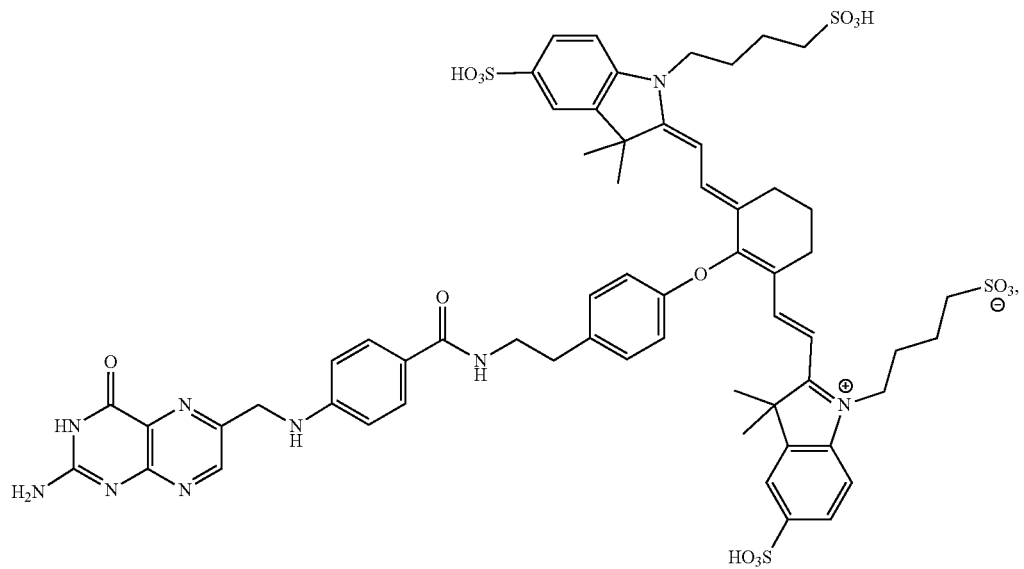
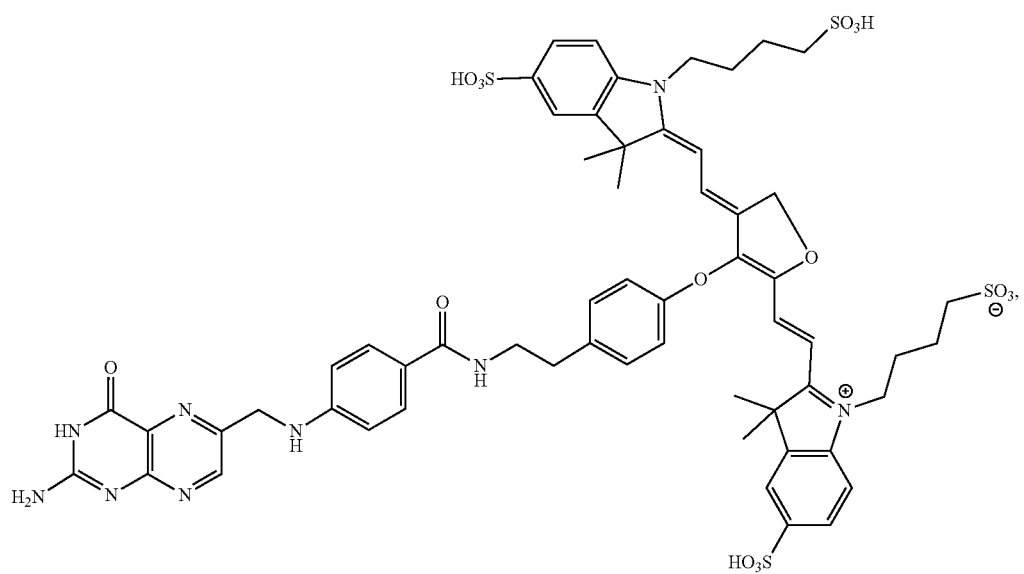

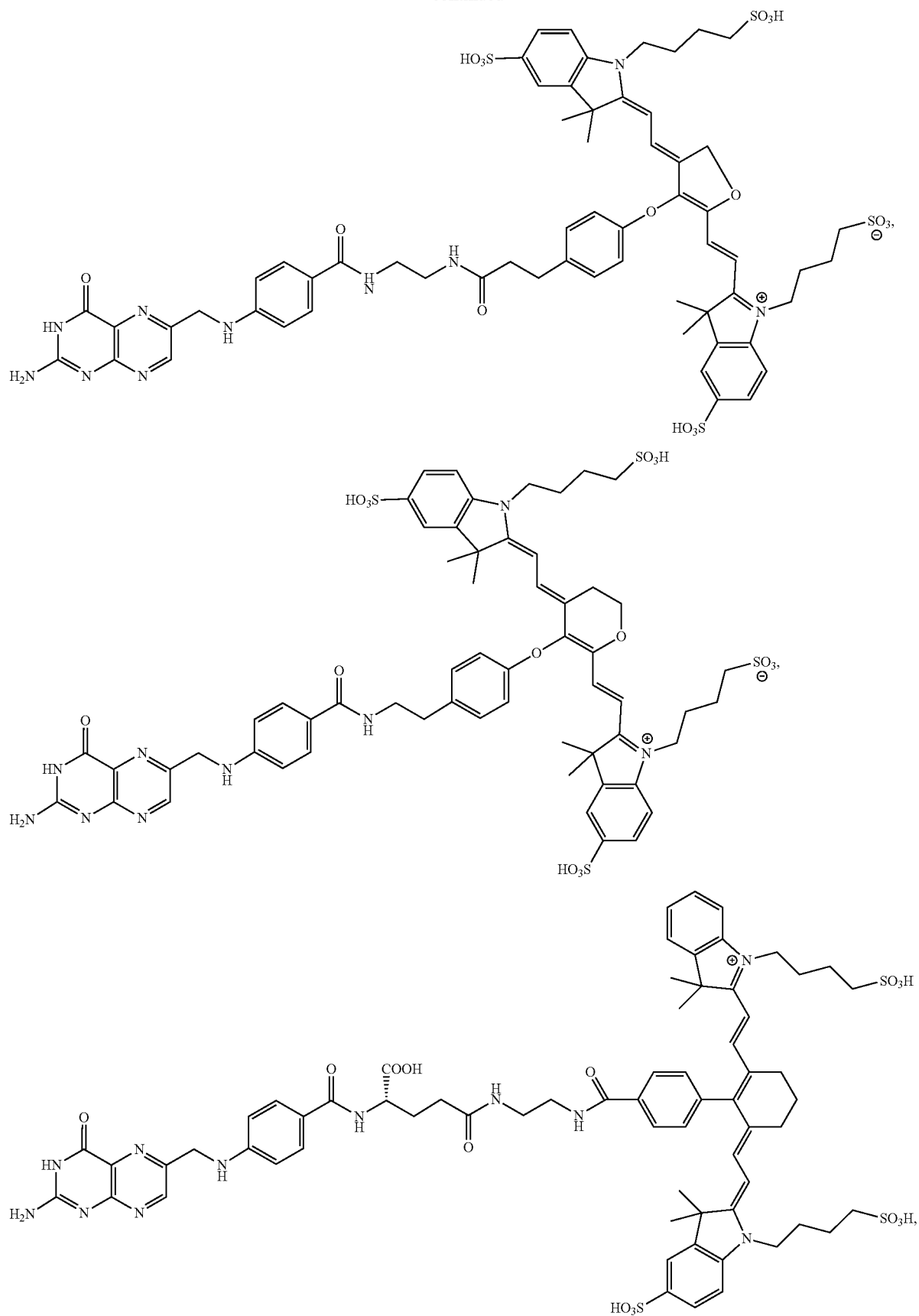

-continued

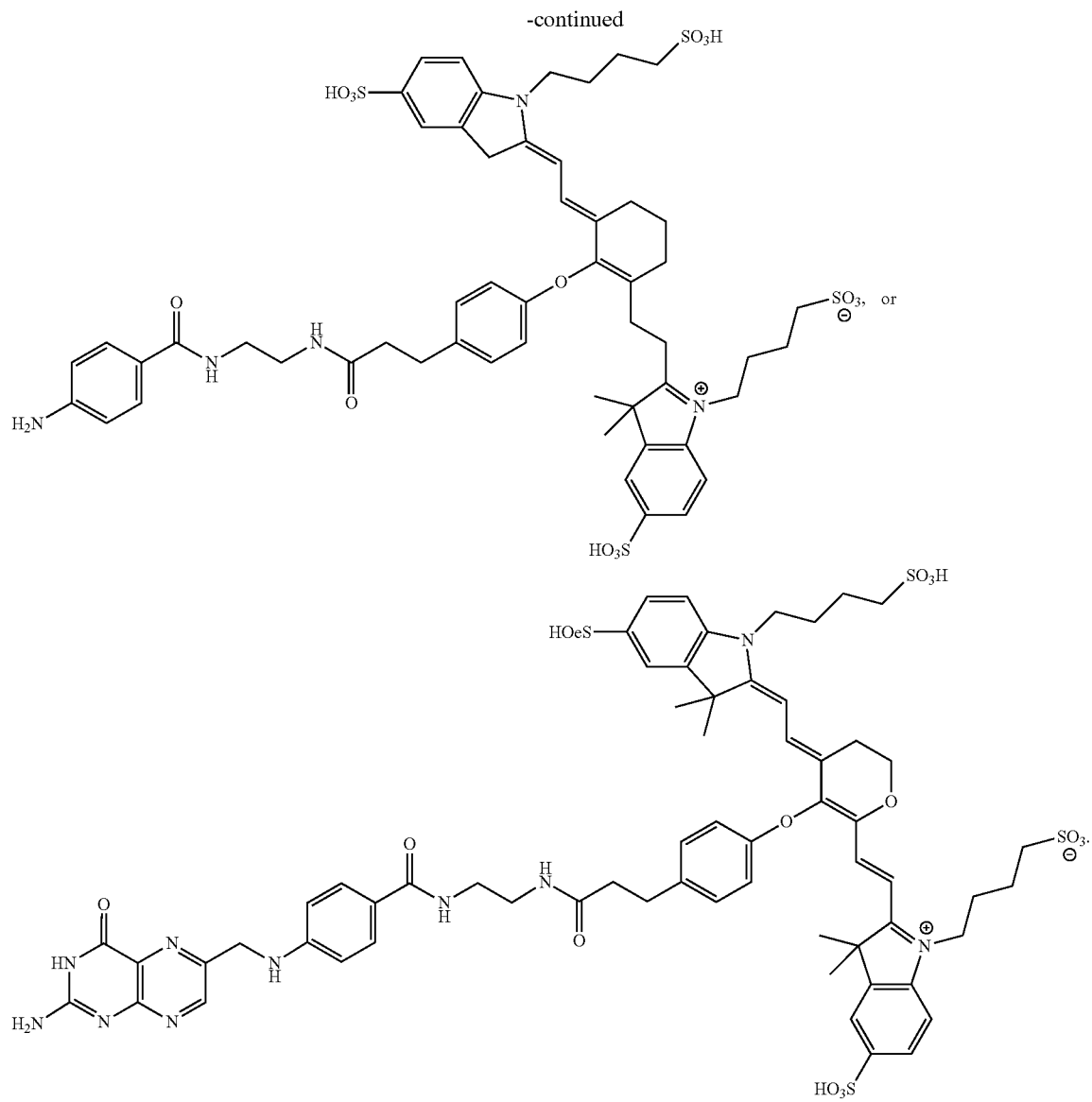

BRIEF DESCRIPTION OF THE DRAWINGS

FIG. 2 1H-NMR of 103.
FIG. 4 1H-NMR of 105.
FIG. 16 1H-NMR of 125.
FIG. 24 1H-NMR of 132.

DETAILED DESCRIPTION

Figure 1:
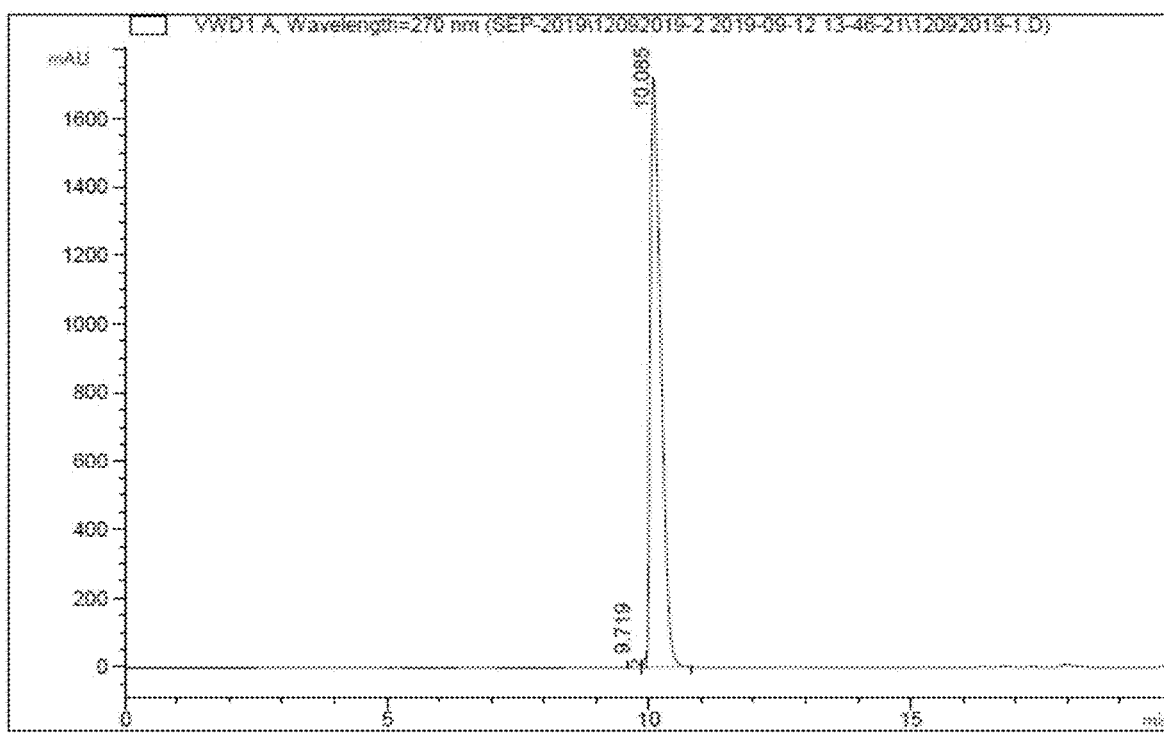
FIG. 1 Chromatogram profile of 103.
Figure 2:
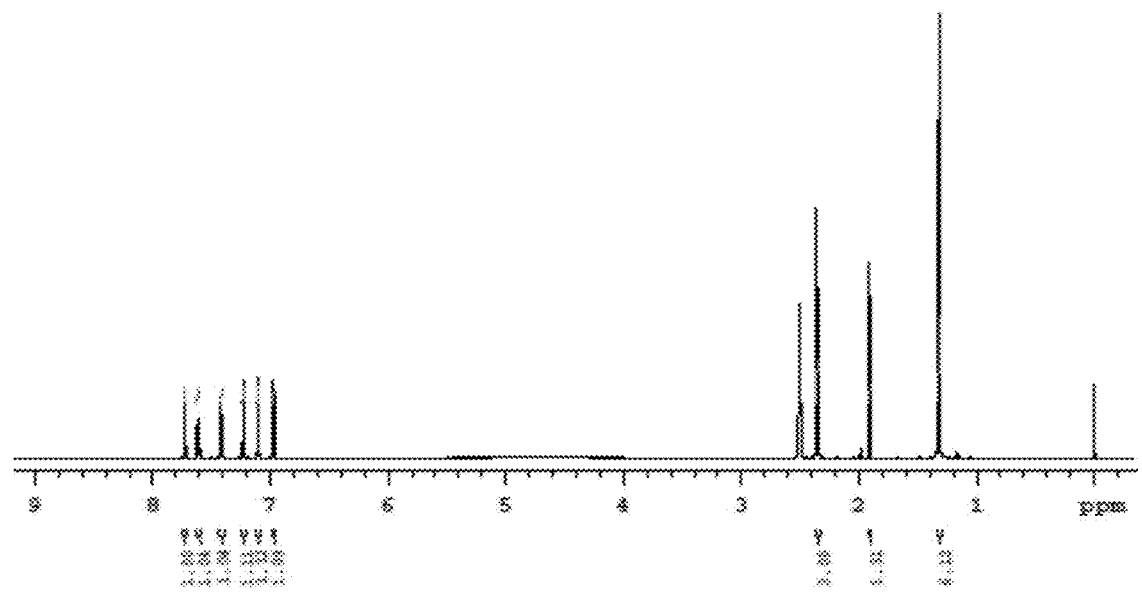
Figure 3:
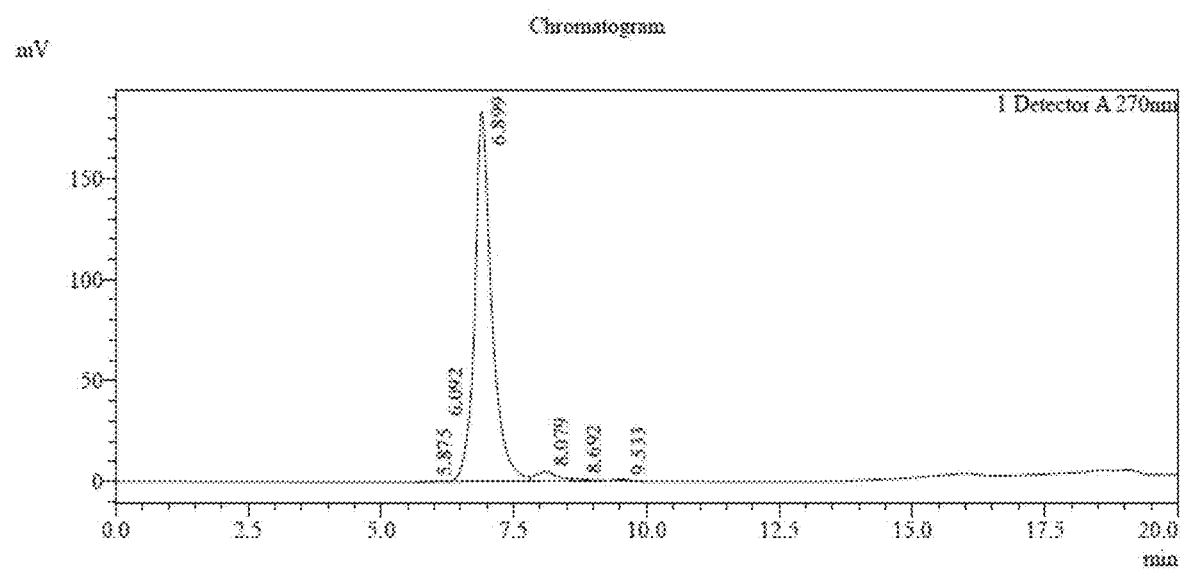
FIG. 3 Chromatogram profile of 105.
Figure 4:
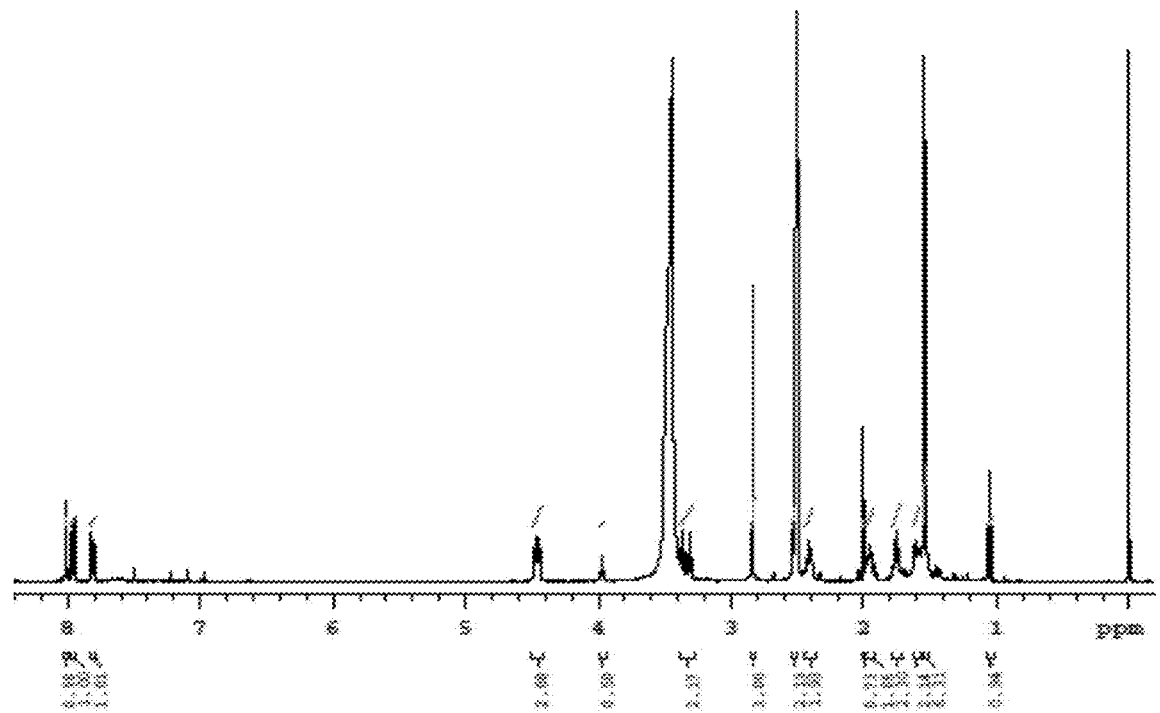
Figure 5:
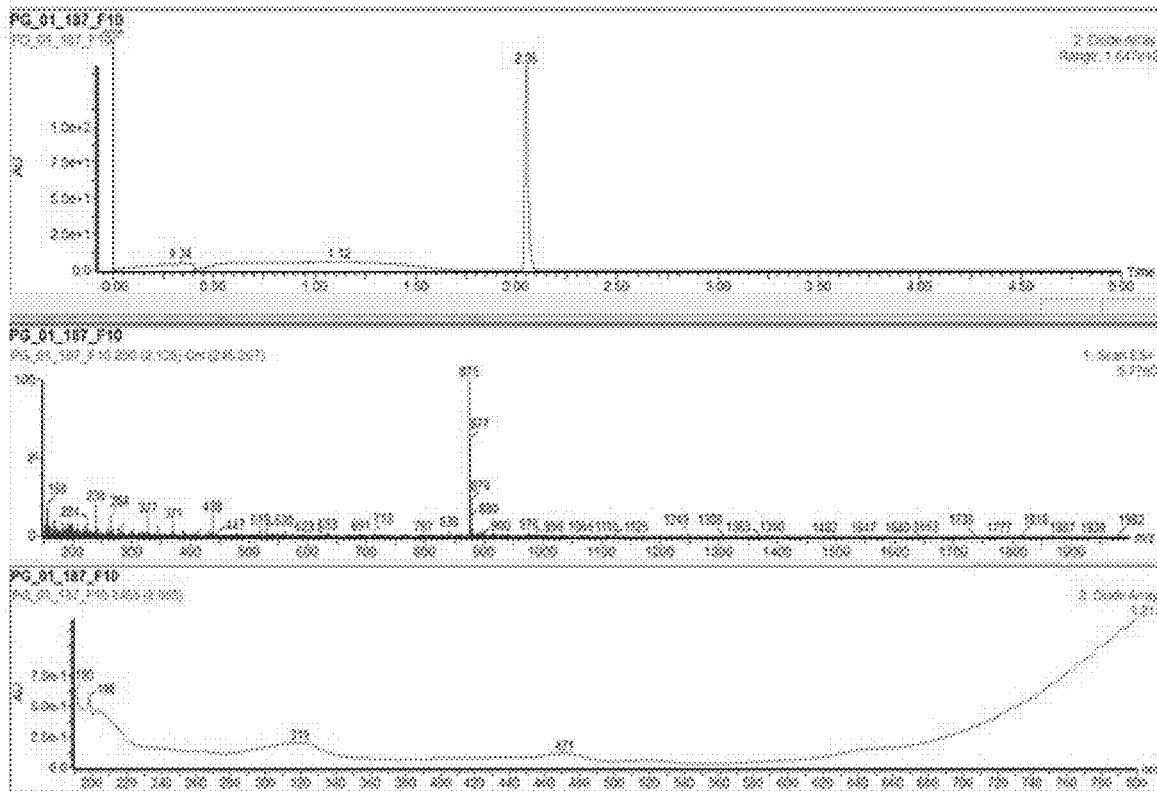
FIG. 5 Chromatogram profile of 106.
Figure 6:
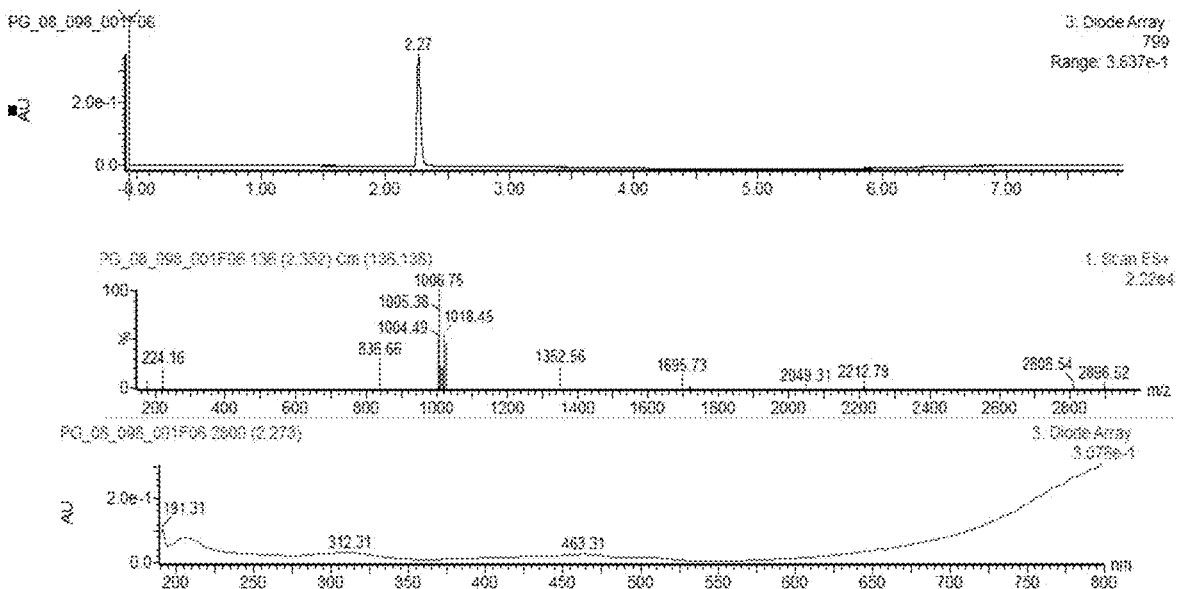
FIG. 6 Chromatogram profile of 108.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission.

Several criteria were considered in the preparation of the fluorescent dye compounds. Ease of synthesis and chemical stability were primary chemical attributes. Spectral properties, such as absorption and emission spectra and quantum yield, were considered.

One aspect of the present technology is one or more fluorescent dyes represented by Formula I:

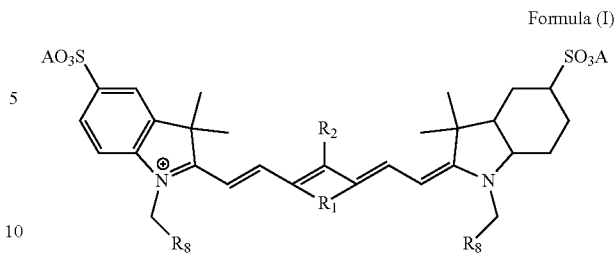

Formula (I)

wherein:
$R_1=(CH_2)_n$ and $n=0, 1, 2, 3, \ldots$
$R_2=$Halogen such as Cl, Br, I or X—$R_3$
$X=(CH_2)_m$, NH, O, S, Se and $m=0, 1, 2, 3, \ldots$
$R_3=[CH_2]_p CH(R_4)COOH$ or $C_6H_4—[CH_2]_p CH(R_4)COOH$ or $(CH_2)_p COOH$ or $(CH_2)_p NH_2$ and $p=0, 1, 2, 3, \ldots$
$R_4=$H, $NHR_5$
$R_5=$H, alkyl group, amine protecting group, sugar
$R_6, R_7=CH_2$, NH, O, S, Se, or combination of them
$R_8=(CH_2)_q SO_3H$ and $q=0, 1, 2, 3, \ldots$
A=counter cation.

Another aspect of the present technology is one or more fluorescent dyes represented by Formula II:

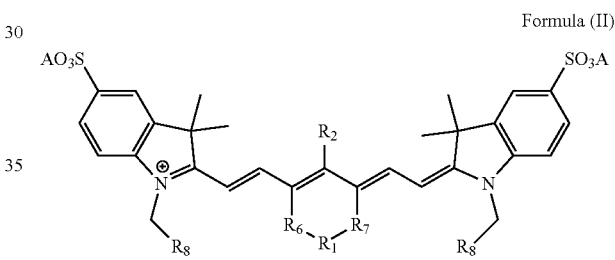

Formula (II)

wherein:
$R_1=(CH_2)_n$ and $n=0, 1, 2, 3, \ldots$
$R_2=$Halogen such as Cl, Br, I or X—$R_3$
$X=(CH_2)_m$, NH, O, S, Se and $m=0, 1, 2, 3, \ldots$
$R_3=[CH_2]_p CH(R_4)COOH$ or $C_6H_4—[CH_2]_p CH(R_4)COOH$ or $(CH_2)_p COOH$ or $(CH_2)_p NH_2$ and $p=0, 1, 2, 3, \ldots$
$R_4=$H, $NHR_5$
$R_5=$H, alkyl group, amine protecting group, sugar
$R_6, R_7=CH_2$, NH, O, S, Se, or combination of them
$R_8=(CH_2)_q SO_3H$ and $q=0, 1, 2, 3, \ldots$
A=counter cation.

Another aspect of the present technology is the synthesis of fluorescent dyes having a formula selected from formula (I) or formula (II)

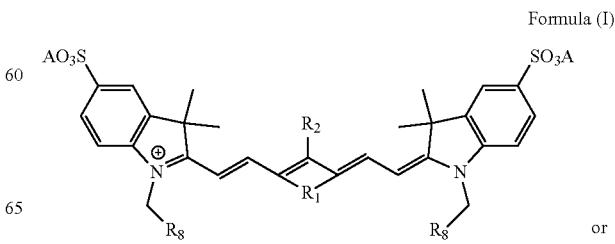

Formula (I)

or

-continued

Formula (II)

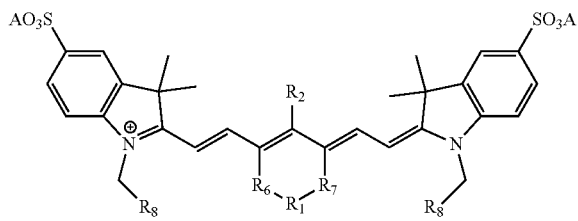

wherein:
$R_1 = (CH_2)_n$ and $n = 0, 1, 2, 3, \ldots$
$R_2 =$ Halogen such as Cl, Br, I or X—$R_3$
$X = (CH_2)_m$, NH, O, S, Se and $m = 0, 1, 2, 3, \ldots$
$R_3 = [CH_2]_p CH(R_4)COOH$ or $C_6H_4$—$[CH_2]_p CH(R_4)COOH$ or $(CH_2)_p COOH$ or $(CH_2)_p NH_2$ and $p = 0, 1, 2, 3, \ldots$
$R_4 = H, NHR_5$
$R_5 = H$, alkyl group, amine protecting group, sugar
$R_6, R_7 = CH_2$, NH, O, S, Se, or combination of them
$R_8 = (CH_2)_q SO_3H$ and $q = 0, 1, 2, 3, \ldots$
A = counter cation
comprising the steps of
reacting a compound of a formula

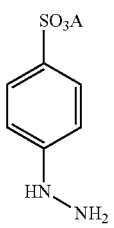

with a compound of a formula

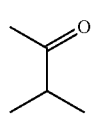

in the presence of an acetate salt to generate a compound of the formula

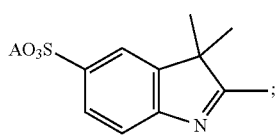

reacting the resulting compound with a compound of the formula

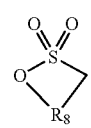

in the presence of nonpolar solvent to generate a compound of the formula

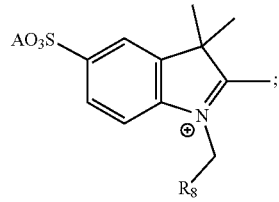

reacting a compound of the formula

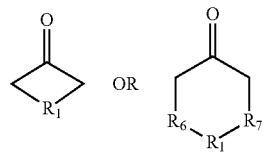

in the presence of an acetate salt, sultone, and a nonpolar solvent to generate a compound of the formula

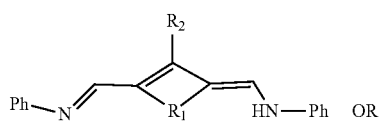

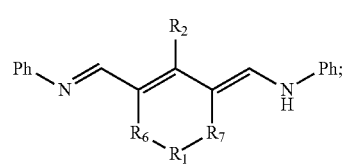

reacting the compound of the formula

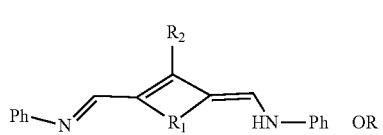

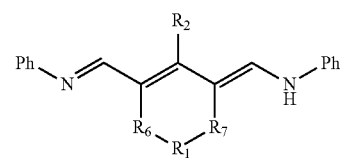

with a compound of the formula

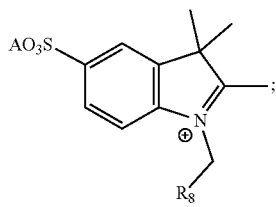

in the presence of an acetate salt to generate a compound of the formula

Formula (I)

[structure]

or

Formula (II)

[structure]

In some aspects, the compound of the formula

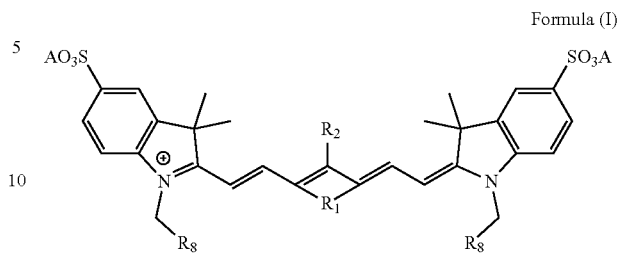

is reacted with X—R in polar solvent, wherein X=OH, NH2, SH, or SeH.

In another aspect of the method, the compound is precipitated by nonpolar solvent or purified by chromatographic methods or crystallization methods. In another aspect of the invention, the nonpolar solvent is an organic solvent. In another aspect of the invention, the polar solvent is an organic solvent. In another aspect of the invention, the yield of the resulting compound in any step is at least 60%, alternatively at least 65%, alternatively at least 70%, alternatively at least 75%, alternatively at least 80%, alternatively at least 85%. In another aspect of the invention, the purity of the resulting compound of any step is at least 90%, alternatively at least 92%, alternatively at least 95%, alternatively at least 97%. In another aspect of the invention, the resulting compound is selected from the group consisting of:

106

[structure]

107

[structure]

-continued
108
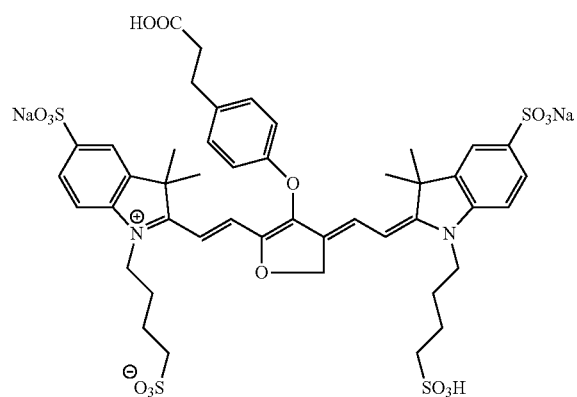
109
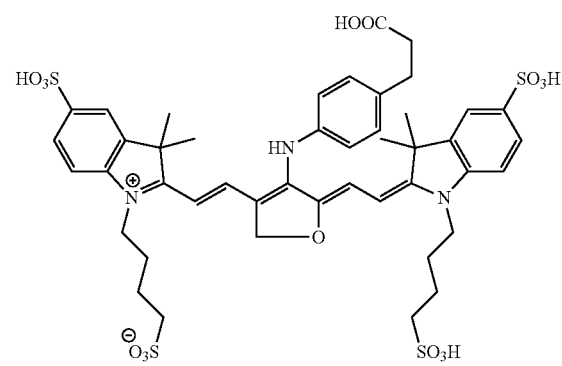
110
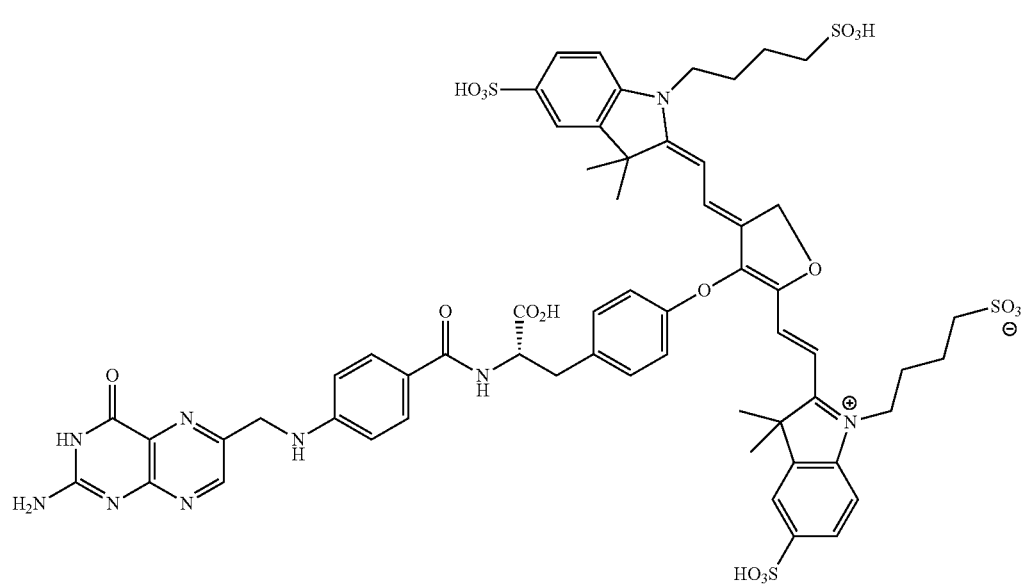
115
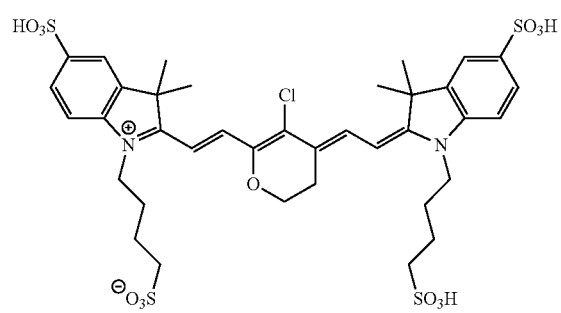
116
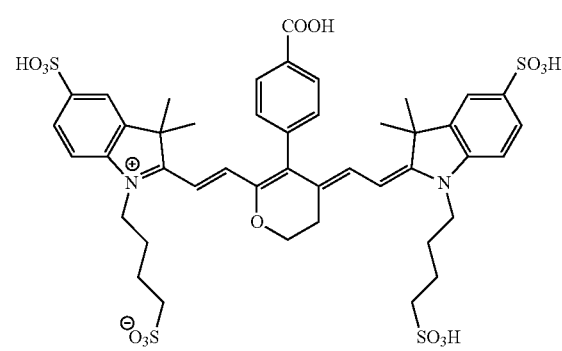

-continued
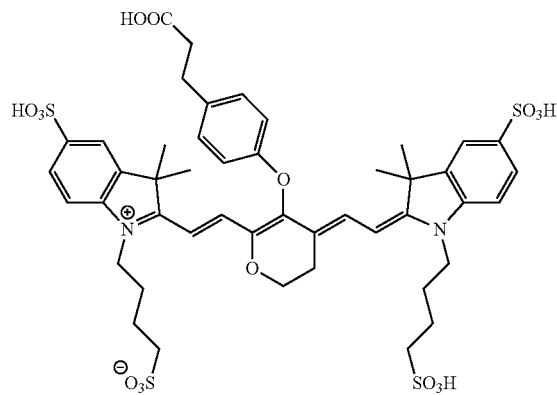
117
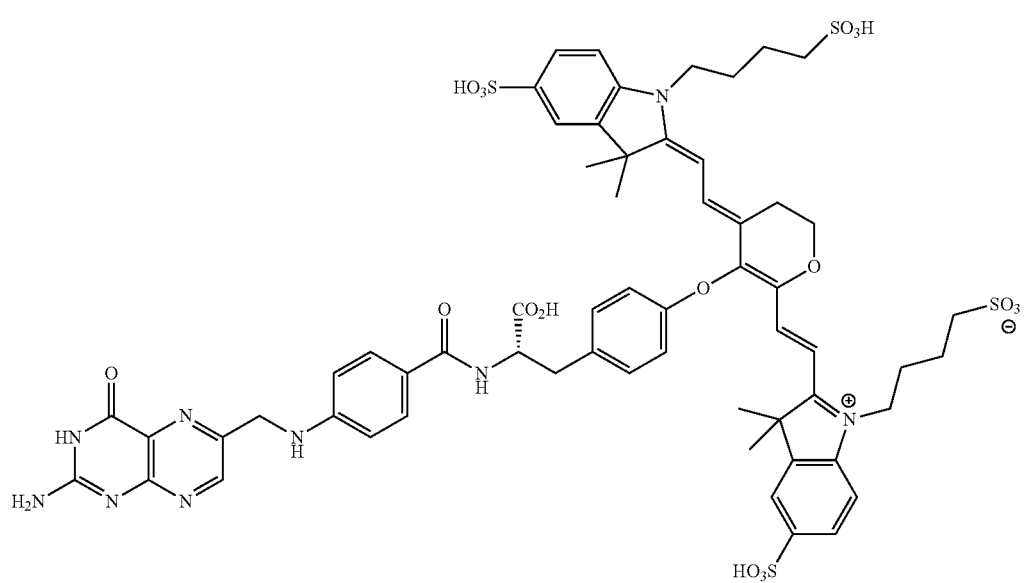
118
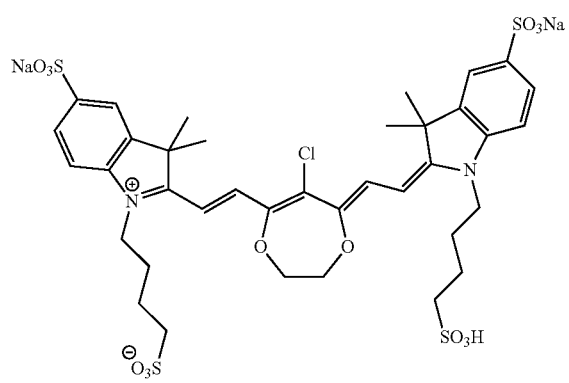
120
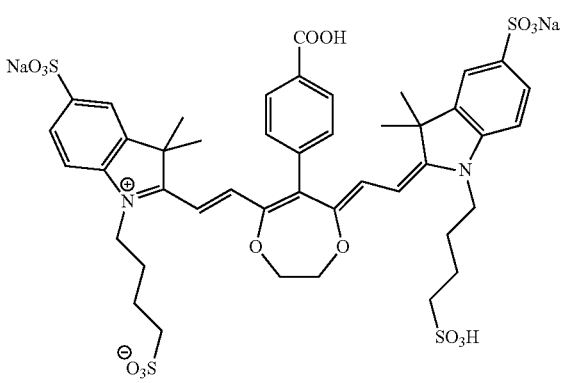
121

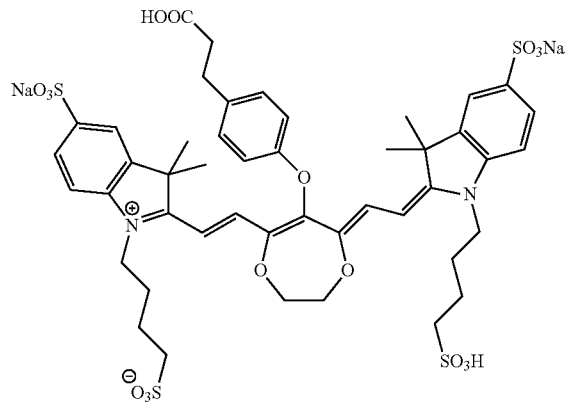
122
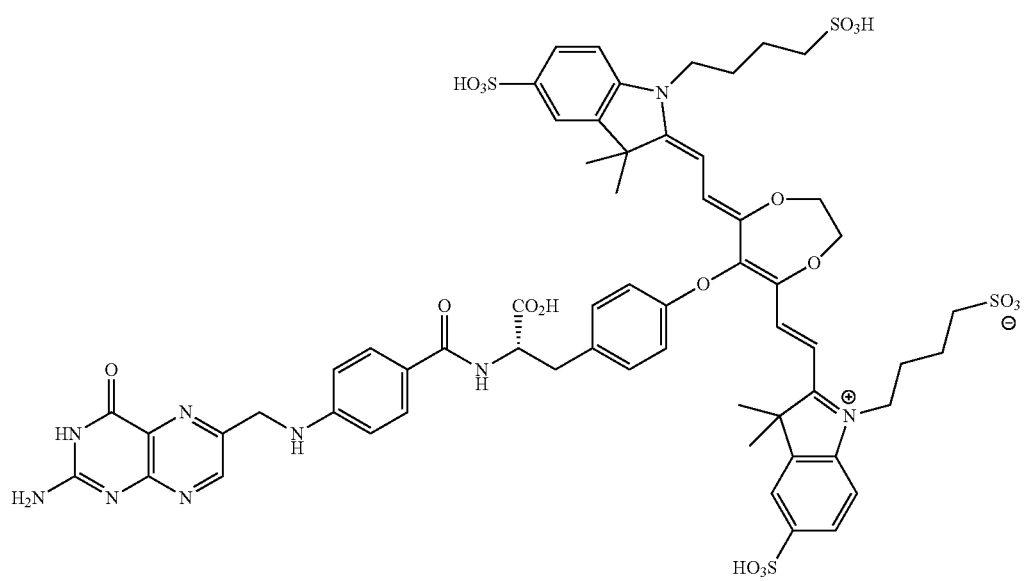
123
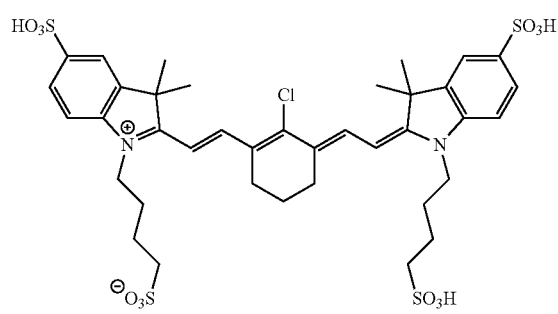
125
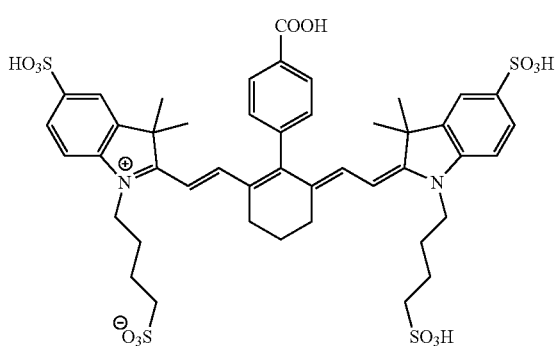
126

-continued
127
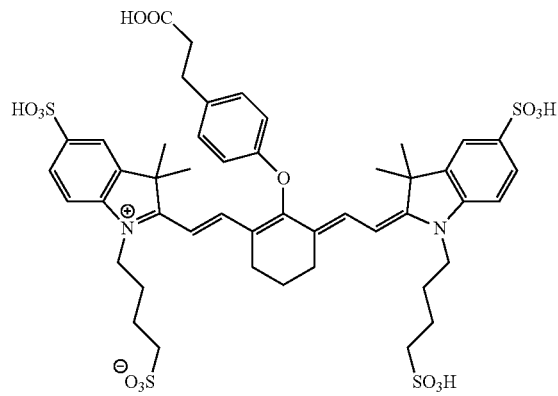
128
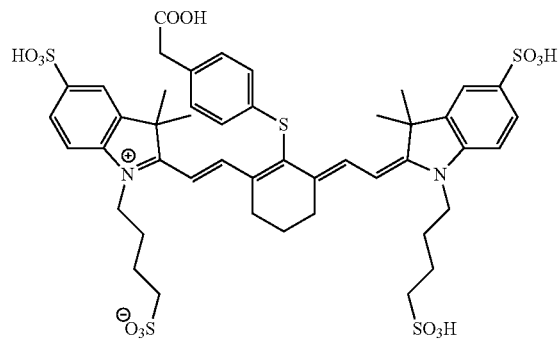
129
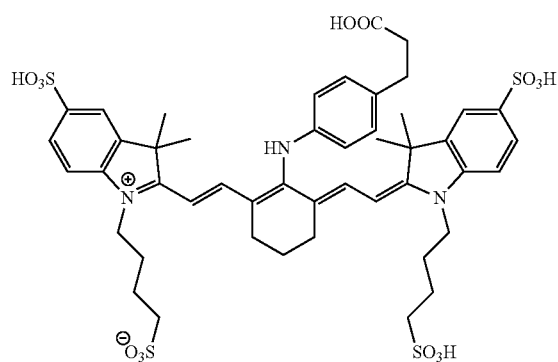
130
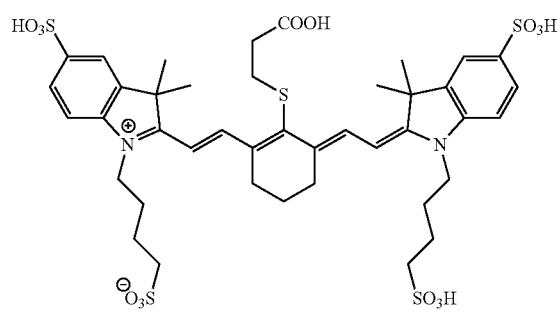
131
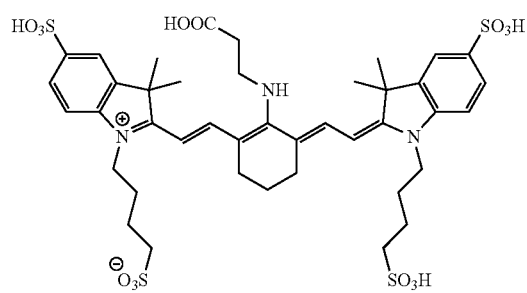
and

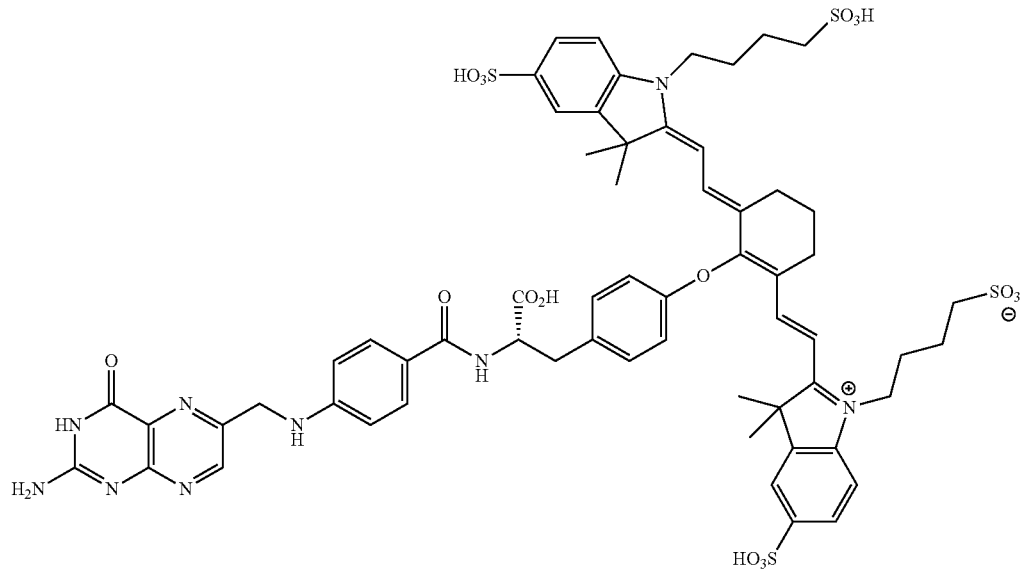

132

The dyes of the present technology have numerous properties. Increasing of ring size (using $R_1$) decreases the λmax of the dye molecule. Increasing the number of electronegative atoms (using $R_2$, $R_6$, and $R_7$) increases the λmax the dye molecule. The variation of the linker (using $R_3$, $R_4$, or $R_5$) gives an extra conjugation site to attach a linker or ligand that can be utilized by the dye to target a tumor or inflammatory site with a diseased cell. The novel and unique synthesis strategies result in highly pure and high yielding dye molecules with various optical properties such as absorption maxima (λmax), fluorescence intensity, extinction coefficient (ε), etc. These and other advantages will be apparent from the detailed description below.

Another aspect of the present technology are fluorescent dye compounds represented by the formulas below:

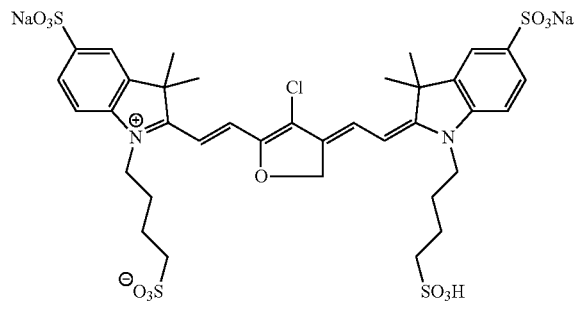

106

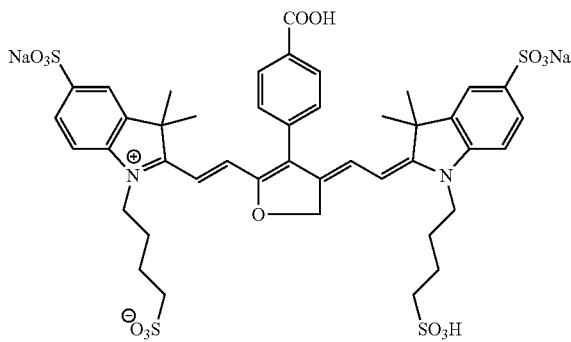

107

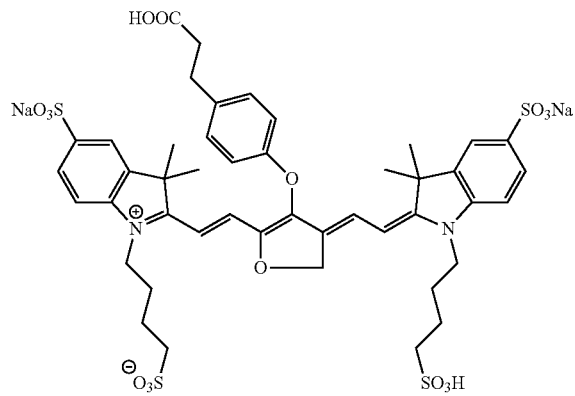

108

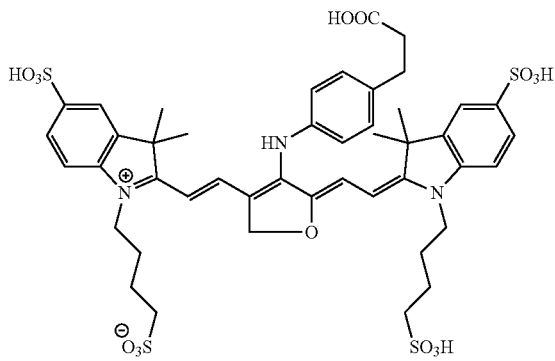

109

110
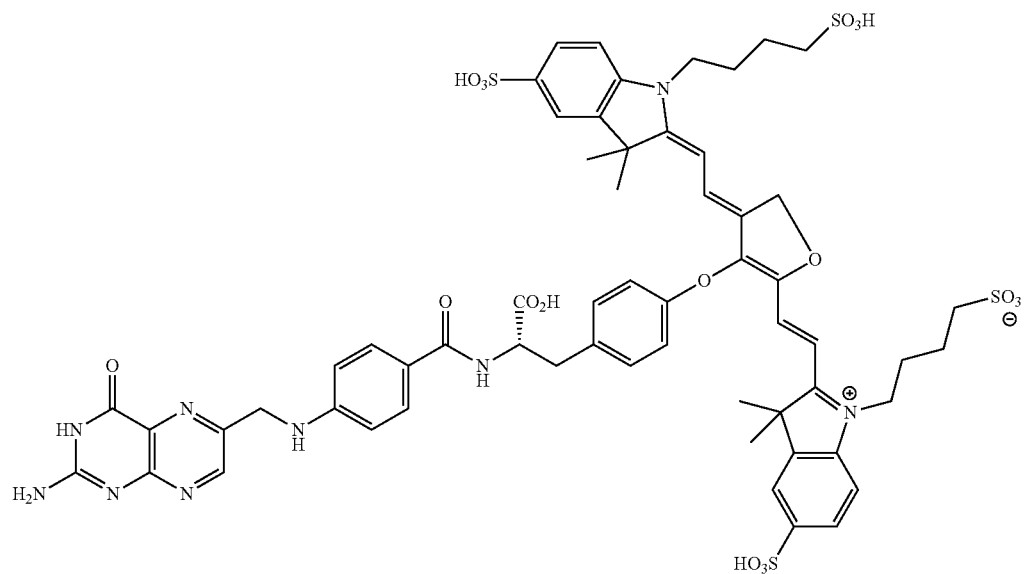
115 116
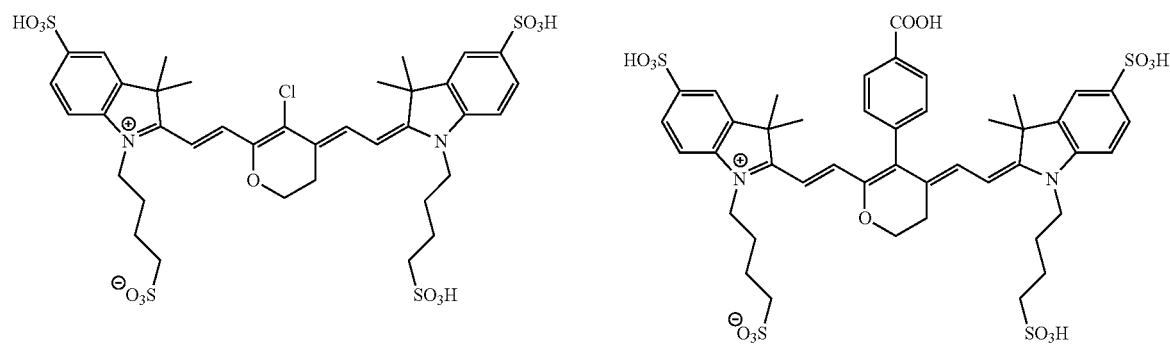
117
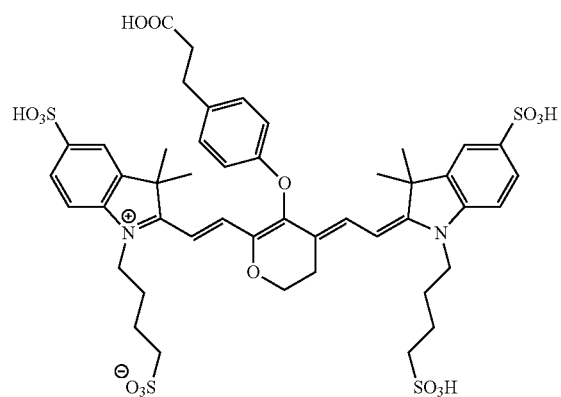

-continued
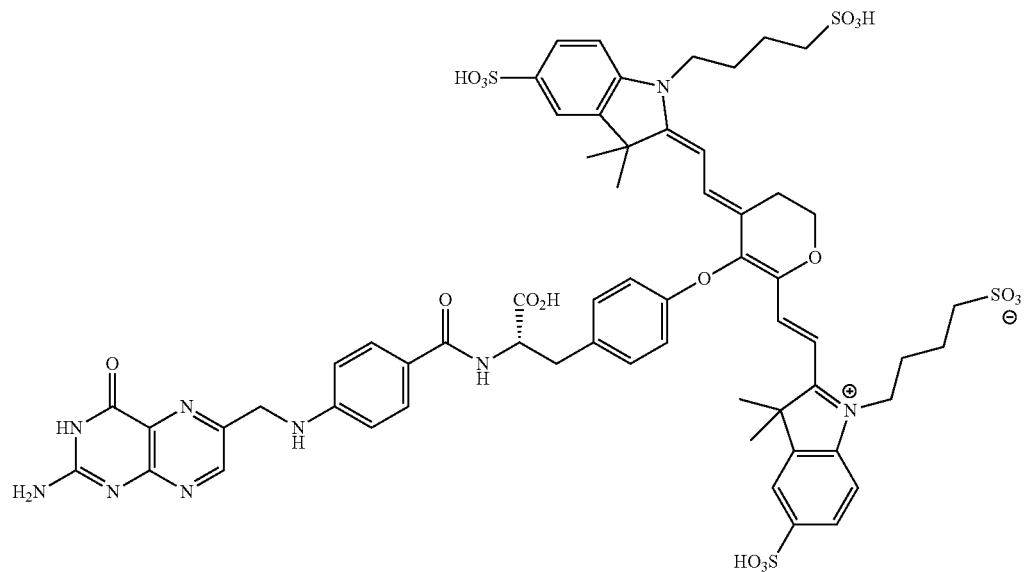
118
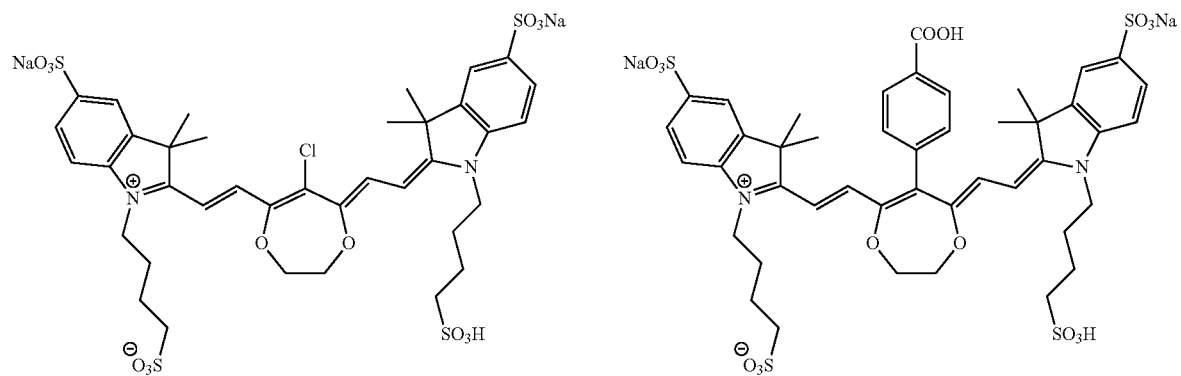
120
121
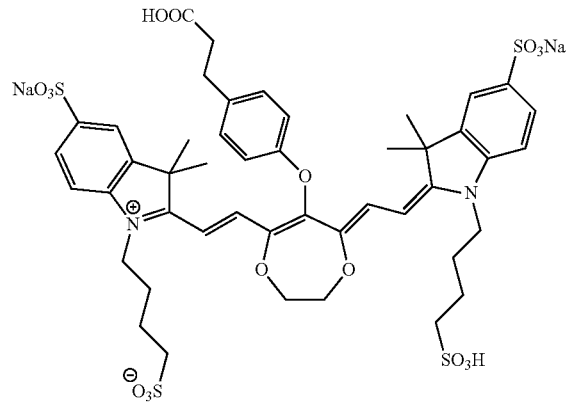
122

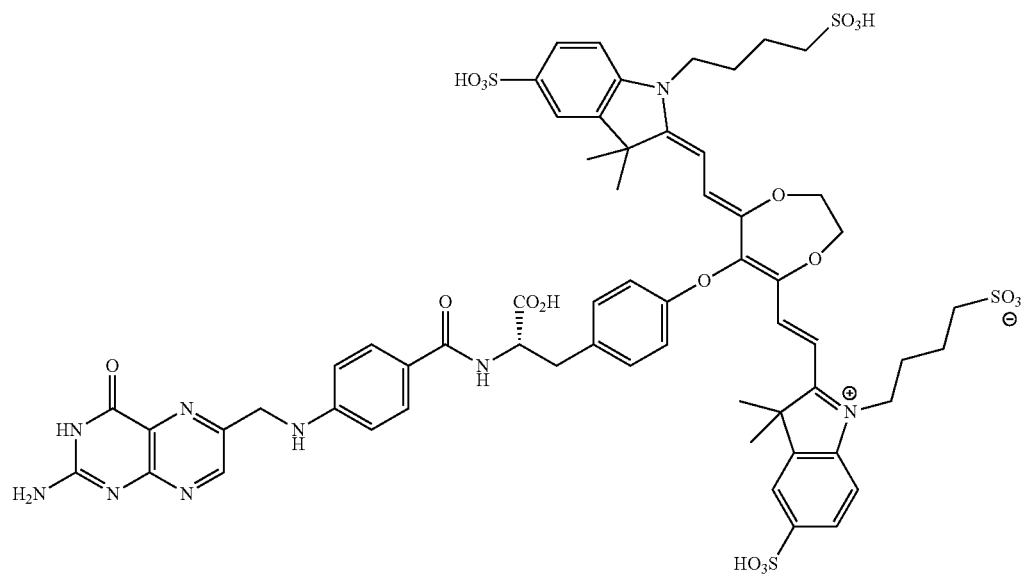
123
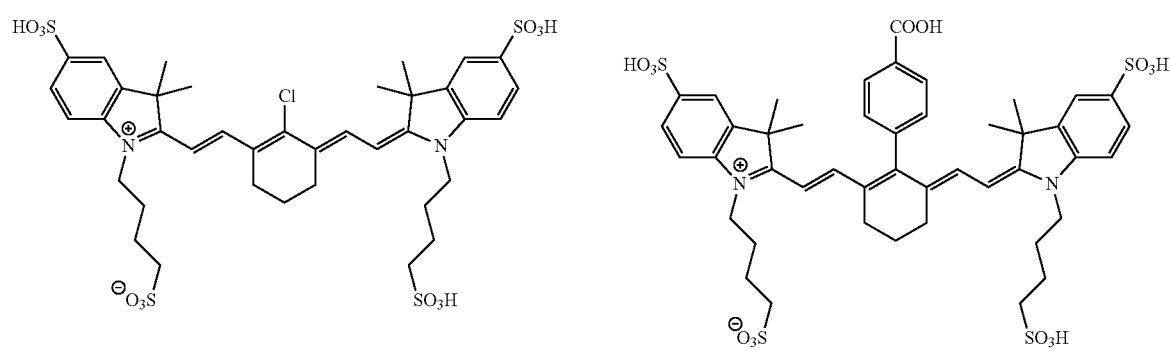
125   126
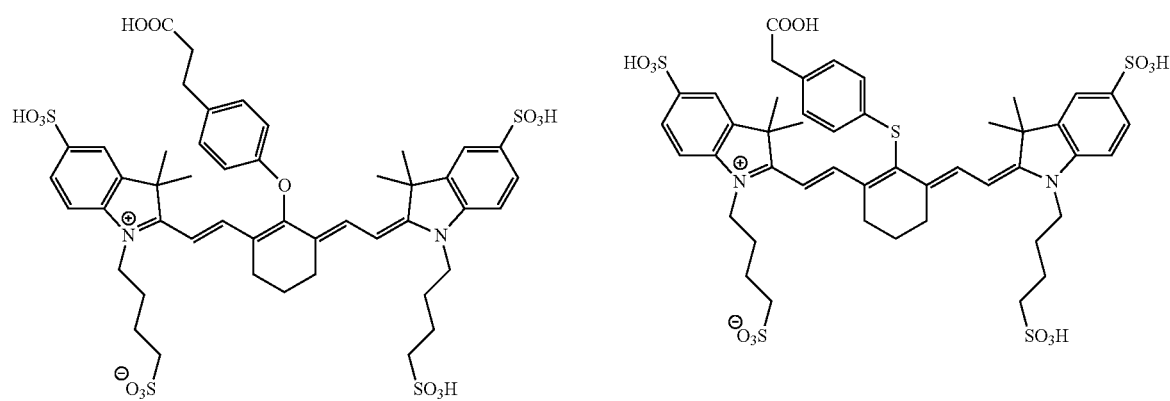
127   128

-continued
129
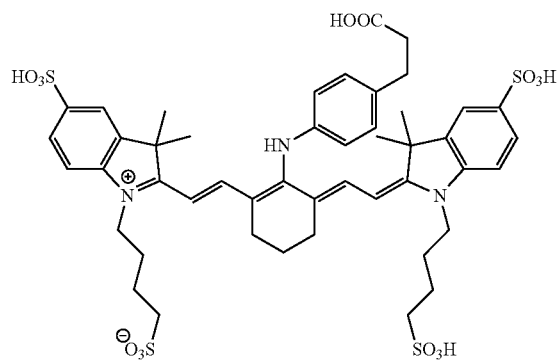
130
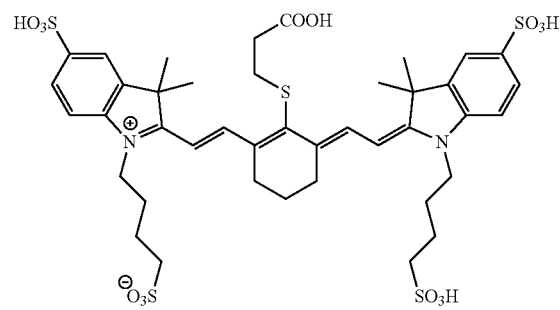
131
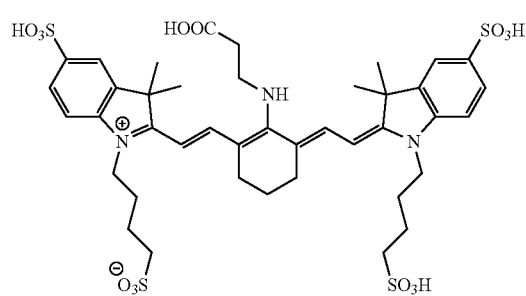
132
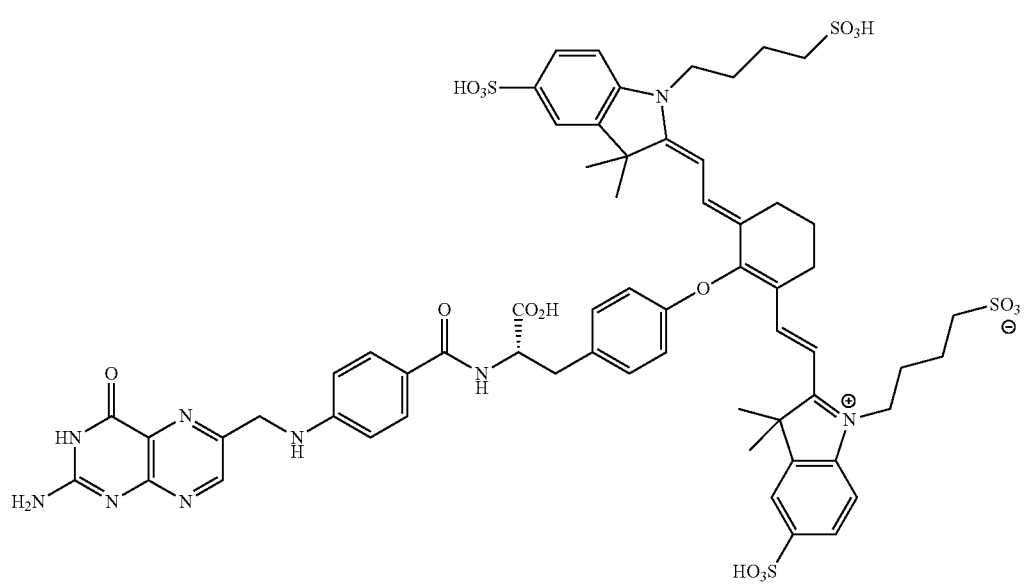

Another aspect of the present technology are fluorescent compounds represented by the following formulas:
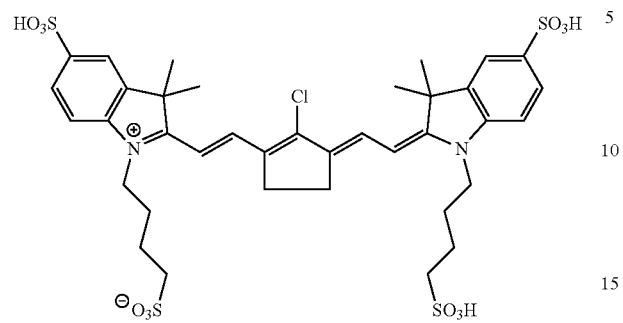
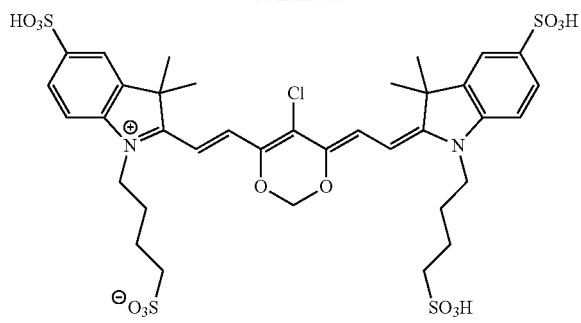
-continued
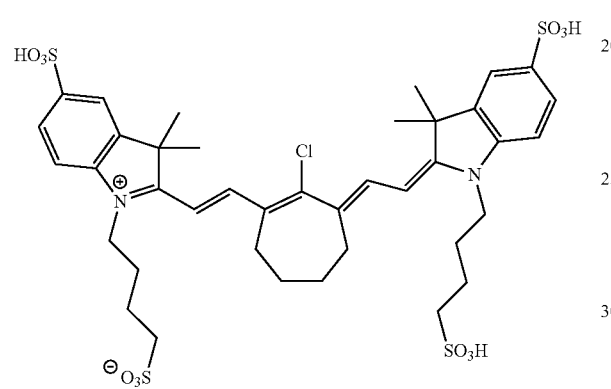
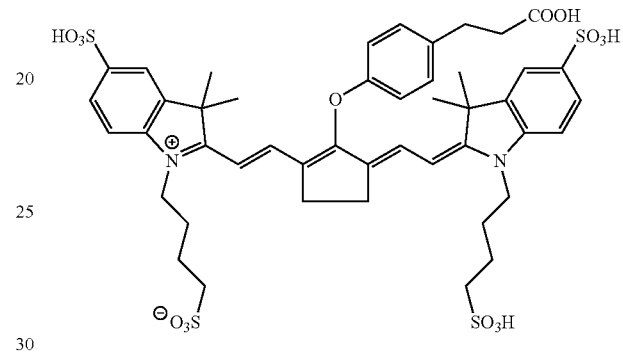
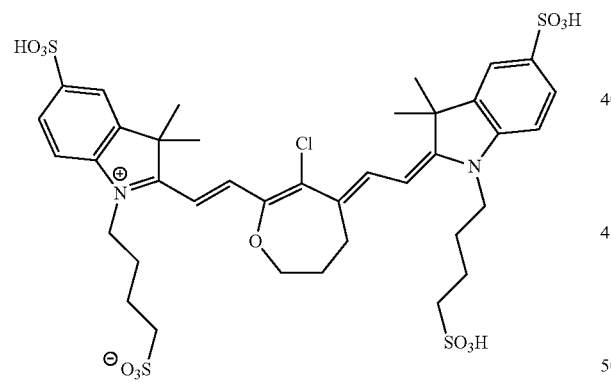
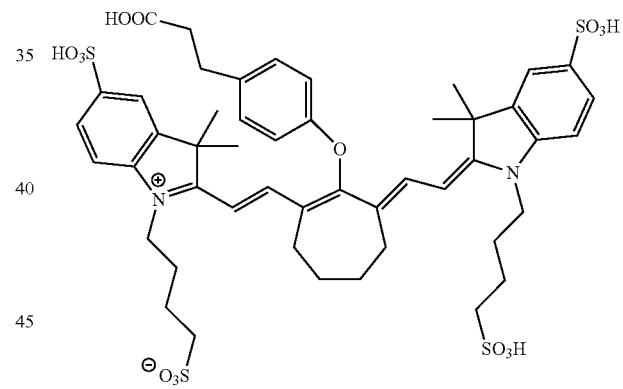
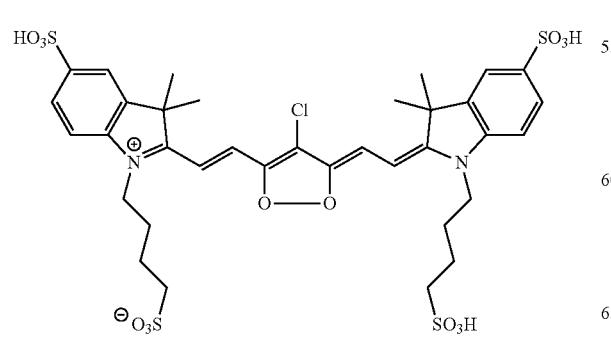
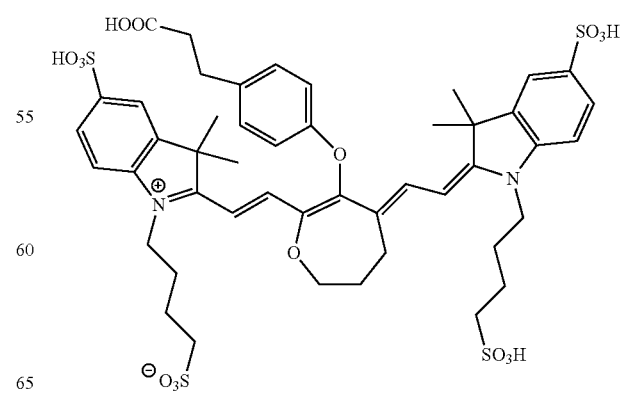

-continued

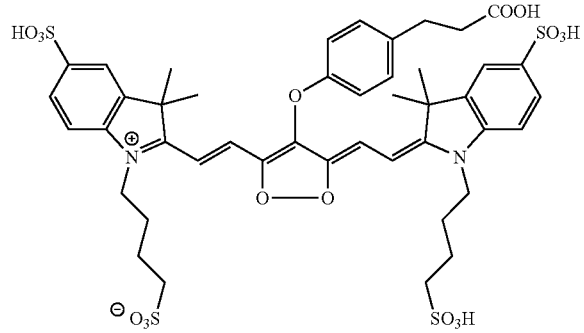

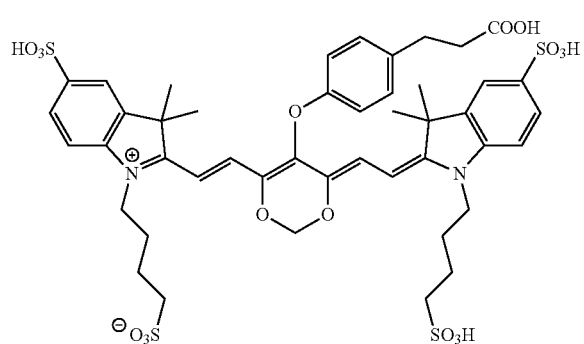

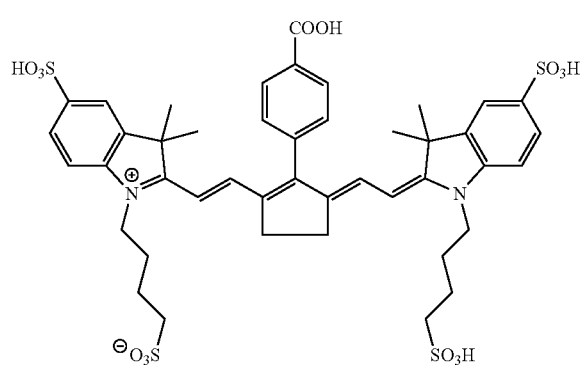

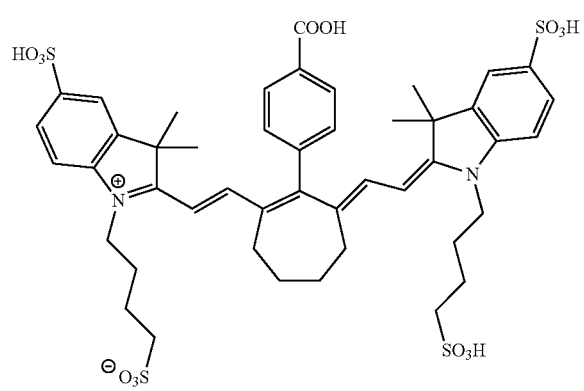

-continued

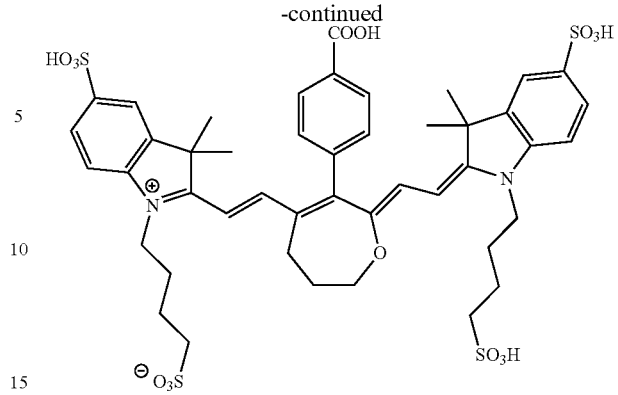

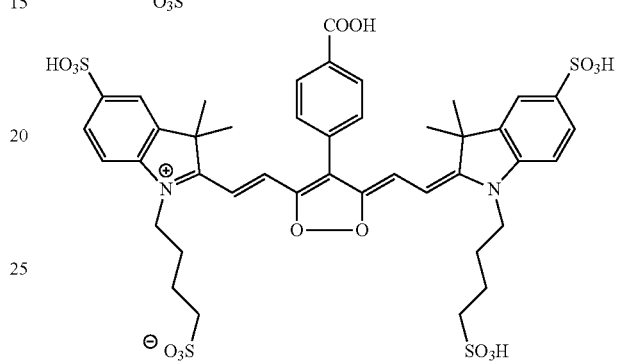

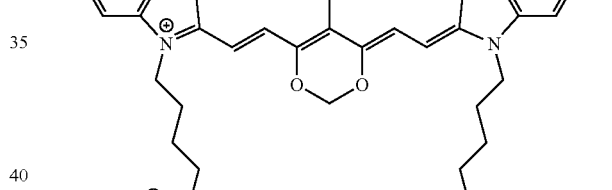

The counter ion of the fluorescent dye compounds includes, but is not limited to, for example, sodium, potassium, calcium, magnesium, lithium, cholinate, lysinium, ammonium, or hydrogen.

The compounds can be used with fluorescence-mediated molecular tomographic imaging systems, such as those designed to detect near-infrared fluorescence activation in deep tissues. The compounds provide molecular and tissue specificity, yield high fluorescence contrast, brighter fluorescence signal, and reduce background autofluorescence, allowing for improved early detection and molecular target assessment of diseased tissue in vivo (e.g., cancers). The compounds can also be used for deep tissue three-dimensional imaging, targeted surgery, and methods for quantifying the amount of a target cell type in a biological sample.

In some aspects of the invention, the fluorescent dye compounds can be used for image-guided surgery, tumor imaging, lymph node imaging, inflammatory diseases, atherosclerosis, infection diseases, forensic applications, mineral applications, dental, gel staining, DNA sequencing, nerve staining, or plastic surgery.

In some aspects of the invention, the fluorescent dye compound may be incorporated into targeting moieties with may include a protein or polypeptide, such as an antibody, or biologically active fragment thereof, preferably a monoclonal antibody, small molecules, aptamers, DNA, RNA, or amino acids and derivatives thereof. The supplemental fluorescing targeting construct(s) used in the practice of the disclosed method may also be or comprise polyclonal or monoclonal antibodies tagged with a fluorophore. The term "antibody" as used in this disclosure includes intact molecules as well as functional fragments thereof, such as Fab, F(ab')2, and Fv that are capable of binding the epitopic determinant. Methods of making these fragments are known in the art. (See e.g., example, Harlow & Lane, Antibodies: A Laboratory Manual, Cold Spring Harbor Laboratory, New York, 1988, incorporated herein by reference). As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

In some aspects of the invention, the fluorescent dye compounds are incorporated into targeting moieties with a formula selected from the following:

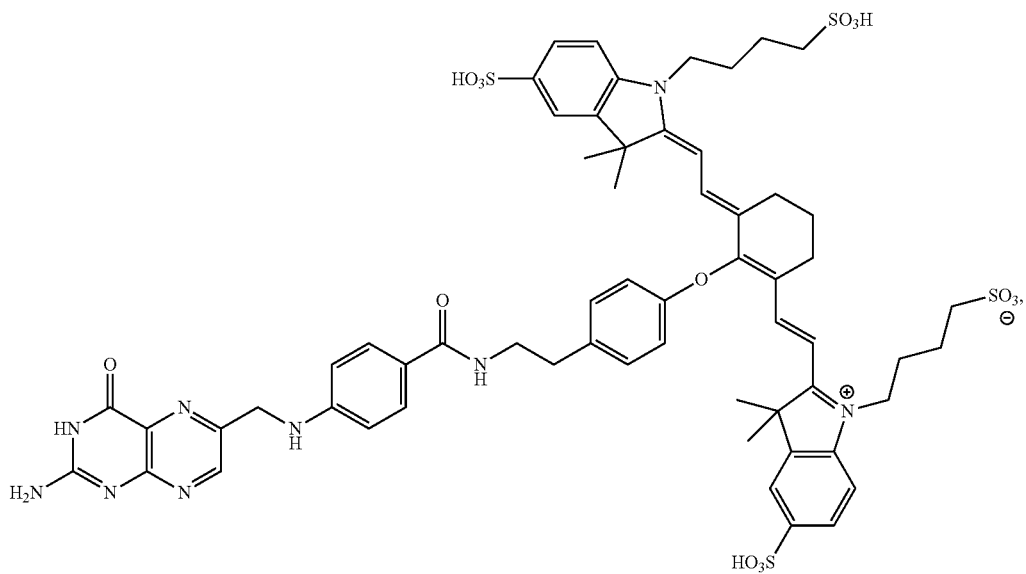

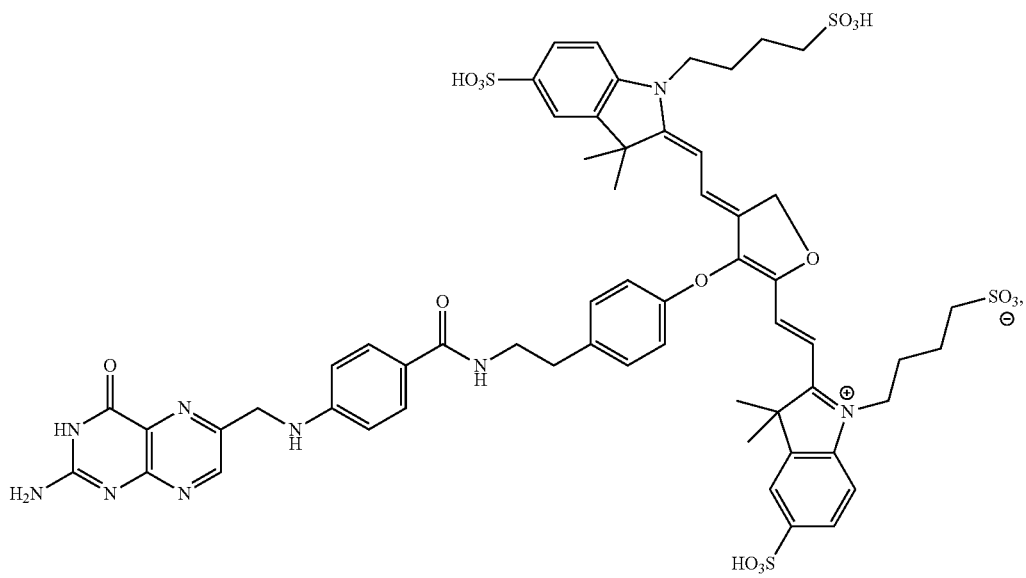

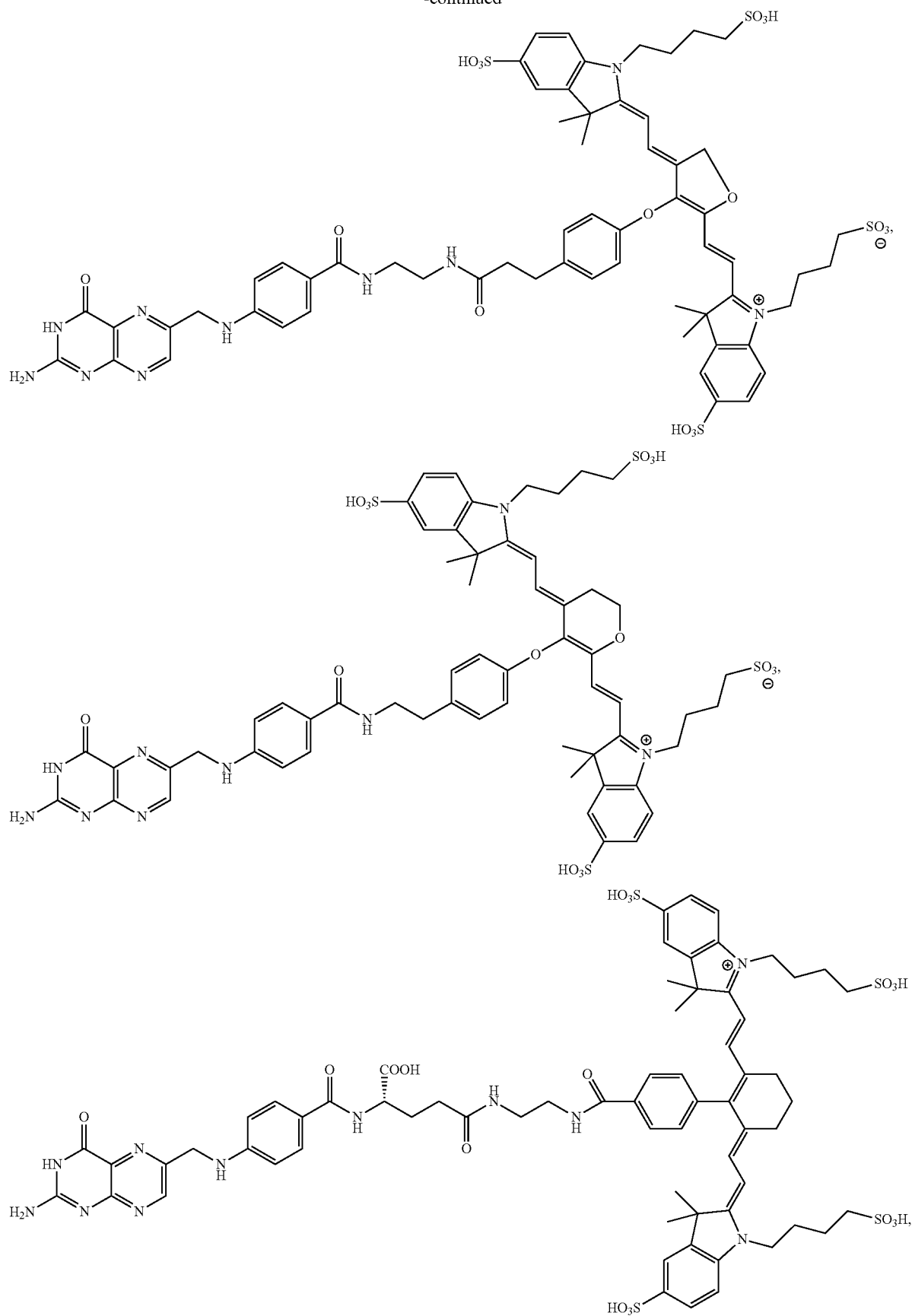

-continued

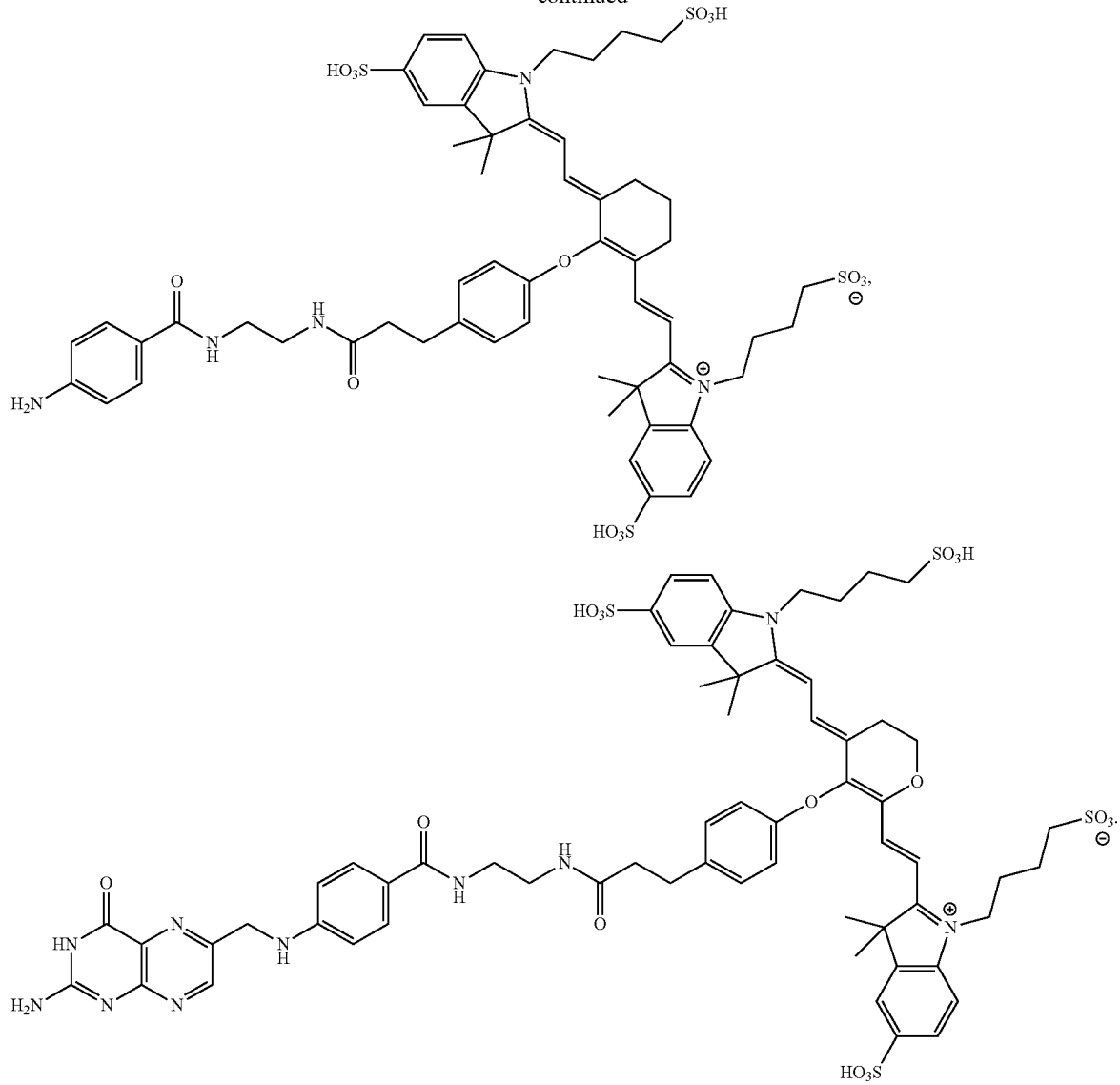

In some embodiments, the amino acid or amino acid derivative induces a shift in the electronic emission spectrum, the electronic absorption spectrum, or both the electronic emission and absorption spectrum, relative to the electronic spectra of the unmodified dye molecule. Suitably, the shift in the electronic spectrum is a bathochromic shift (i.e., shift to longer wavelength/lower frequency) that helps to improve the detection of the compound in the near-infrared (NIR) spectral window and/or reduce the amount of background signal, autofluorescence, interferences from the tissue surrounding the area being visualized. More specifically, this shift in the electronic spectrum is particularly observed with NIR dyes that comprise electronegative atoms that are incorporated into the 6-membered ring. Thus, in certain aspects, the amino acid or amino acid derivative comprises an electron-rich moiety such as, for example, oxygen, sulfur, or nitrogen. Non-limiting examples of such amino acids can include cysteine, methionine, threonine, serine, tyrosine, phenylalanine, tryptophan, histidine, lysine, arginine, aspartic acid, glutamic acid, asparagine, and glutamine, or derivatives thereof.

In some aspect, fluorescent dye compound may be incorporated or used with other fluorescing targeting constructs (e.g., antibodies, or biologically active fragments thereof, having attached fluorophores) that bind to other receptors or antigens on the tumor or tissue (e.g., a site of atherosclerosis, infection, cardiovascular diseases, neurodegenerative diseases, immunologic diseases, autoimmune diseases, respiratory diseases, metabolic diseases, inherited diseases, infectious diseases, bone diseases, and environmental diseases or the like) to be imaged. Any additional targeting moiety that specifically targets the tumor or specific site on the tissue may be used provided that it is specific for the site to be monitored. The purpose of the additional fluorescing targeting construct is to increase the intensity of fluorescence at the site to be monitored, thereby aiding in the detection of diseased or abnormal tissue in the body part. For example, a given tumor may have numerous markers, and in addition to the compounds of the present disclosure, a cocktail of fluorescent moieties are provided which are specific for that given tumor such that the signal emanating from the tumor is generated by more than one compound or fluorescent moiety that has targeted and become localized to the tumor site of interest.

In some aspects, in practice, the skilled person would administer a compound of the present disclosure either alone or as part of a cocktail of targeting detectable moieties and allow these compounds and targeting moieties to bind to and/or be taken up by any targeting tissue that may be present at the site under investigation and then provide a supply of the light source. Typically, the compounds of the present disclosure and any additional targeting moieties will be administered prior to surgery for a time and in compositions that allow the fluorescent compounds of the present disclosure as well as any additional fluorescent constructs to be taken up by the target tissue.

Those of skill in the art will be able to devise combinations of successively administered fluorescing targeting constructs, each of which specifically binds to the target site. It is preferable that all of the fluorescing targeting constructs used in such cocktails to identify the target tissue comprise fluorophores that fluoresce within the same wavelength band or at the same wavelength as does the compound of the present disclosure (e.g., a fluorescing sensitive to near-infrared wavelength of light in the compounds of the present disclosure) to minimize the number of different light sources that need to be employed to excite simultaneous fluorescence from all of the different targeting constructs used in the practice of the disclosure method. However, it is contemplated that the additional targeting moieties other than the compounds of the present disclosure may fluoresce in response to the irradiating light at a different color (i.e., has a different wavelength) than that from the fluorescent compounds of the present disclosure. The difference in the colors of the fluorescence emanating from the compounds of the present disclosure and those of the additional targeting compounds may aid the observer in determining the location and size of the diseased tissue. In some examples, it may be desirable to include fluorophores in targeting constructs targeted to target normal tissue and the compounds of the present disclosure to target diseased tissue such that the contrast between the diseased tissue and normal tissue is further enhanced to further aid the observer in determining the location and size of the target tissue. The use of such additional fluorophores and targeting agents in addition to the compounds of the present disclosure provides the advantage that any natural fluorescence emanating from normal tissue is obscured by the fluorescence emanating from fluorophore(s) in supplemental targeting constructs targeted to the normal tissue in the body part. The greater the difference in color between the fluorescence emanating from normal and target tissue, the easier it is for the observer to visualize the outlines and size of the target tissue. For instance, targeting a fluorescing targeting construct comprising a fluorophore producing infrared light from the compounds of the present disclosure to the target tissue (i.e., abnormal tissue) and a fluorophore producing green light to healthy tissue aids the observer in distinguishing the target tissue from the normal tissue. Those of skill in the art can readily select a combination of fluorophores that present a distinct visual color contrast.

The spectrum of light used in the practice of the disclosed method is selected to contain at least one wavelength that corresponds to the predominate excitation wavelength of the targeting construct, or of a biologically compatible fluorescing moiety contained within the targeting construct.

However, when a combination of targeting ligands that fluoresce at different wavelengths is used in the practice of the disclosure, the spectrum of the excitation light must be broad enough to provide at least one excitation wavelength for each of the fluorophores used. For example, it is particularly beneficial when fluorophores of different colors are selected to distinguish normal from diseased tissue, that the excitation spectrum of the light(s) includes excitation wavelengths for the fluorophores targeted to normal and target tissue.

Fluorescent Dye Compounds and their Synthesis

The compounds disclosed herein can be made using conventional methods known in the literature. However, in specific preferred embodiments, the present disclosure provides more efficient synthetic methods for generating the compounds described herein (i.e., Compounds of Formula I). For example, the compounds having the aforementioned formulas can be prepared in accordance with the general schemes outlined in each of Examples below.

EXAMPLES

Preparation of Formula (I) and Formula (II)

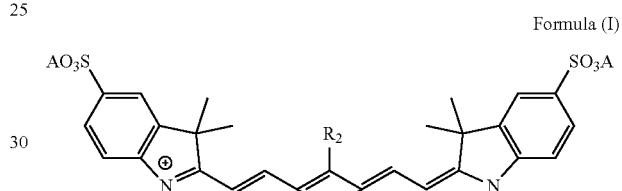

Formula (I)

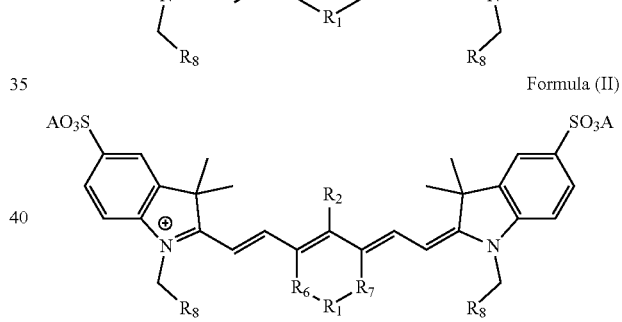

Formula (II)

Step 1

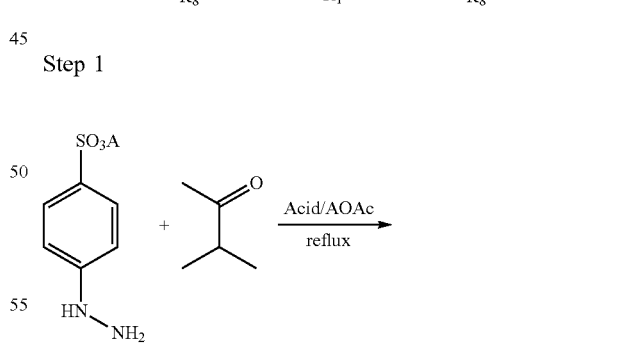

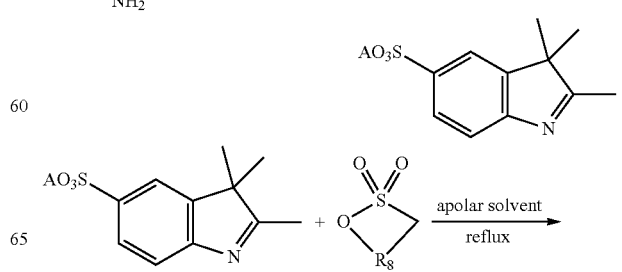

-continued

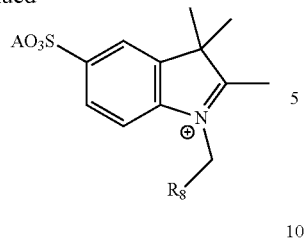

Step 1: A mixture of 4-hydrazinobenzenesulfonic salt or free acid, acetate salt, and 3-methyl-2-butanone in acid was heated under an inert atmosphere and a reduced pressure. The crude product was filtered, washed with requisite non-polar solvent, and collected after precipitation as a solid.

Step 2

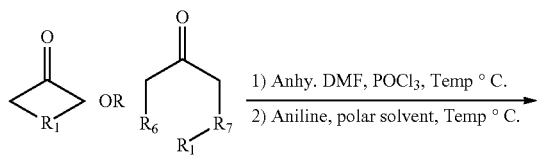

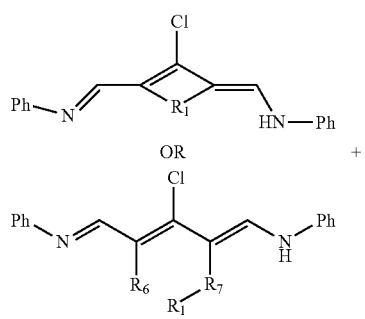

-continued

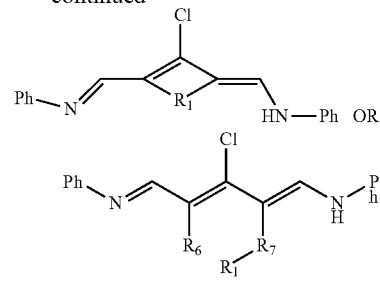

Step 2: To a salt or free acid of 2,3,3-trimethyl-3H-indole-5-sulfonic acid and acetate salt, requisite sultone in a non-polar solvent was added and stirred at proper temperature until consumption of 2,3,3-trimethyl-3H-indole-5-sulfonic acid. The reaction was cooled to room temperature and the solvent was decanted. Added suitable polar solvent to the gummy reaction mixture and stirred at room temperature, filtered the gummy solids to get crude 2,3,3-trimethyl-1-(4-sulfonatobutyl)-3H-indolium-sulfonate salt. The crude was dissolved in a suitable polar solvent to get clear solution. The solid was filtered and washed the bed with a suitable solvent and dried.

Step 3

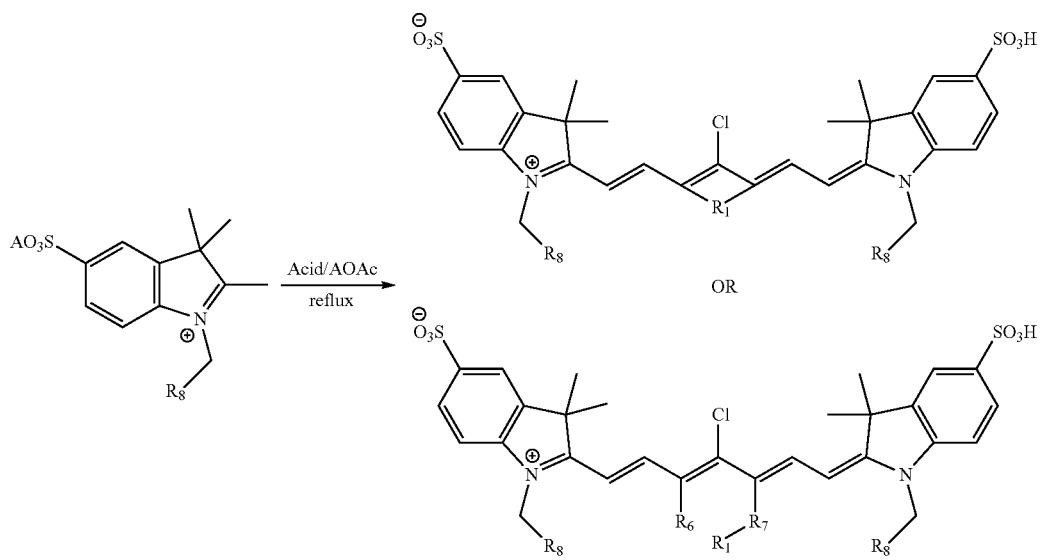

Step 3: Phosphorus oxychloride was added drop-wise to DMF with stirring at requisite temperature. After stirring, suitable cyclic ketone was added and the mixture was heated to reflux. The reaction was cooled to and with stirring, a mixture of aniline in a polar solvent was added drop-wise to the reaction mixture. The reaction was continued stirring at low temperature, and then the resulting crude product was poured into cooled aqueous acidic mixture. Crystals were allowed to form filtered, washed with cold solvents, and then dried to yield expected product.

Step 4

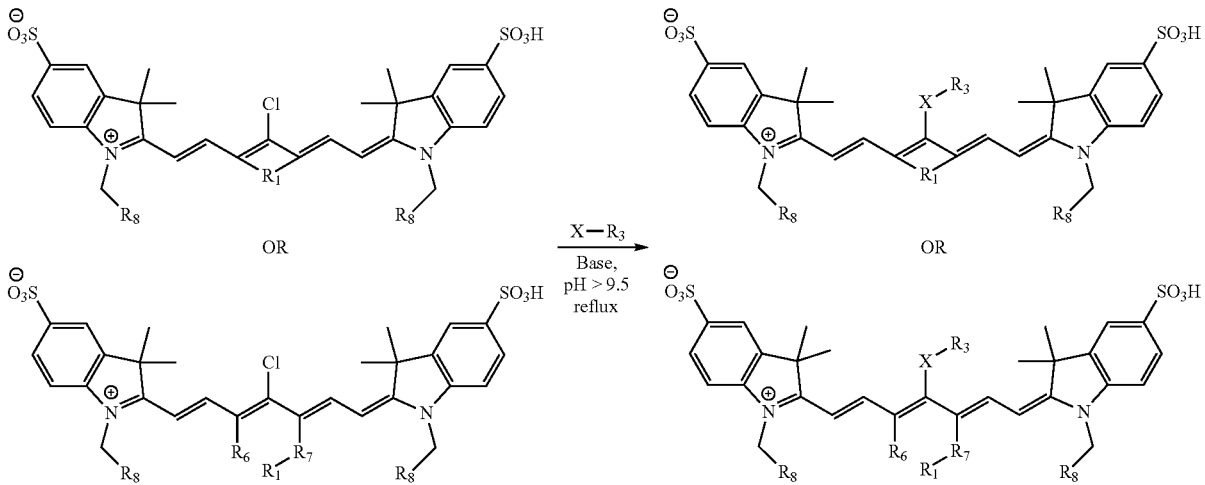

Step 4: To a X—R (whereas X=OH, NH2, SH, or SeH) in a polar solvent, pH is adjusted (>9.5) as needed using a freshly prepared solution of aqueous base by adding drop-wise. The reaction mixture was stirred at requisite temperature for requisite time. The product from step 3 was then dissolved in polar solvent (pH adjusted as needed) and added to the above reaction mixture. The reaction mixture was stirred at requisite temperature until consumption of the starting materials by monitoring with suitable detection methods such as LC/MS. The reaction mixture was cooled to suitable temperature and precipitate by nonpolar solvent or purified by chromatographic methods or crystallization methods.

Step 5

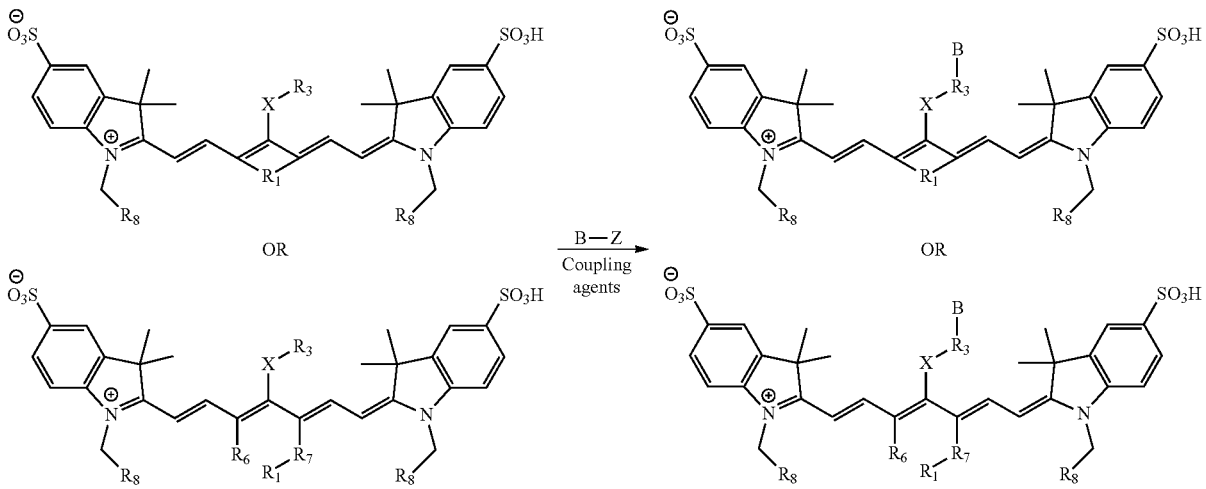

B = Lignad-Linker, whereas Ligand can be antibody, small molecule, aptamer, protein, peptide, etc
Z = COOH, NH$_2$, SH, or OH Step 5: To a product from step 4 in polar solvent, appropriated coupling reagents were added followed by addition of B—Z (B=Ligand-linker, Ligand=antibody, small molecule, aptamer, protein, peptide, etc., and Z=COOH, NH$_2$, OH, or SH) and base. The reaction mixture was stirred at requisite temperature until consumption of the starting materials by monitoring with suitable detection methods such as LC/MS. The reaction mixture was precipitated by nonpolar solvent or purified by chromatographic methods or crystallization methods.

Preparation of sodium 2,3,3-trimethyl-1-(4-sulfonatobutyl)-3H-indol-1-ium-5-sulfonate (105)

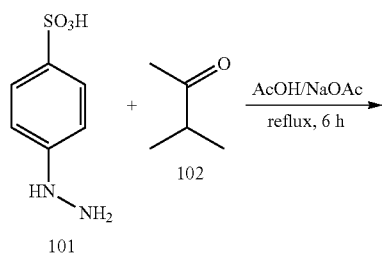

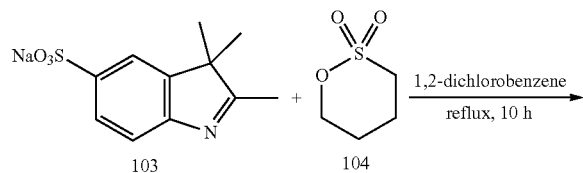

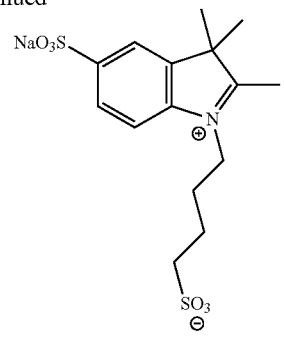

105

A mixture of 4-hydrazinobenzenesulfonic acid (6 g, 31.9 mmol, 1 equiv), NaOAc (5 g, 63.8 mmol, 2.0 equiv), and 3-methyl-2-butanone (8 g, 92.9 mmol, 2.95 equiv) in glacial acetic acid (36 mL) was heated at 130° C. under a nitrogen atmosphere in a sealed tube. The crude product was filtered, washed with methyl tert-butyl ether, and collected 103 after precipitation as a brown solid (5 g, 98% purity); mp 292 to 293° C.

To a solution of NaOAc salt of 103 (25.0 g, 1.0 eq), Butane sultone (2.0 eq) in 1,2-dichlorobenzene (10 vol) at 110° C. for 20 h and checked for consumption of 103 by LCMS. Added another 0.3 eq of Butane sultone and continued the reaction for another 24 h [IPC@48 h showed unreacted Step-1 ~8.83% by LCMS]. The reaction was cooled to room temperature and the solvent was decanted. Added IPA (10 vol) to the gummy reaction mixture and stirred at room temperature for 1-2 h, filtered the gummy solids to get 40.0 g of step-2 crude. The crude was dissolved in MeOH (80 mL) to get clear solution further added a prepared solution of IPA:DCM (160 mL:160 mL) and stirred for 1-2 h. The solids were filtered and washed the bed with IPA:DCM (20 mL:20 mL) mixture and suck dry. The solid was dried under vacuum below 50° C. to get 23.0 g (58%) of 105 as pink color powder with 96.3% purity by LCMS Preparation of 106-110

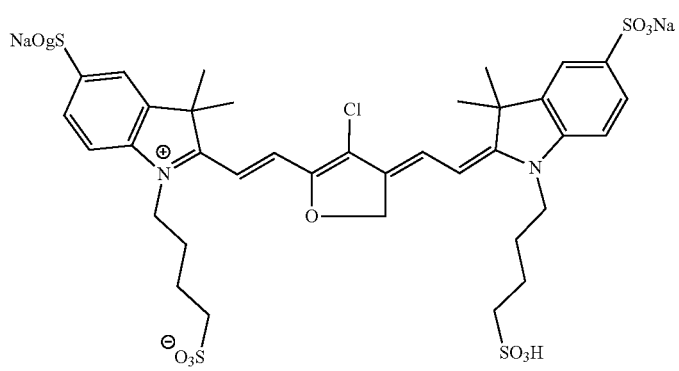

106

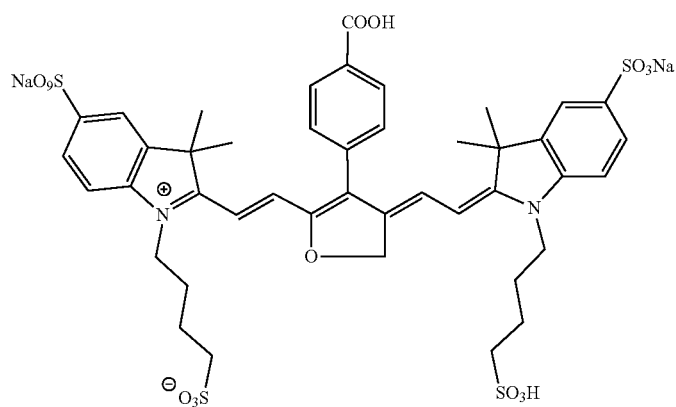
107
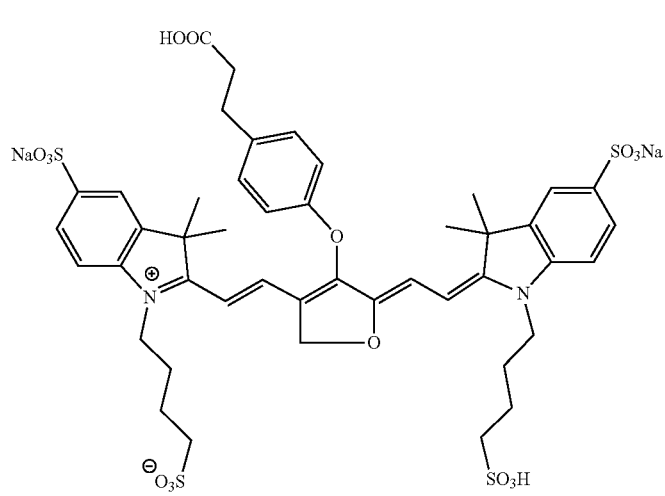
108
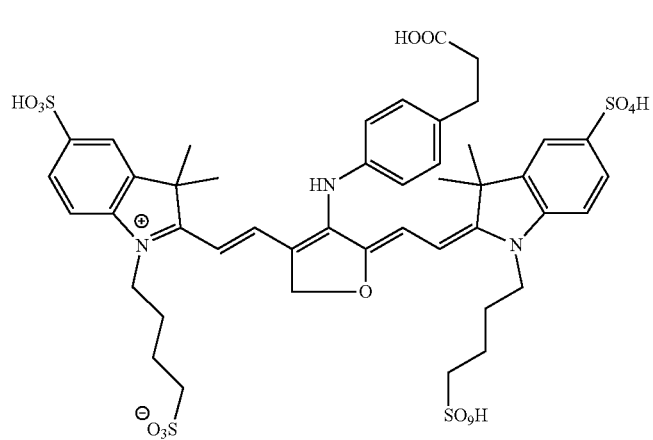
109

-continued

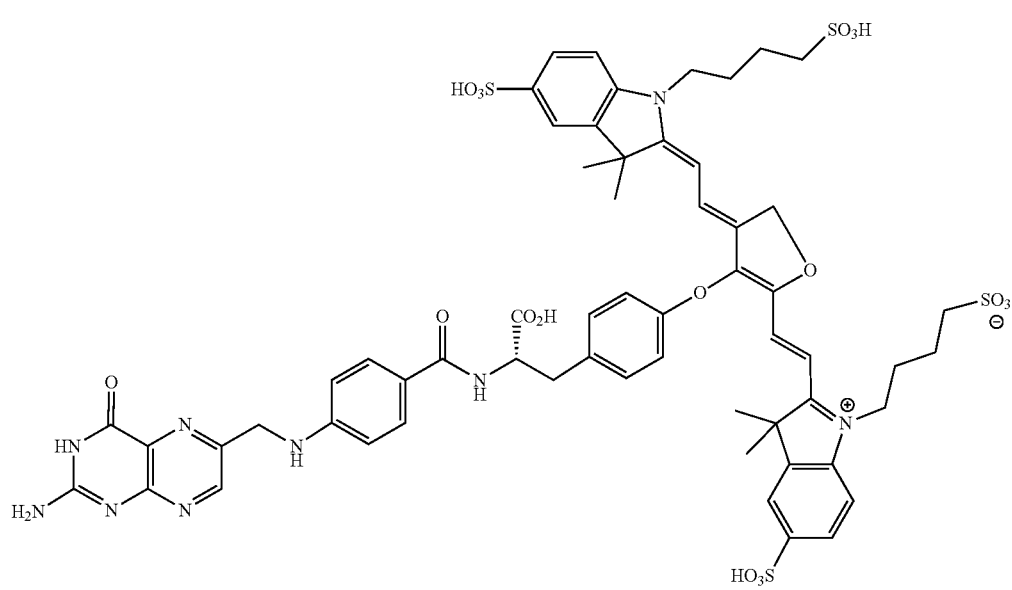

Preparation of N—((E)-(4-chloro-5-((E)-(phe-nylimino)methyl)furan-3(2H)-ylidene)methyl)aniline (112)

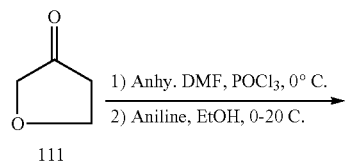

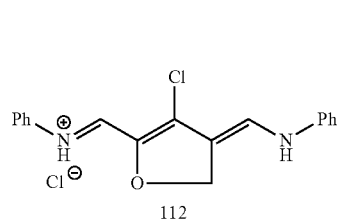

Phosphorus oxychloride (1.73 ml, 18.60 mmol) was added dropwise from a pressure equalizing funnel to anhydrous DMF (2 ml, 2 mmol) with stirring at 0° C. After 30 min, cyclohexanone (0.2 g ml, 2.32 mmol) was added and the mixture was heated under reflux for 2.5 h. The reaction was cooled to 25° C. and with stirring, a mixture of aniline/EtOH [1:1 (v/v), 4 ml] was added dropwise to the reaction mixture. The reaction was continued for 30 min at 25° C. with vigorous stirring, and then the deep purple mixture was poured into ice cooled $H_2O/HCl$ [10:1 (v/v), 10 ml]. Crystals were allowed to form for 2 h in an ice bath. The reaction was filtered, washed with cold $H_2O$ and $Et_2O$, and then dried in vacuo. (520 mg, 60%) as a dark purple solid.

Preparation of Sodium 2-((E)-2-((E)-3-chloro-4-((E)-2-(3,3-dimethyl-1-(4-sulfobutyl)-5-sulfonatoin-dolin-2-ylidene)ethylidene)-4,5-dihydrofuran-2-yl)vinyl)-3,3-dimethyl-1-(4-sulfonatobutyl)-3H-indol-1-ium-5-sulfonate (106)

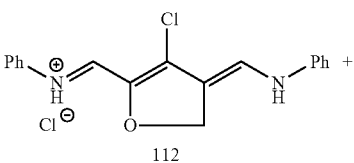

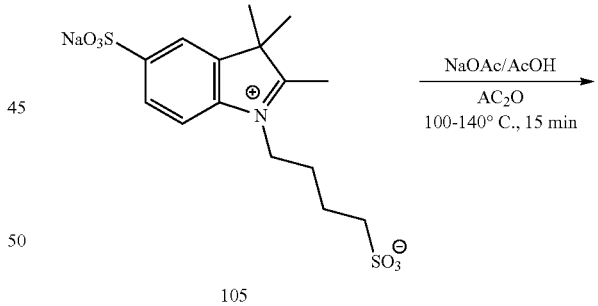

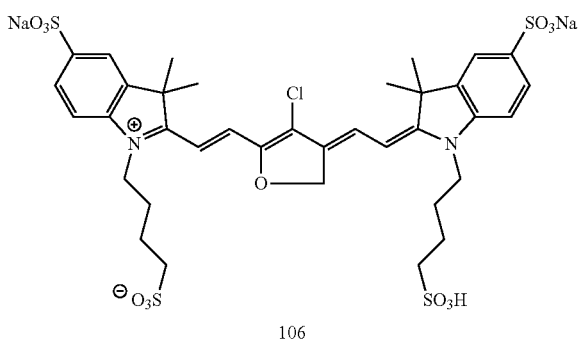

Acetic anhydride (0.5 mL) and acetic acid (0.5 mL) were added to the pressure vessel containing 113 (20 mg, 0.057 mmol, 1 equiv.), 105 (45 mg, 0.115 mmol, 2 equiv) and sodium acetate (4.72 mg, 0.057 mmol, 1 equiv). The reaction vessel was sealed and heated the content at 100° C. for 5 minutes and 140° C. for 10 minutes. The reaction mixture was added dropwise to acetone (20 mL) and the precipitated solid was filtered washed with acetone (5 mL) and dried on high vacuum to obtain 106 as a green solid which was purified by RP-HPLC.

Preparation of sodium 4-(2-((E)-2-((Z)-4-((4-(2-carboxyethyl)phenyl)amino)-5-(2-((E)-3,3-dimethyl-5-sulfo-1-(4-sulfobutyl)indolin-2-ylidene)ethylidene)-2,5-dihydrofuran-3-yl)vinyl)-3,3-dimethyl-5-sulfo-3H-indol-1-ium-1-yl)butane-1-sulfonate (108)

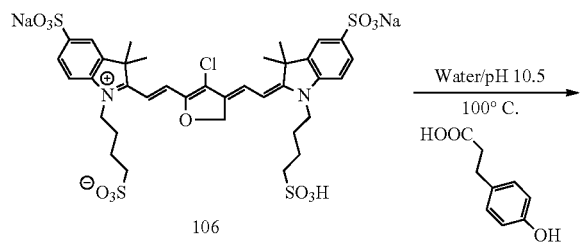

106

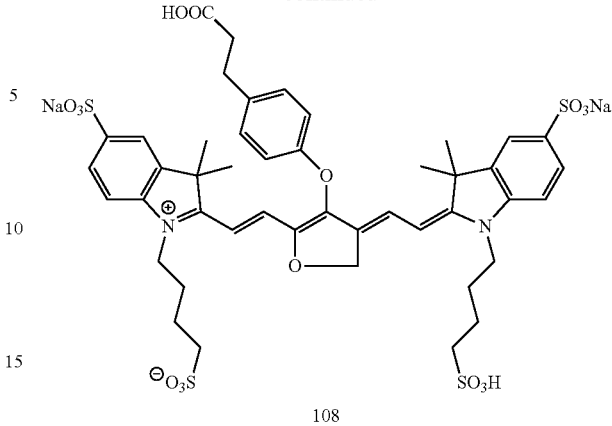

108

A 5 mL round bottom flask was charged with a stirring bar and 3-(4-hydroxyphenyl)propanoic acid (1 mg, 0.0057 mmol, 1 equiv), then water (0.4 mL) was added to give a yellow suspension [suspension A]. A freshly prepared solution of aqueous 1 M $Na_2CO_3$ (14 µL, 0.0.014 mmol, 2.5 equiv) was added dropwise to suspension A at 23° C., giving a dull yellow solution over 5 minutes [solution B]. The solution pH was 10.5 checked utilizing wet pH paper. 106 (5 mg, 0.0057 mmol, 1.0 equiv) was added to give an opaque green solution [solution C]. The flask containing Solution C was inserted in a 70° C. oil bath and was stirred for 2 h. The reaction was monitored by LC/MS. Formation of product was confirmed by LC/MS. The reaction mixture was cooled to rt and purified by RP-HPLC to obtain the product in 45% yield.

Preparation of 4-(2-((E)-2-((Z)-4-((4-(2-carboxyethyl)phenyl)amino)-5-(2-((E)-3,3-dimethyl-5-sulfo-1-(4-sulfobutyl)indolin-2-ylidene)ethylidene)-2,5-dihydrofuran-3-yl)vinyl)-3,3-dimethyl-5-sulfo-3H-indol-1-ium-1-yl)butane-1-sulfonate (109)

Compound 109 was synthesized following a similar procedure as 108

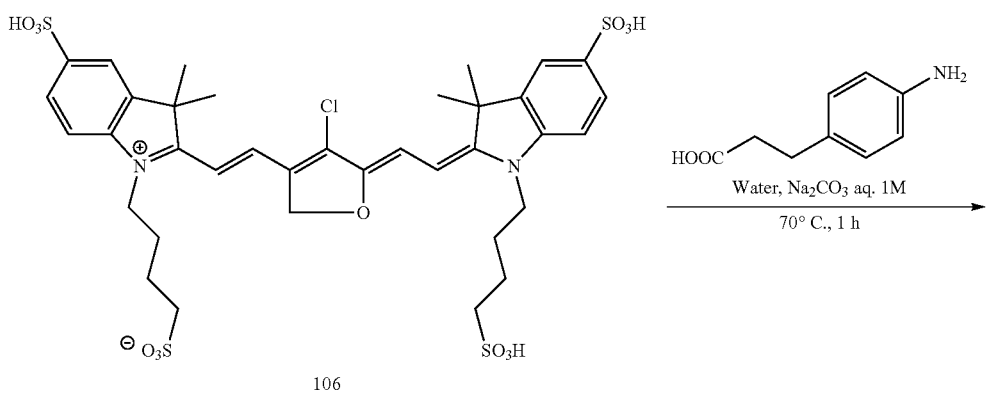

106

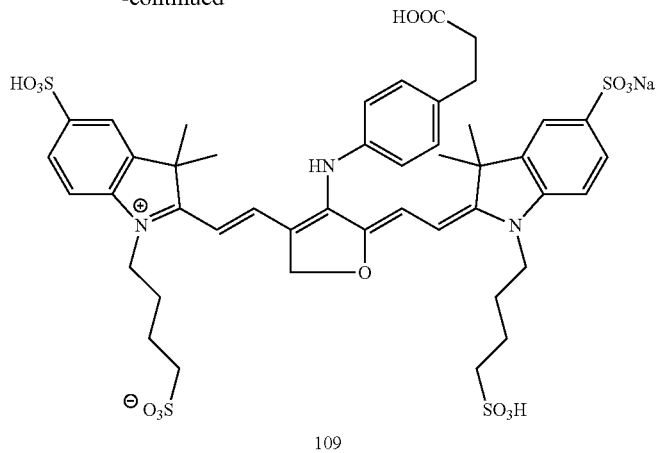
109
Preparation of 4-(2-((E)-2-((E)-3-(4-((S)-2-(4-(((2-amino-4-oxo-3,4-dihydropteridin-6-yl)methyl)amino)benzamido)-2-carboxyethyl)phenoxy)-4-((E)-2-(3,3-dimethyl-5-sulfo-1-(4-sulfobutyl)indolin-2-ylidene)ethylidene)-4,5-dihydrofuran-2-yl)vinyl)-3,3-dimethyl-5-sulfo-3H-indol-1-ium-1-yl)butane-1-sulfonate (110)
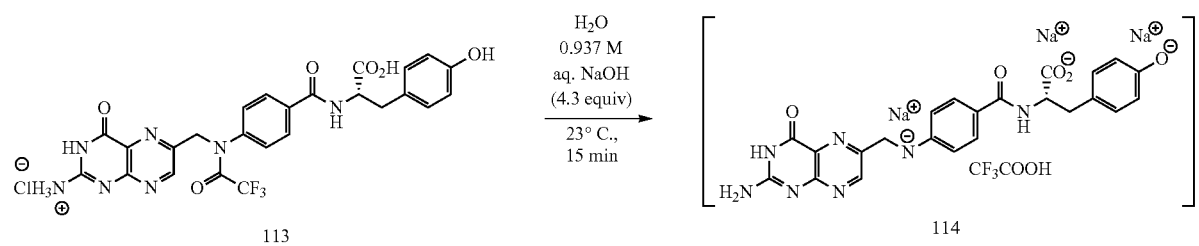
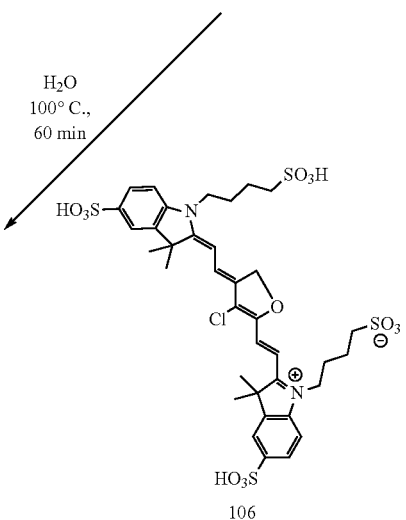

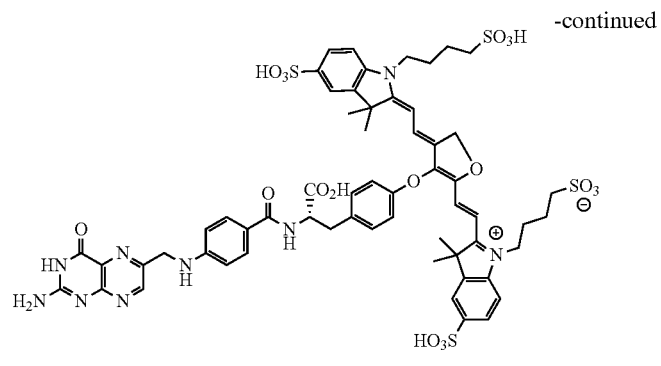

110

A 2 mL round bottom flask was charged with a stirring bar and 113 (3.47 mg, 0.057 mmol, 1 equiv), then water (0.1 mL) was added to give a yellow suspension [suspension A]. A freshly prepared solution of aqueous 0.1 M NaOH (24.5 µL, 0.0245 mmol, 4.30 equiv) was added dropwise to suspension A at 23° C., giving a dull yellow solution over 5 minutes [solution B]. Trianion (114) formation was confirmed by LC/MS showing m/z 572→m/z 476 while the solution pH was 9-10 utilizing wet pH paper. A 2 mL round bottom flask was charged with a stirring bar and 106 (5 mg, 0.057 mmol, 1 equiv), then water (0.2 mL) was added to give an opaque green solution [solution C]. The flask containing Solution C was inserted in a 105° C. oil bath and was stirred for 15 minutes, then solution B was added dropwise over 5 minutes. The system was fit with a condenser and was stirred for 1 hour. The reaction was monitored by LC/MS. Formation of 109 was confirmed by LC/MS. The reaction mixture was cooled to room temperature then was transferred via cannula as a steady stream to a stirred acetone (20 mL) to give green precipitate. The precipitated 113 was filtered under aspirator vacuum on sintered funnel washed with acetone (3×5 mL). The green powdery solid was dried under high vacuum to obtain 110 which was purified by RP-HPLC.

Preparation of 115-118

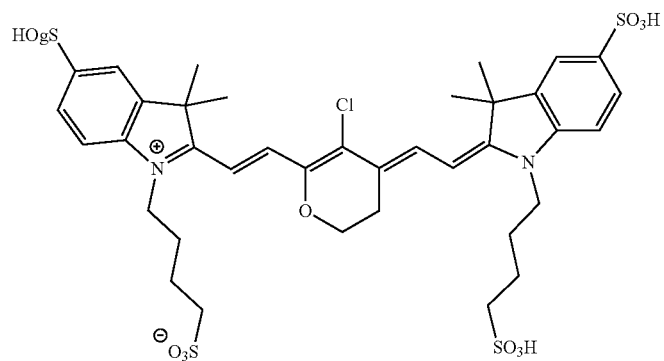

115

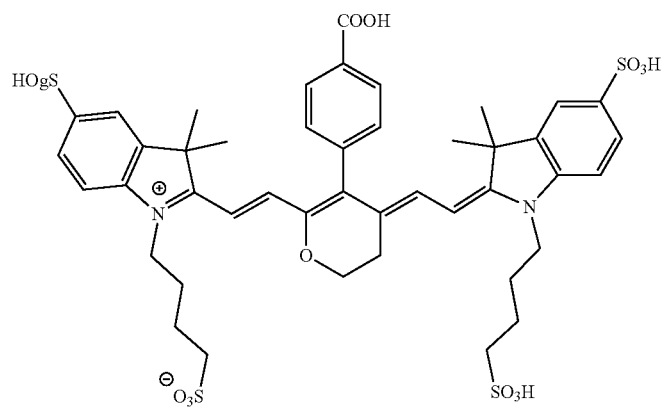

116

117
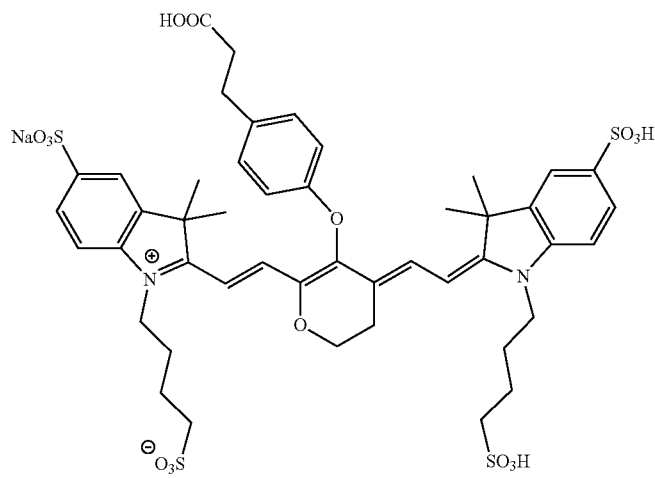
118
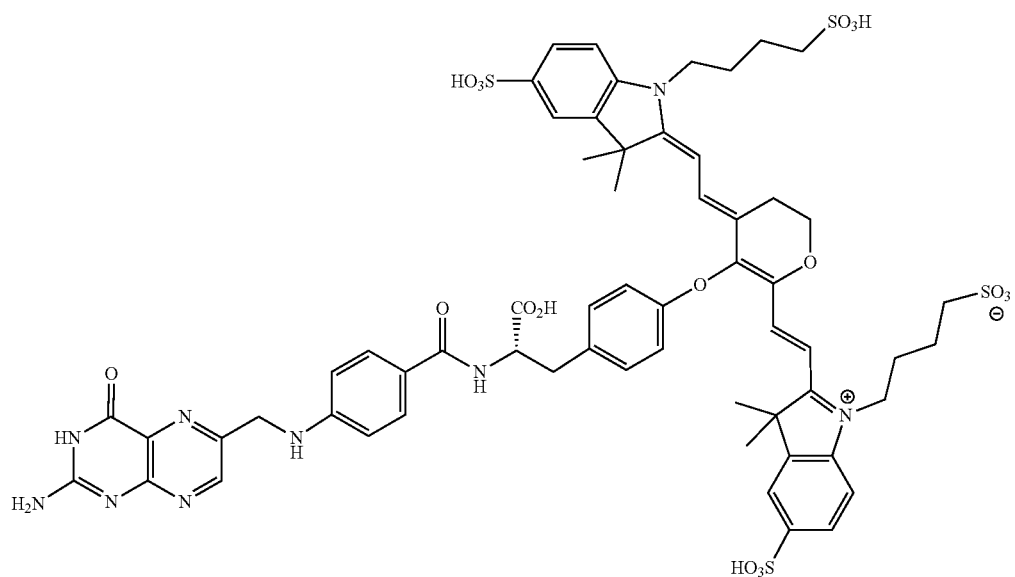
Preparation of Sodium 2-((E)-2-((E)-5-chloro-4-((E)-2-(3,3-dimethyl-1-(4-sulfobutyl)-5-sulfonatoindolin-2-ylidene)ethylidene)-3,4-dihydro-2H-pyran-6-yl)vinyl)-3,3-dimethyl-1-(4-sulfonatobutyl)-3H-indol-1-ium-5-sulfonate (115)
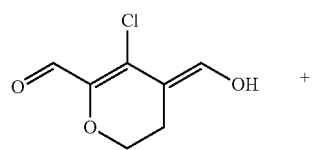
119
-continued
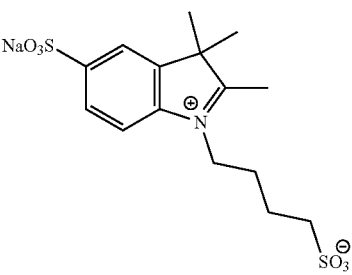
105
Toluene/n-BuOH
Reflux, 12 h -continued

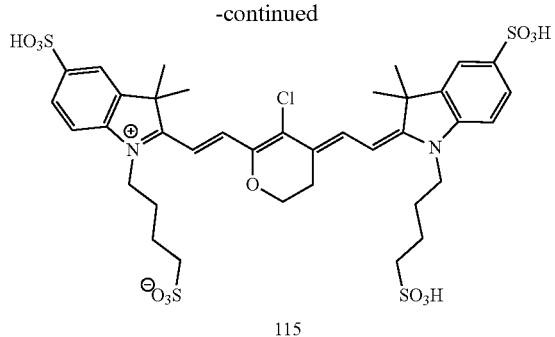

115

To a solution of 119 (476 mg, 2.739 mmol, 1 equiv) in toluene (30 mL) and n-butanol (10 mL) was added to a 100 mL round bottom flask fitted with Dean-Stark apparatus followed by addition of 105 (2.17 g, 5.479 mmol, 2 equiv) and refluxed the content for 20 h. The reaction mixture was concentrated and the dark green residue was washed with ether (2×30 mL) and dried under high vacuum to obtain 115 (1.52 g) in 60% crude yield. This was further purified by RP-HPLC.

Preparation of 4-(2-((E)-2-((E)-5-(4-carboxyphenoxy)-4-((E)-2-(3,3-dimethyl-5-sulfo-1-(4-sulfobutyl)indolin-2-ylidene)ethylidene)-3,4-dihydro-2H-pyran-6-yl)vinyl)-3,3-dimethyl-5-sulfo-3H-indol-1-ium-1-yl)butane-1-sulfonate (116)

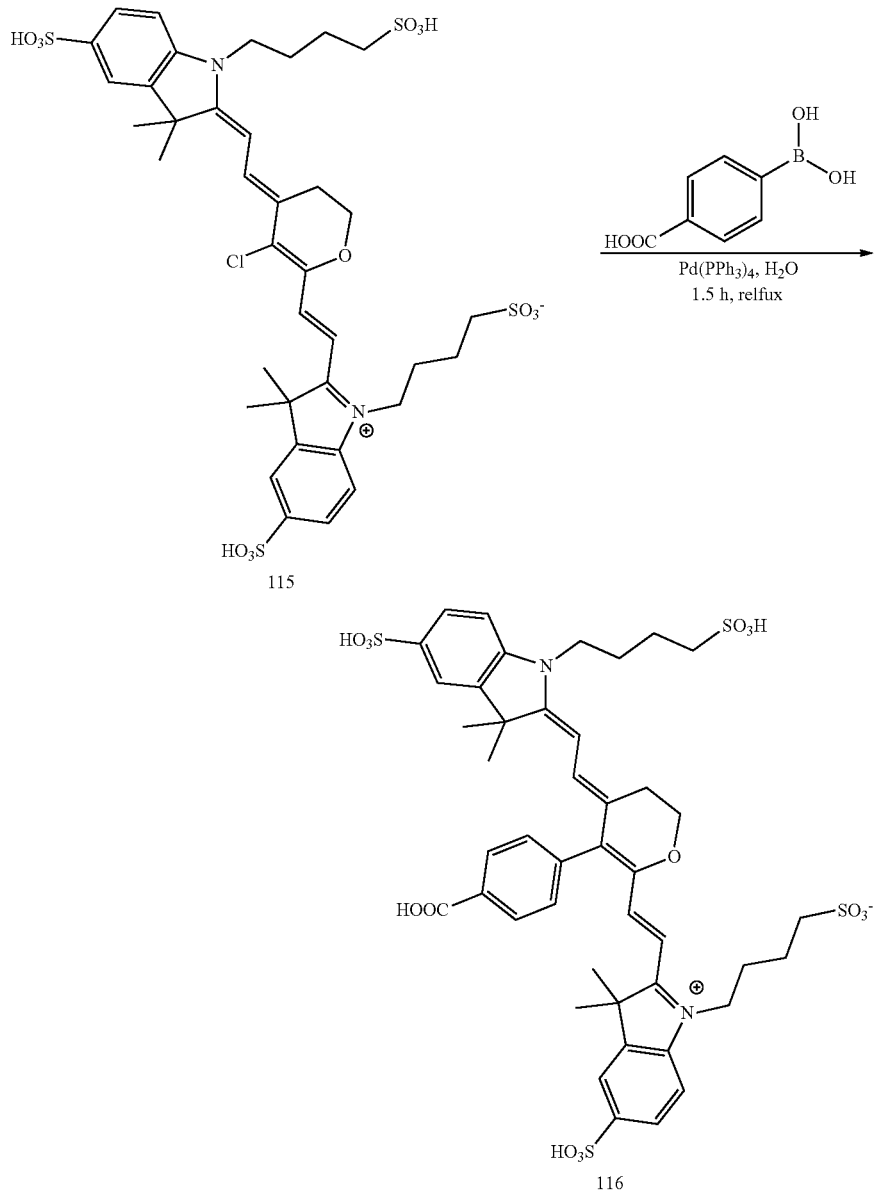

Water (1 mL) was added to the pressure vessel containing 115 (10 mg, 0.011 mmol, 1 equiv.), 120 (2.79 mg, 0.017 mmol, 1.5 equiv) and Pd(PPh$_3$)$_3$ (1.2 mg, 0.0011 mmol, 0.1 equiv). The reaction vessel was sealed and refluxed the content for 1.5 hours. After completion the reaction mixture was diluted with water 4 mL and filtered through celite and purified by RP-HPLC to obtain 116 as a green solid.

Preparation of 4-(2-((E)-2-((E)-5-(4-(2-carboxy-ethyl)phenoxy)-4-(2-((E)-3,3-dimethyl-5-sulfo-1-(4-sulfobutyl)indolin-2-ylidene)ethylidene)-3,4-di-hydro-2H-pyran-6-yl)vinyl)-3,3-dimethyl-5-sulfo-3H-indol-1-ium-1-yl)butane-1-sulfonate (117)

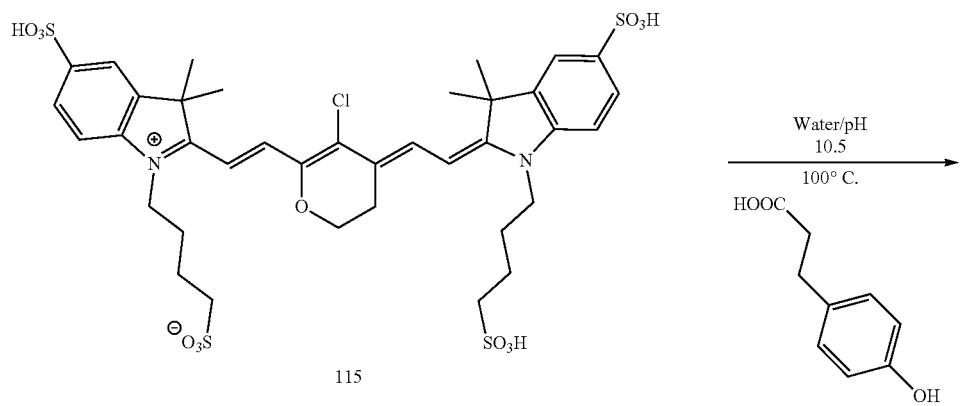

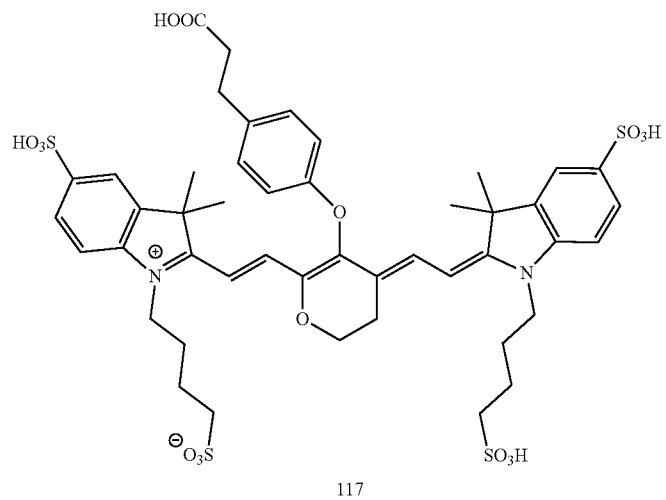

Preparation of Sodium (S)-2-(4-(((2-amino-4-oxo-3,4-dihydropteridin-6-yl)methyl)amino)benzamido)-3-(4-(((E)-4-((E)-2-(3,3-dimethyl-5-sulfo-1-(4-sulfobutyl)indolin-2-ylidene)ethylidene)-6-((E)-2-(3,3-dimethyl-5-sulfo-1-(4-sulfonatobutyl)-3H-indol-1-ium-2-yl)vinyl)-3,4-dihydro-2H-pyran-5-yl)oxy)phenyl)propanoate (118)

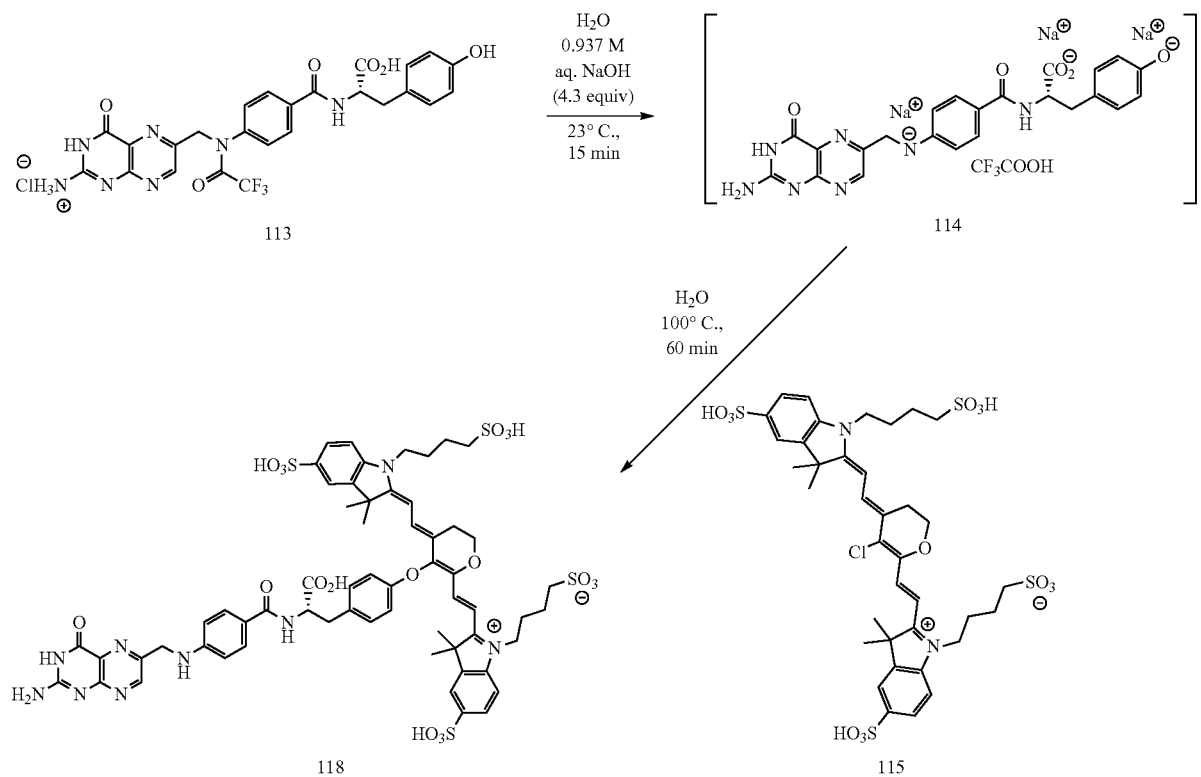

A 5 mL round bottom flask was charged with a stirring bar and 113 (6.83 mg, 0.011 mmol, 1 equiv), then water (0.4 mL) was added to give a yellow suspension [suspension A]. A freshly prepared solution of aqueous 0.937 M NaOH (51 µL, 0.051 mmol, 4.30 equiv) was added dropwise to suspension A at 23° C., giving a dull yellow solution over 5 minutes [solution B]. Trianion (114) formation was confirmed by LC/MS showing m/z 572→m/z 476 while the solution pH was 9-10 utilizing wet pH paper. A 5 mL round bottom flask was charged with a stirring bar and 108 (9.5 mg, 0.0107 mmol, 0.950 equiv), then water (0.8 mL) was added to give an opaque green solution [solution C]. The flask containing Solution C was inserted in a 105° C. oil bath and was stirred for 15 minutes, then solution B was added dropwise over 5 minutes. The system was fit with a condenser and was stirred for 1 hour. The reaction was monitored by LC/MS. Formation of 118 was confirmed by LC/MS. The reaction mixture was cooled to room temperature then was transferred via cannula as a steady stream to a stirred acetone (20 mL) to give green precipitate. The precipitated 118 was filtered under aspirator vacuum on sintered funnel washed with acetone (3×5 mL). The green powdery solid was dried under high vacuum for 12 h to obtain 118 which was purified by RP-HPLC.

Preparation of 120-123
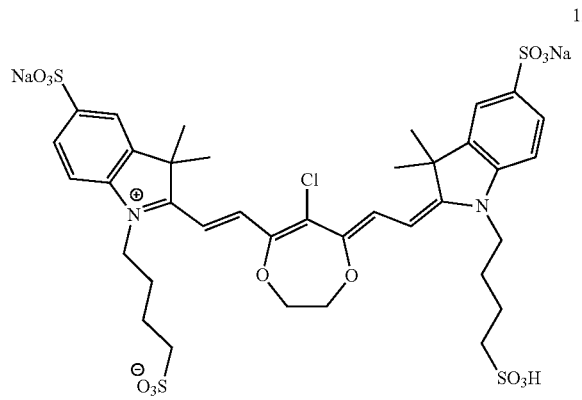
120
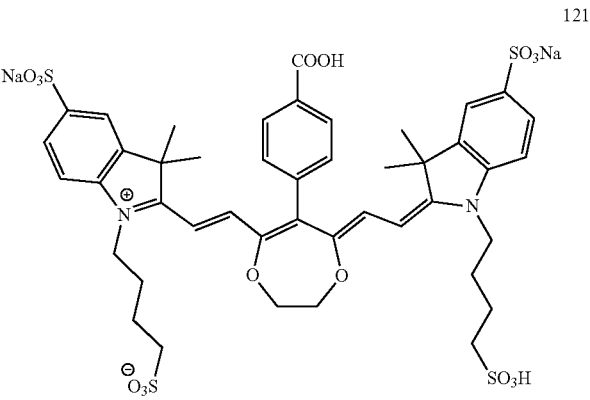
121
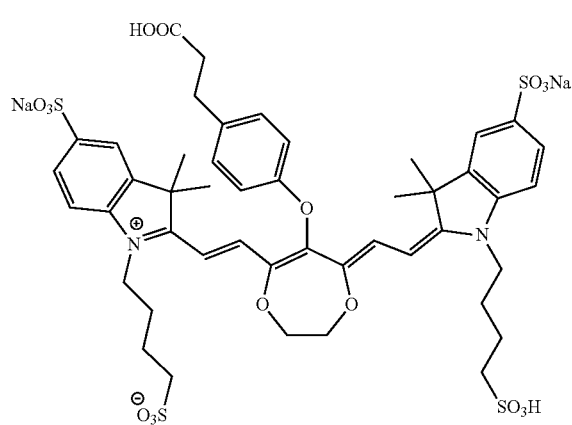
122
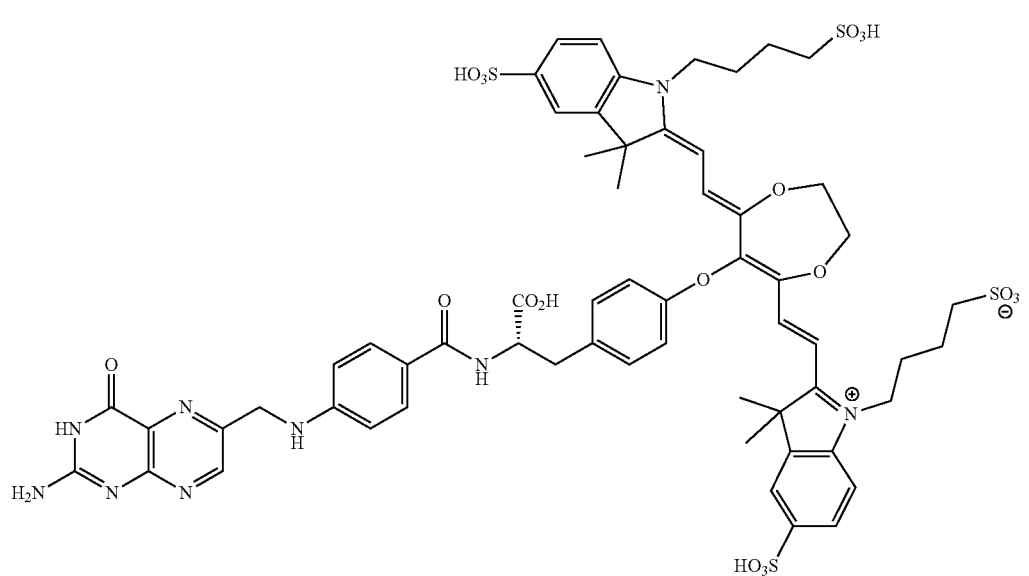
123

Preparation of Sodium 2-((E)-2-((Z)-6-chloro-7-((E)-2-(3,3-dimethyl-1-(4-sulfobutyl)-5-sulfonatoindolin-2-ylidene)ethylidene)-3,7-dihydro-2H-1,4-dioxepin-5-yl)vinyl)-3,3-dimethyl-1-(4-sulfonatobutyl)-3H-indol-1-ium-5-sulfonate (120)

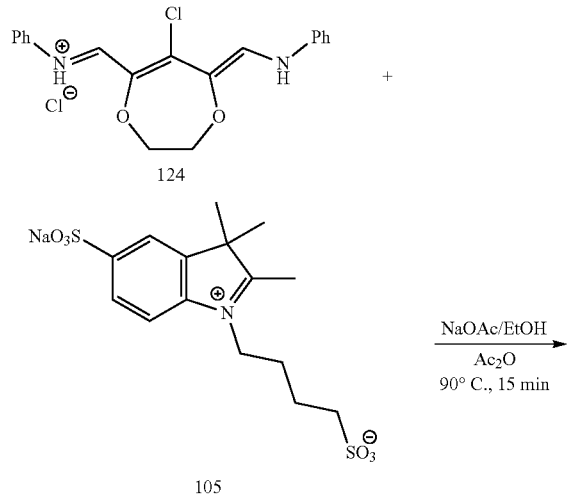

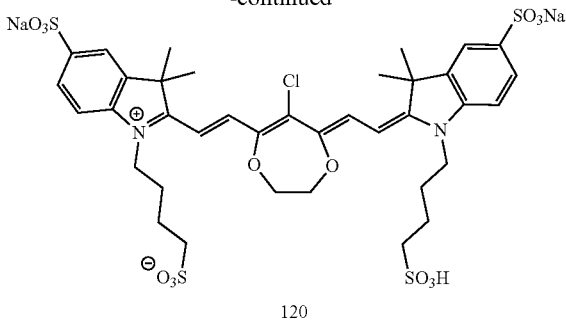

Acetic anhydride (1 mL) and ethanol (10 mL) were added to the pressure vessel containing 124 (130 mg, 0.344 mmol, 1 equiv.), 105 (273 mg, 0.689 mmol, 2 equiv) and sodium acetate (62 mg, 0.756 mmol, 2.2 equiv). The reaction vessel was sealed and heated the content at 90° C. for 15 minutes. The reaction mixture was added dropwise to acetone (20 mL) and the precipitated solid was filtered washed with acetone (5 mL) and dried on high vacuum to obtain 120 as a green solid which was purified by RP-HPLC.

Preparation of sodium 4-(2-((E)-2-((Z)-6-(4-(2-carboxyethyl)phenoxy)-5-(2-((E)-3,3-dimethyl-5-sulfo-1-(4-sulfobutyl)indolin-2-ylidene)ethylidene)-2,3-dihydro-5H-1,4-dioxepin-7-yl)vinyl)-3,3-dimethyl-5-sulfo-3H-indol-1-ium-1-yl)butane-1-sulfonate (122)

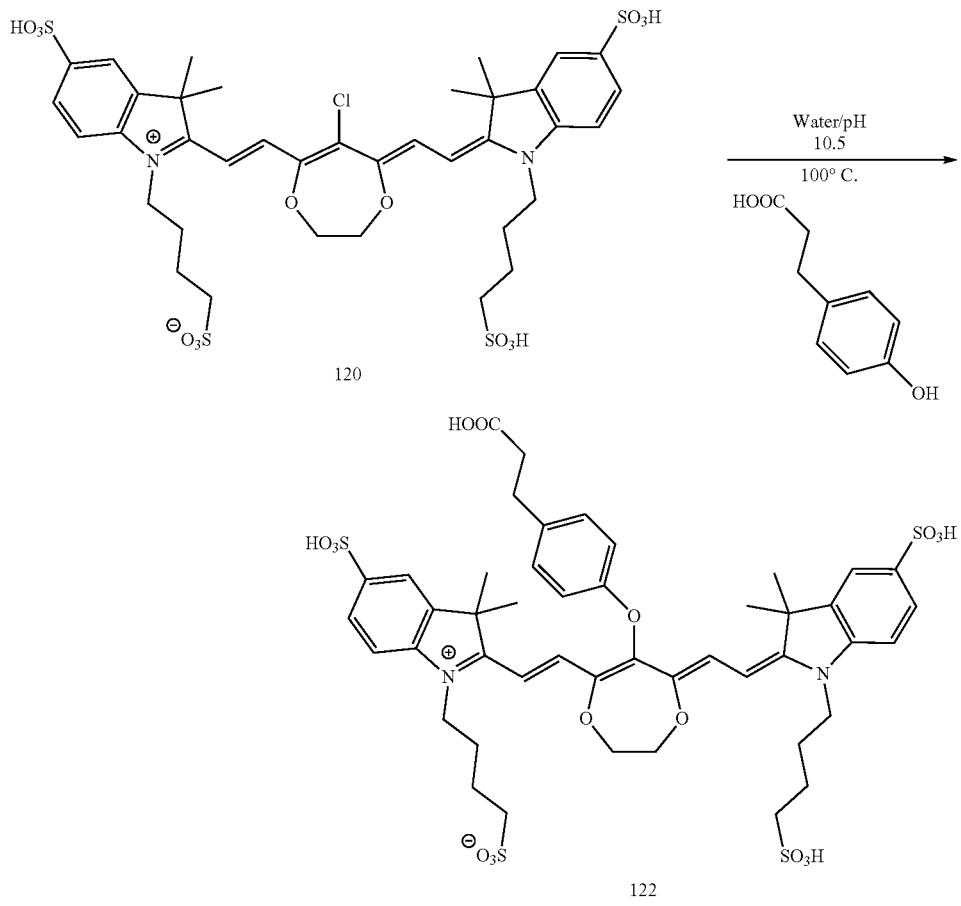

Preparation of 125-132
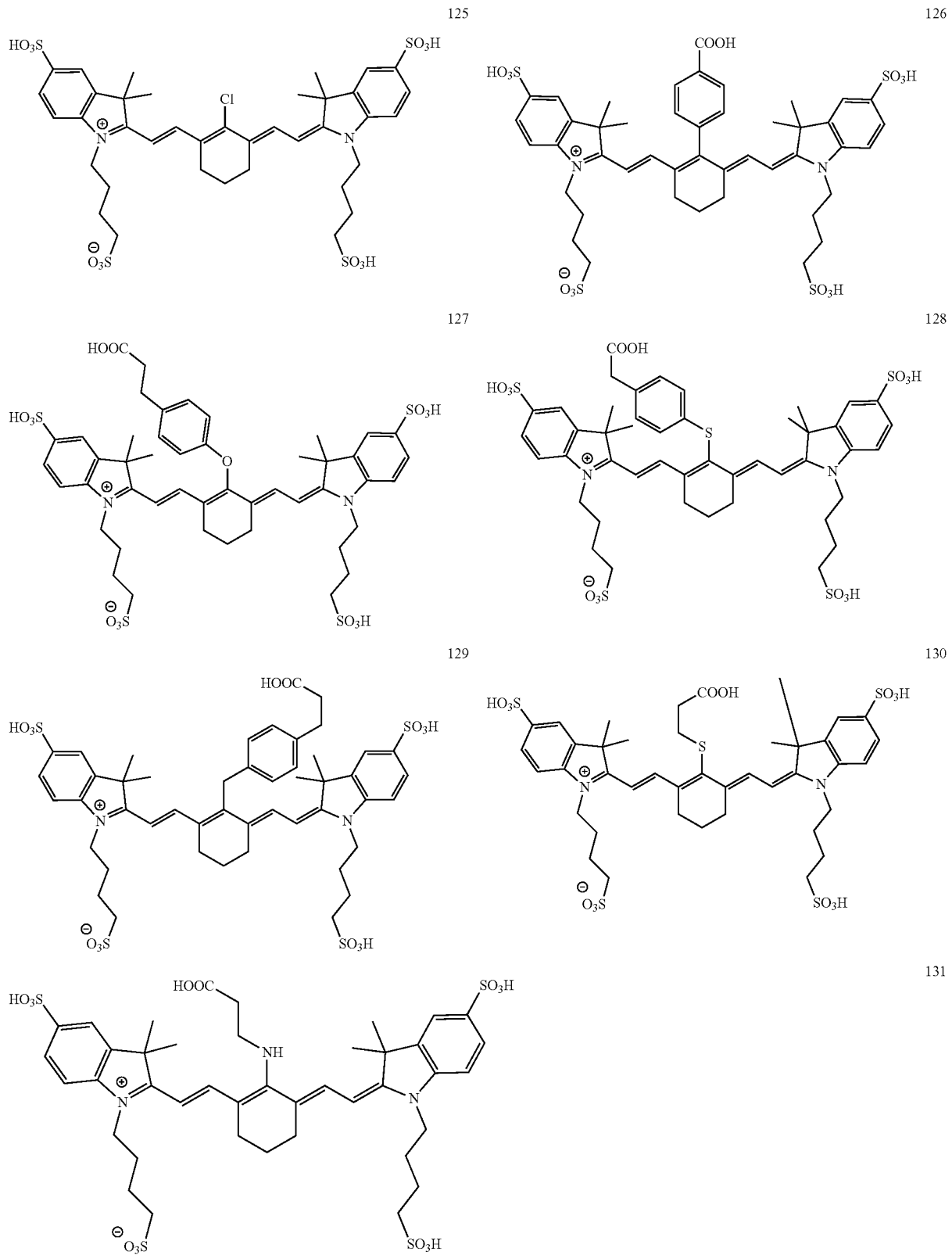

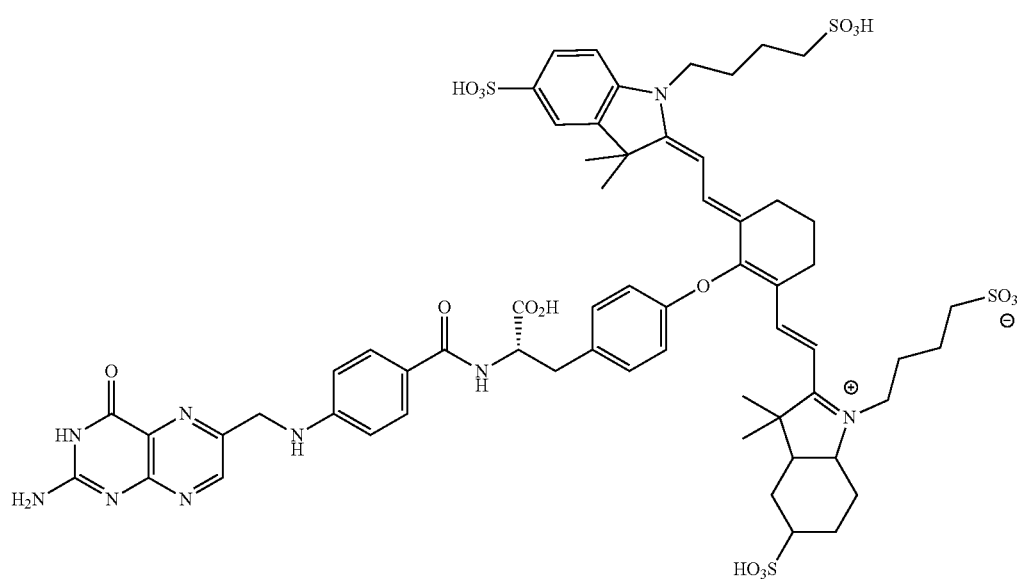

132

Preparation of sodium 2-((E)-2-((E)-2-chloro-3-(2-((E)-3,3-dimethyl-5-sulfonato-1-(4-sulfonatobutyl)indolin-2-ylidene)ethylidene)cyclohex-1-en-1-yl)vinyl)-3,3-dimethyl-1-(4-sulfonatobutyl)-3H-indol-1-ium-5-sulfonate (125)

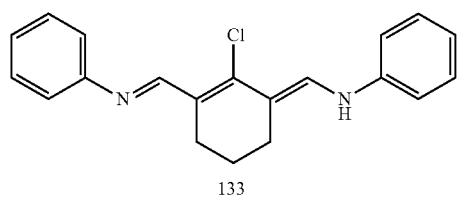

133

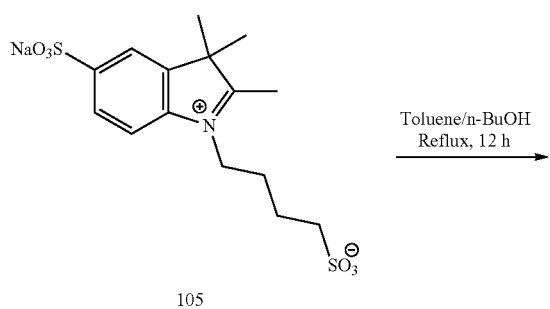

105

Toluene/n-BuOH
Reflux, 12 h
→

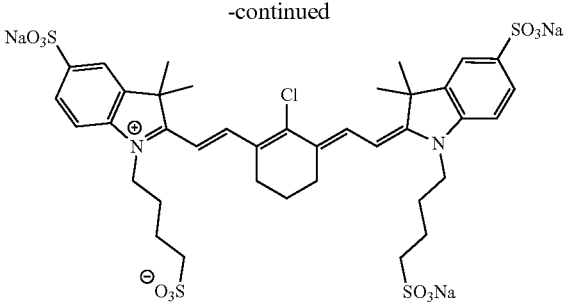

125

To a 1 L vessel add 200 mL of Ethanol, add 16 g of 133, 37.17 g of the indole (105), and 7.3 g of sodium acetate. Slowly add 13.62 g of Acetic Anhydride. Heat the mixture to reflux (~78° C.) and stir for 5 hours. Add 150 mL of demineralized water while maintaining the temperature at >70° C. Stir the solution for 30 minutes at reflux. Filter the hot solution through glass fiber. Add the solution to a clean 1 L vessel and heat to reflux for 30 minutes. Cool to 15° C. and hold for 1 hour. Collect on a buchner funnel. Wash the cake with a solution of 100 mL of Ethanol and 75 ml of water. Wash cake with 175 mL of Ethanol and draw down for 1 hour. Add the damp cake back to a 1 L vessel followed by 200 mL of IPA. Stir the mixture at room temperature for 1 hour. Filter the solid on a lap funnel. Dry the product in a vacuum oven at 100° C. at full at 26 in for 12 hours. Dry the product in a vacuum oven at 100° C. at full at 26 in for 12 hours. Yield=25.4 gr. (60%); LC=98.6 A % (270 nm)

Preparation of 4-(2-((E)-2-((E)-4'-carboxy-6-(2-((E)-3,3-dimethyl-5-sulfo-1-(4-sulfobutyl)indolin-2-ylidene)ethylidene)-3,4,5,6-tetrahydro-[1,1'-biphenyl]-2-yl)vinyl)-3,3-dimethyl-5-sulfo-3H-indol-1-ium-1-yl)butane-1-sulfonate (126)

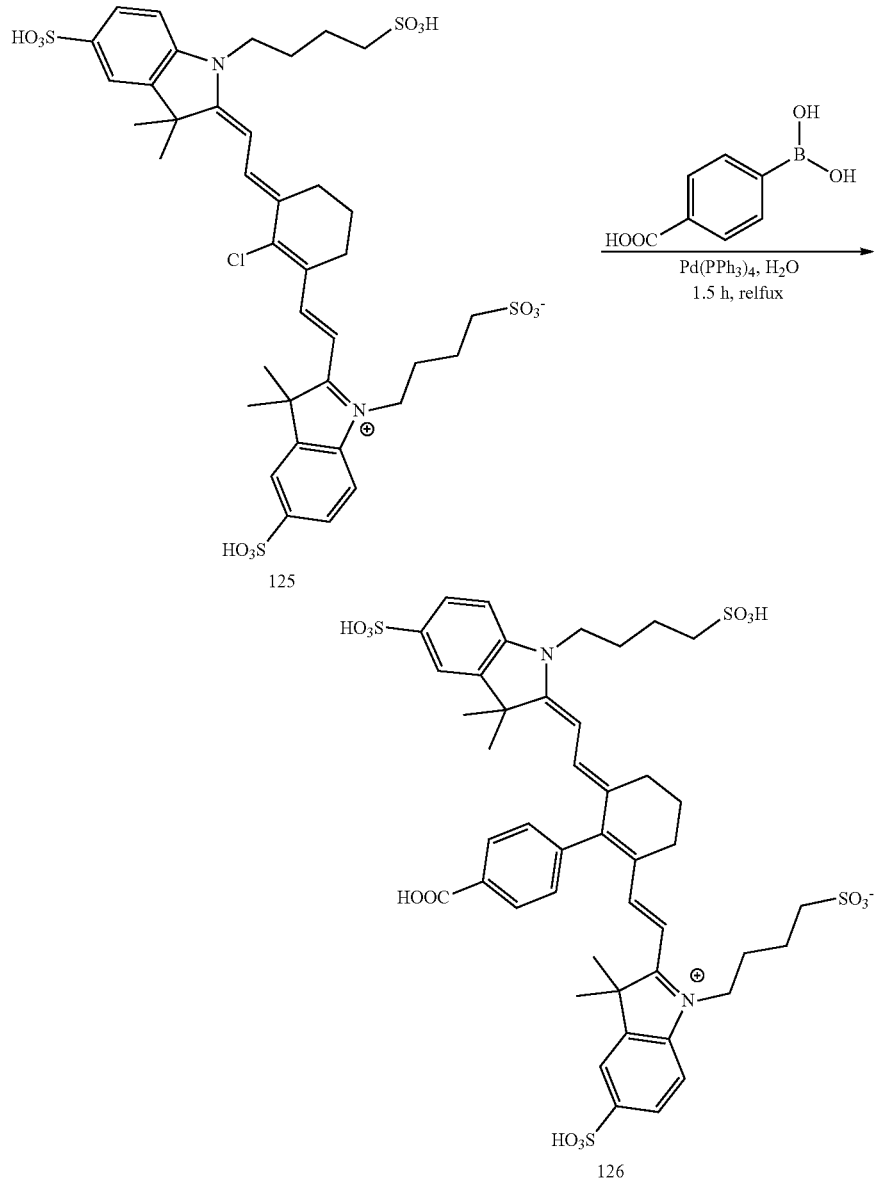

Water (1 mL) was added to the pressure vessel containing 125 (10 mg, 0.011 mmol, 1 equiv.), 120 (2.79 mg, 0.017 mmol, 1.5 equiv) and Pd(PPh$_3$)$_3$ (1.2 mg, 0.0011 mmol, 0.1 equiv). The reaction vessel was sealed and refluxed the content for 1.5 hours. After completion the reaction mixture was diluted with water 4 mL and filtered through celite and purified by RP-HPLC to obtain 126 as a green solid.

Preparation of 4-(2-((E)-2-((E)-2-(4-(2-carboxy-ethyl)phenoxy)-3-(2-((E)-3,3-dimethyl-5-sulfo-1-(4-sulfobutyl)indolin-2-ylidene)ethylidene)cyclohex-1-en-1-yl)vinyl)-3,3-dimethyl-5-sulfo-3H-indol-1-ium-1-yl)butane-1-sulfonate (127)

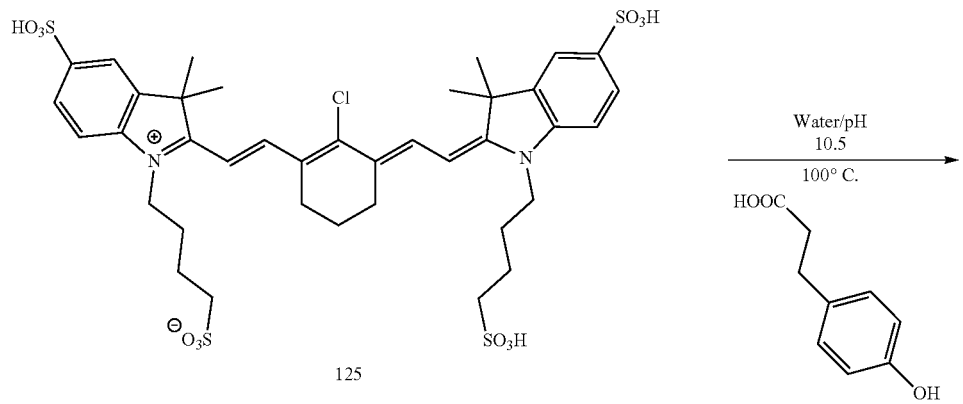

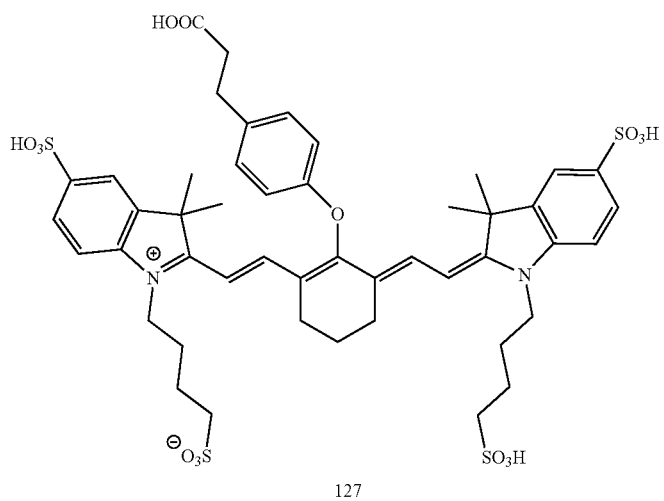

A 5 mL round bottom flask was charged with a stirring bar and 3-(4-hydroxyphenyl)propanoic acid (35 mg, 0.209 mmol, 1 equiv), then water (2 mL) was added to give a yellow suspension [suspension A]. A freshly prepared solution of aqueous 1 M NaOH (522 μL, 0.522 mmol, 2.5 equiv) was added dropwise to suspension A at 23° C., giving a dull yellow solution over 5 minutes [solution B]. The solution pH was 10 utilizing wet pH paper. 125 (200 mg, 0.209 mmol, 1.0 equiv) was added to give an opaque green solution [solution C]. The flask containing Solution C was inserted in a 70° C. oil bath and was stirred for 1 h. The reaction was monitored by LC/MS. Formation of product was confirmed by LC/MS. The reaction mixture was cooled to rt and purified by RP-HPLC to obtain the product in 60% yield.

Preparation of 4-(2-((E)-2-((E)-2-((4-(carboxymethyl)phenyl)thio)-3-(2-((E)-3,3-dimethyl-5-sulfo-1-(4-sulfobutyl)indolin-2-ylidene)ethylidene)cyclohex-1-en-1-yl)vinyl)-3,3-dimethyl-5-sulfo-3H-indol-1-ium-1-yl)butane-1-sulfonate (128)
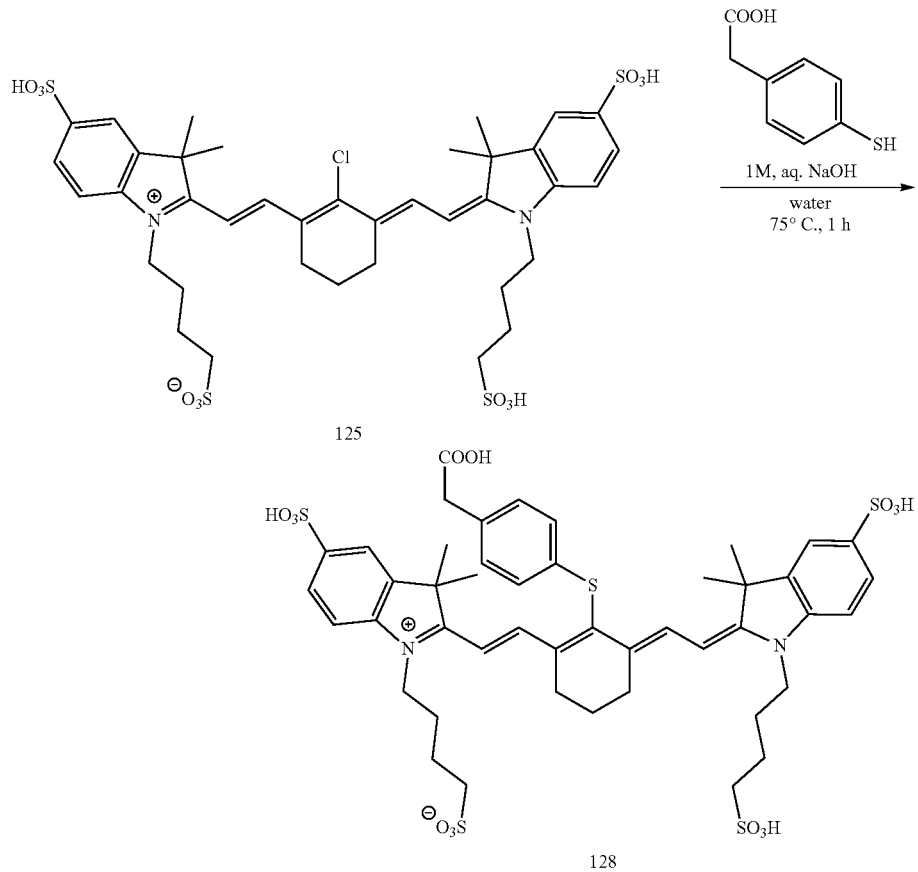
Preparation of 4-(2-((E)-2-((E)-2-((4-(2-carboxyethyl)phenyl)amino)-3-(2-((E)-3,3-dimethyl-5-sulfo-1-(4-sulfobutyl)indolin-2-ylidene)ethylidene)cyclohex-1-en-1-yl)vinyl)-3,3-dimethyl-5-sulfo-3H-indol-1-ium-1-yl)butane-1-sulfonate (129)
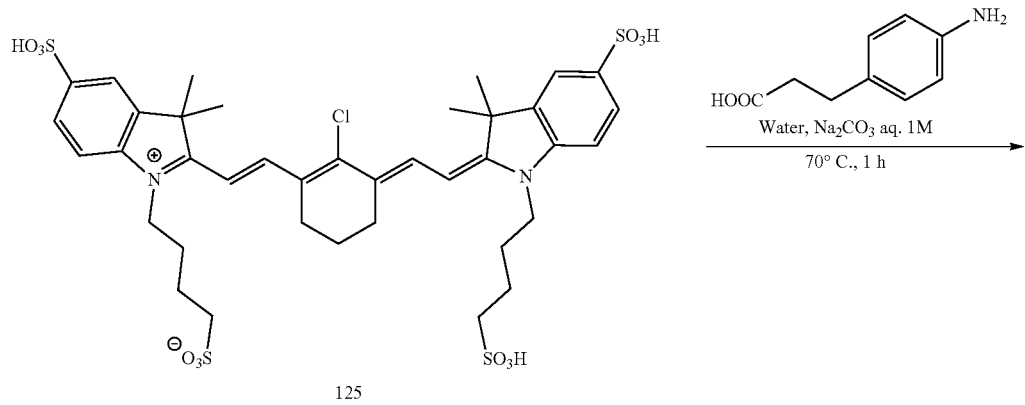

-continued
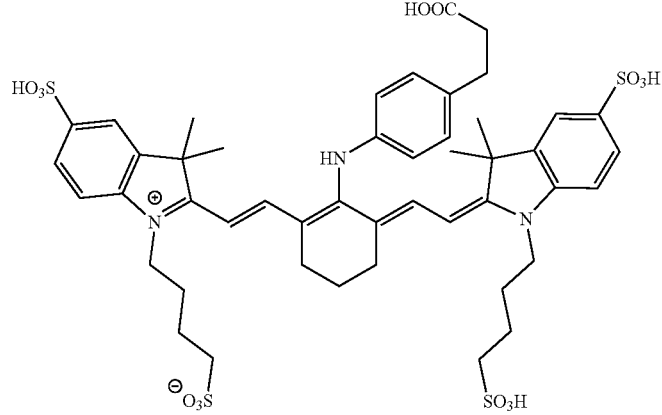
129
Preparation of 4-(2-((E)-2-((E)-2-((2-carboxyethyl)thio)-3-(2-((E)-3,3-dimethyl-5-sulfo-1-(4-sulfobutyl)indolin-2-ylidene)ethylidene)cyclohex-1-en-1-yl)vinyl)-3,3-dimethyl-5-sulfo-3H-indol-1-ium-1-yl)butane-1-sulfonate (130)
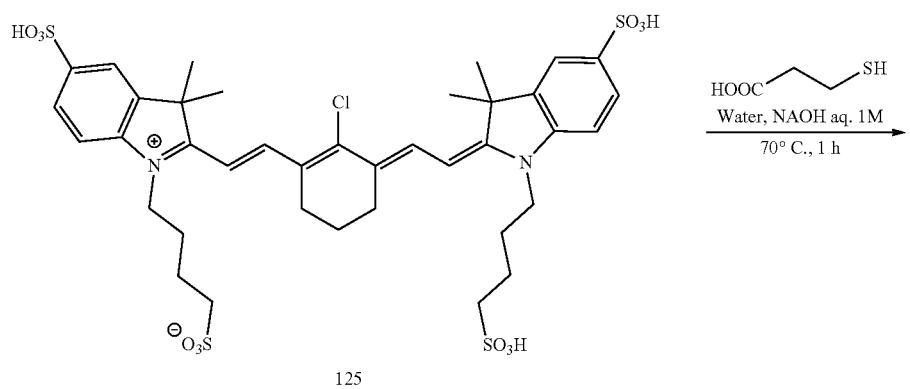
125
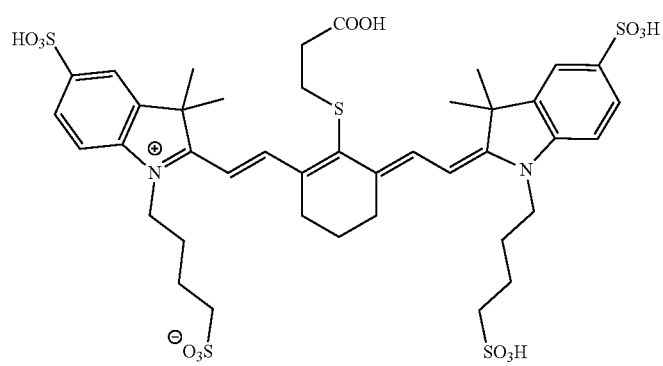
130

Preparation of 4-(2-((E)-2-((E)-2-((2-carboxyethyl)amino)-3-(2-((E)-3,3-dimethyl-5-sulfo-1-(4-sulfobutyl)indolin-2-ylidene)ethylidene)cyclohex-1-en-1-yl)vinyl)-3,3-dimethyl-5-sulfo-3H-indol-1-ium-1-yl)butane-1-sulfonate (131)
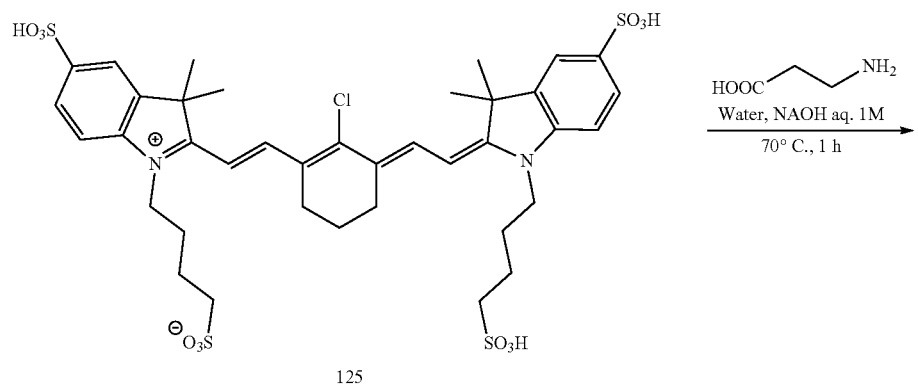
125
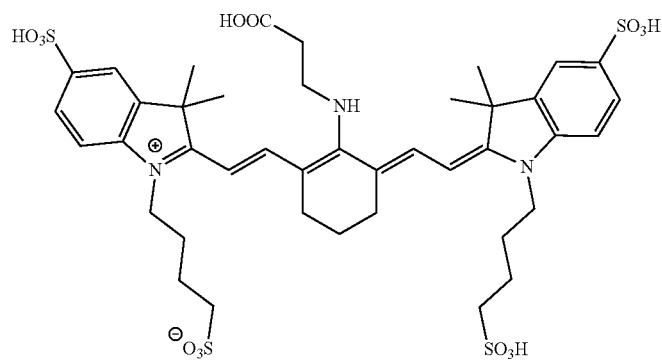
131

Preparation of Sodium (S)-2-(4-(((2-amino-4-oxo-3,
4-dihydropteridin-6-yl)methyl)amino)benzamido)-3-
(4-(((E)-4-((E)-2-(3,3-dimethyl-5-sulfo-1-(4-
sulfobutyl)indolin-2-ylidene)ethylidene)-6-((E)-2-(3,
3-dimethyl-5-sulfo-1-(4-sulfonatobutyl)-3H-indol-1-
ium-2-yl)vinyl)-3,4-dihydro-2H-pyran-5-yl)oxy)
phenyl)propanoate (132)

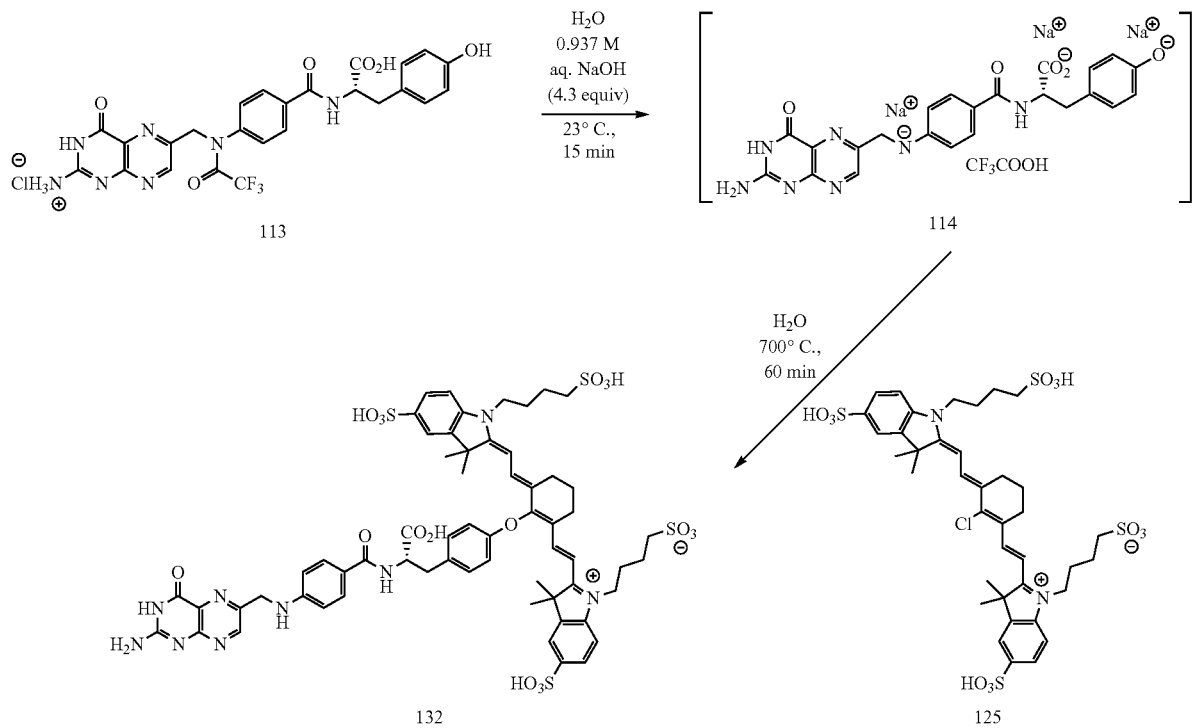

113 (13.85 g, 22.78 mmol, 1 equiv) was dissolved in water (95 mL) at 23° C. and pH of the solution was increased to ca 9.5 by adding aqueous 3.75 M NaOH (26.12 mL, 97.96 mmol, 4.30 equiv) dropwise to give a clear pale-yellow solution. Formation of trianion was monitored by observing TFA deprotected Pteroyl-Tyr using LC/MS (m/z 476) and pH of the solution was maintained at 9.5.

To a solution of 125 (20.63 g, 21.64 mmol, 0.950 equiv) was in water (180 mL) at 23° C., a solution of 114 at pH 9.5 was added dropwise. The temperature of the reaction mixture was increased to 75° C., stirred at 75° C. for 45 minutes, and monitored formation of 126 by LC/MS. Upon completion of product formation, the reaction mixture was cooled to room temperature and transferred via cannula as a steady stream to a stirred acetone (5.5 L) to give green precipitate. The precipitated was filtered under aspirator vacuum on sintered funnel washed with acetone (3×500 mL). The green powdery solid was dried under high vacuum for 12 h to obtain 132 (31 g) quantitatively. While purity of the precipitated 132 was 92.8%, the crude material was further purified using prep-HPLC. The purity of 132 at wavelength 270 nm was ≥98% and at wavelength 770 nm was ≥99%. The chiral purity of OTL38 at 770 nm was ≥98%. Analytical UPLC: Rt=2.33 min [solvent gradient: 0% B to 50% B in 5 min]. UV: 225, 275, 350 nm. 1H NMR (500 MHz, DMSO-d6/D20).

The examples that follow are merely provided for the purpose of illustrating particular embodiments of the disclosure and are not intended to be limiting to the scope of the appended claims. As discussed herein, particular features of the disclosed compounds and methods can be modified in various ways that are not necessary to the operability or advantages they provide. For example, the compounds can incorporate a variety of amino acids and amino acid derivatives as well as targeting ligands depending on the particular use for which the compound will be employed. One of skill in the art will appreciate that such modifications are encompassed within the scope of the appended claims.

Figure 7:
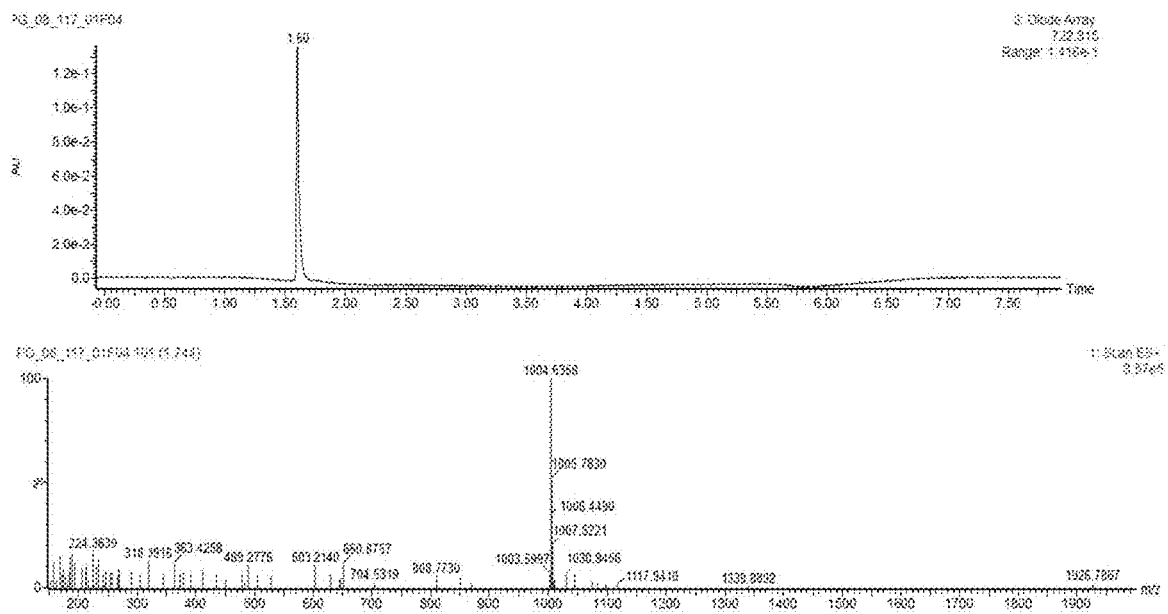
FIG. 7 Chromatogram profile of 109.
Figure 8:
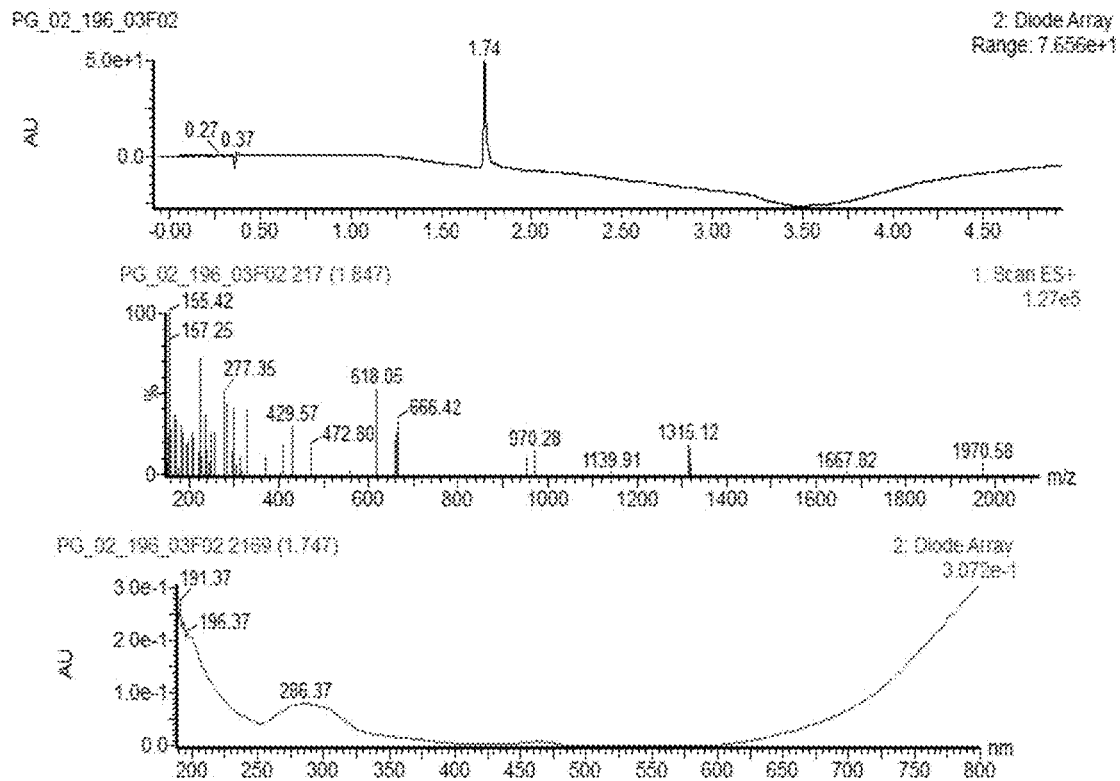
FIG. 8 Chromatogram profile of 110.
Figure 9:
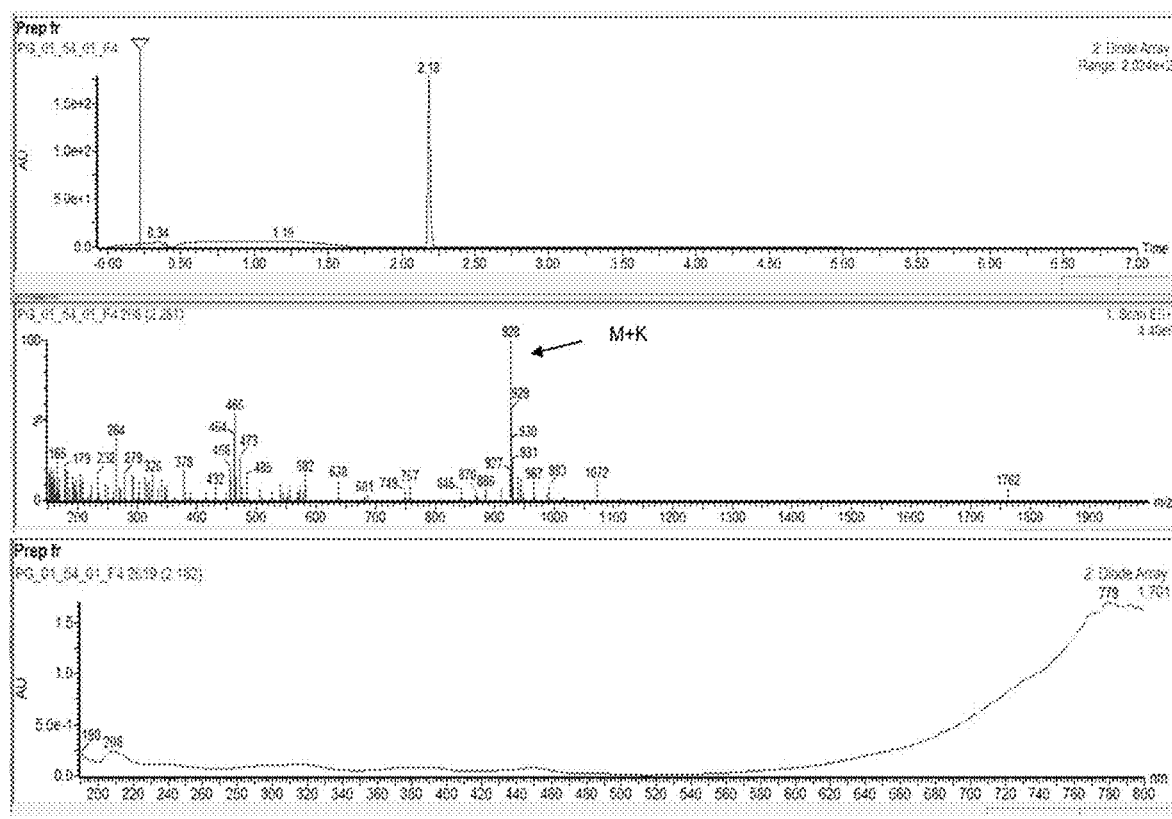
FIG. 9 Chromatogram profile of 115.
Figure 10:
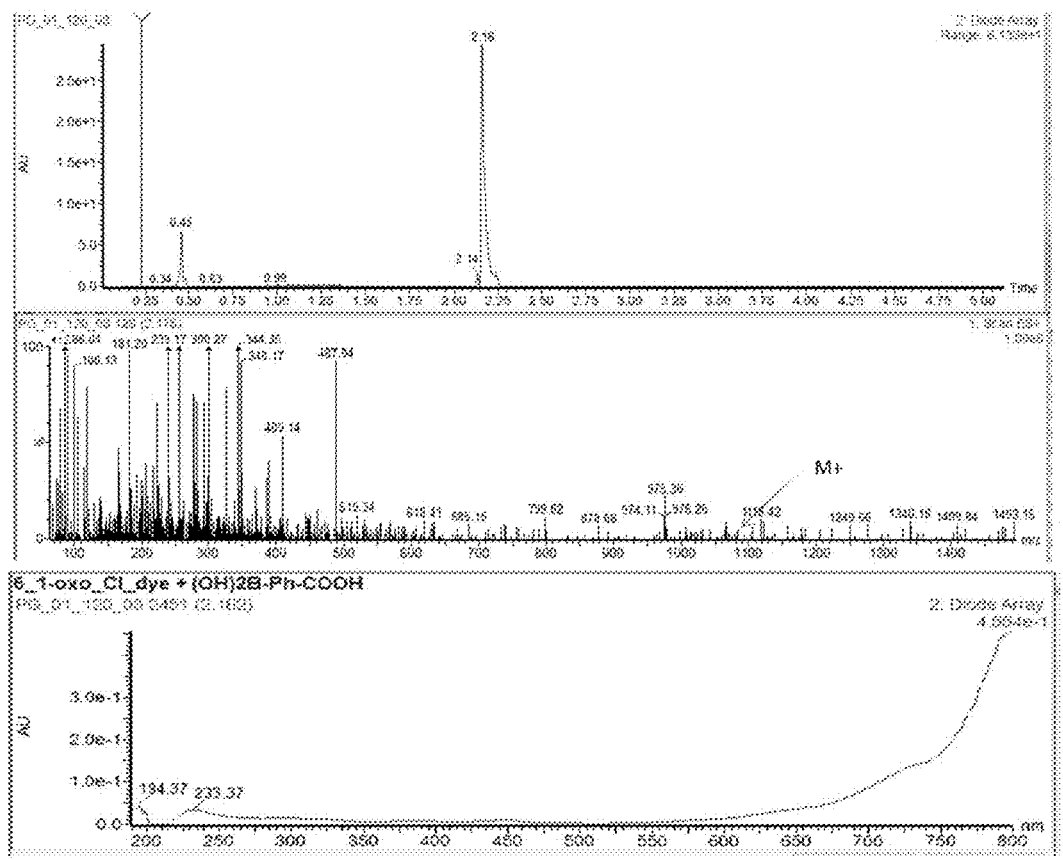
FIG. 10 Chromatogram profile of 116.
Figure 11:
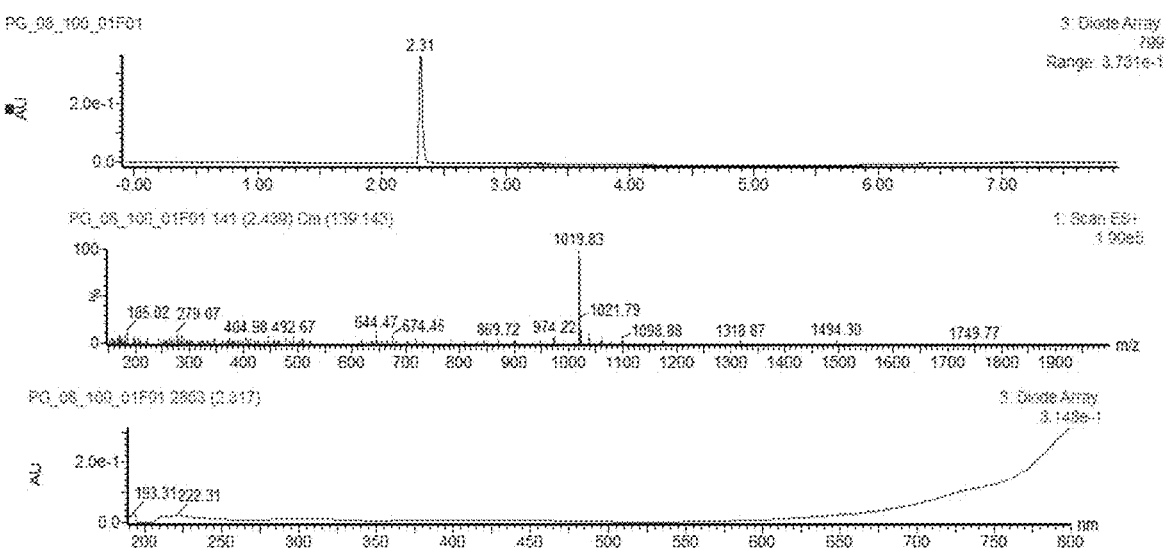
FIG. 11 Chromatogram profile of 117.
Figure 12:
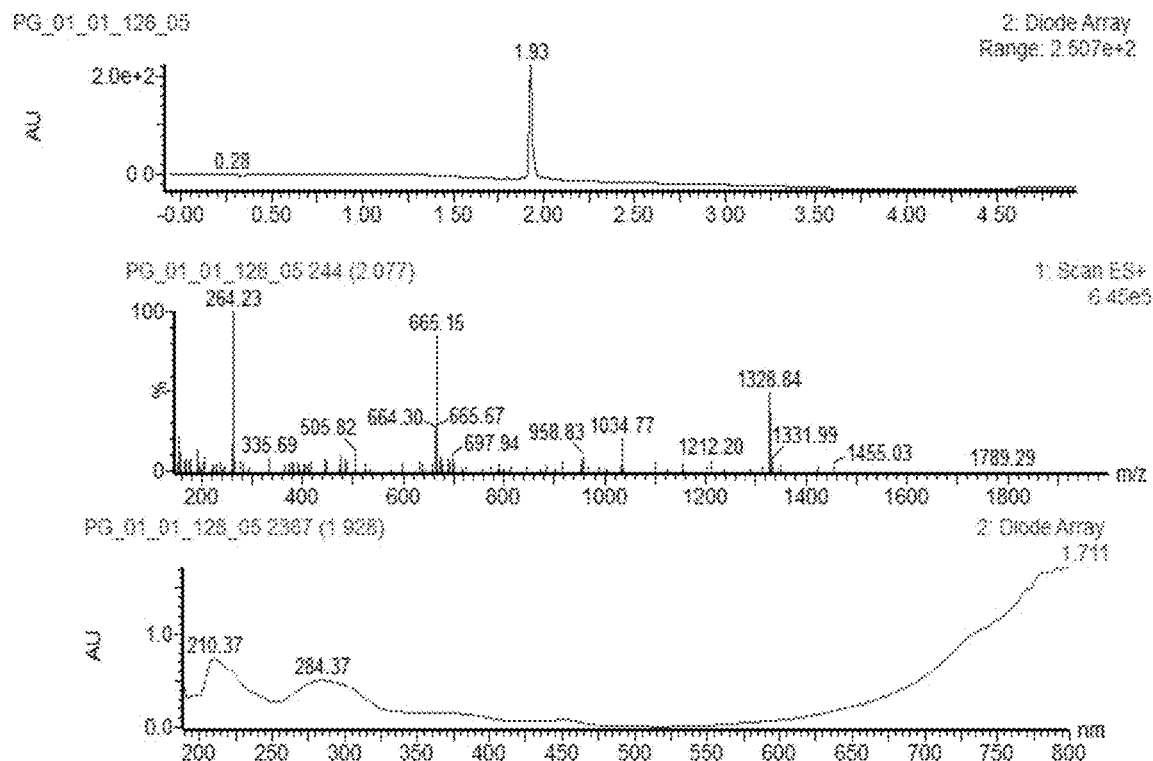
FIG. 12 Chromatogram profile of 118.
Figure 13:
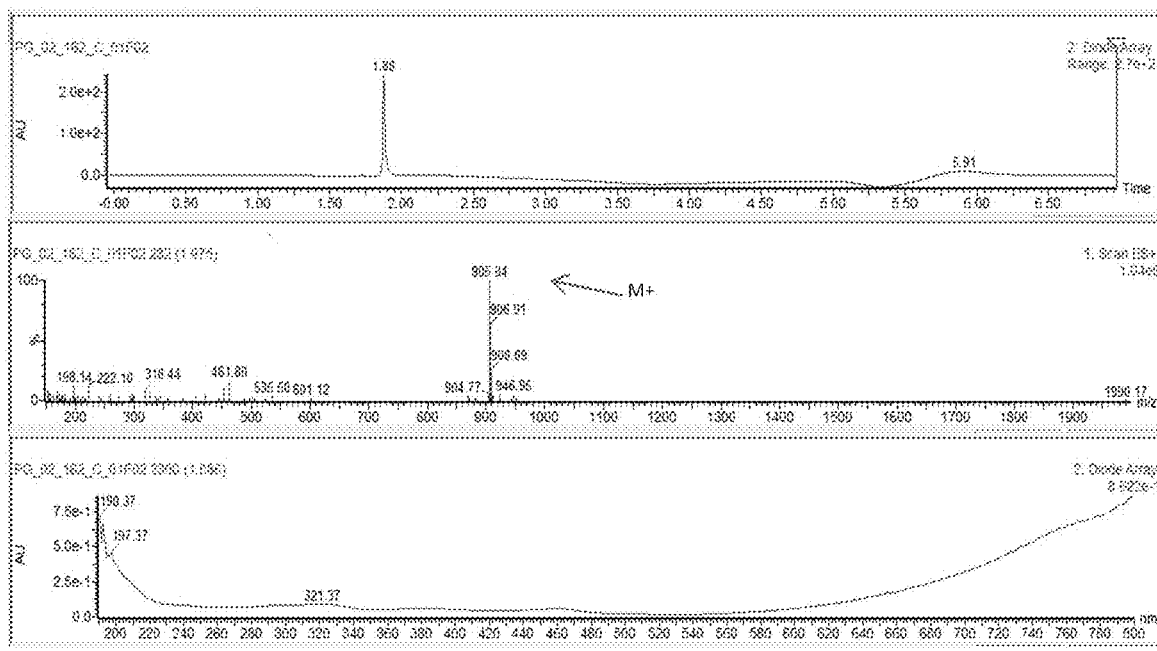
FIG. 13 Chromatogram profile of 120.
Figure 14:
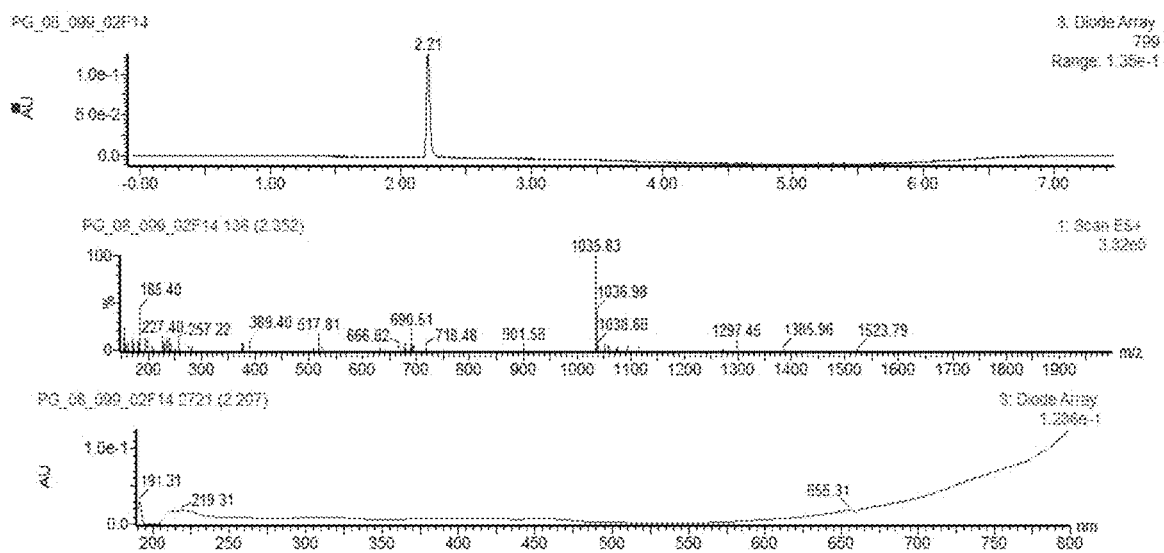
FIG. 14 Chromatogram profile of 122.
Figure 15:
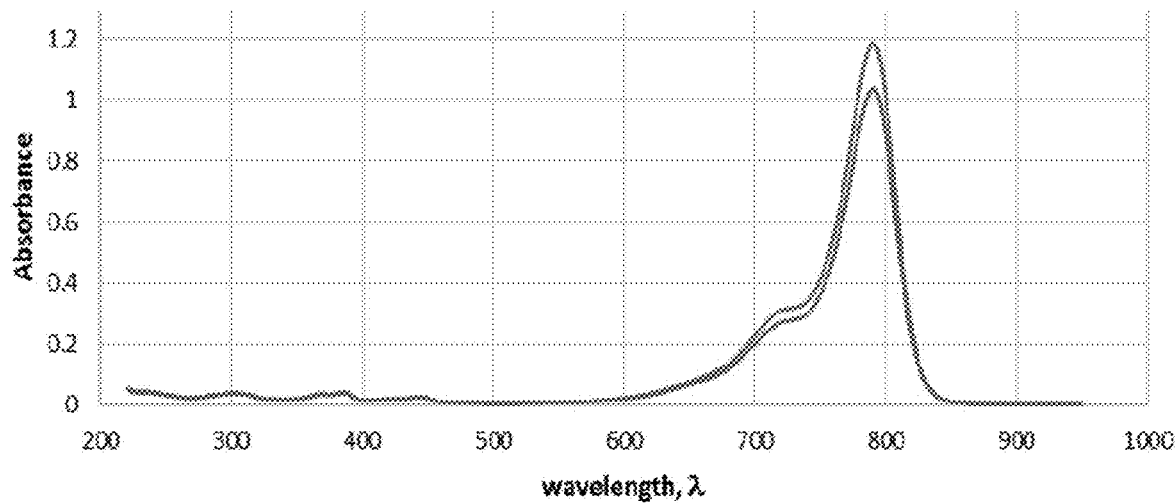
FIG. 15 Chromatogram profile of 125.
Figure 16:
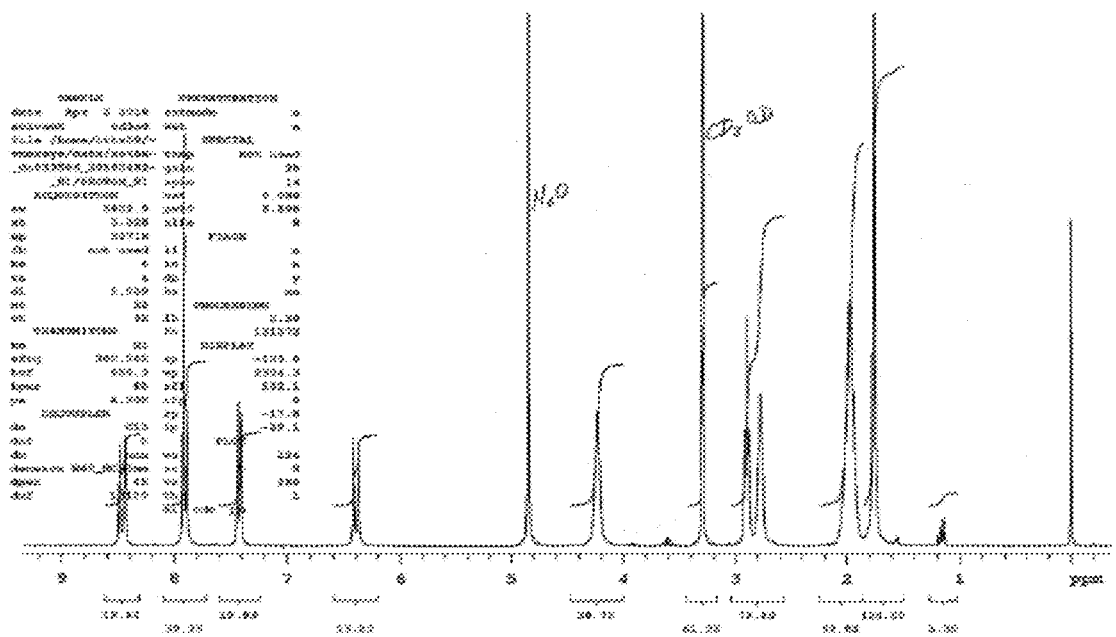
Figure 17:
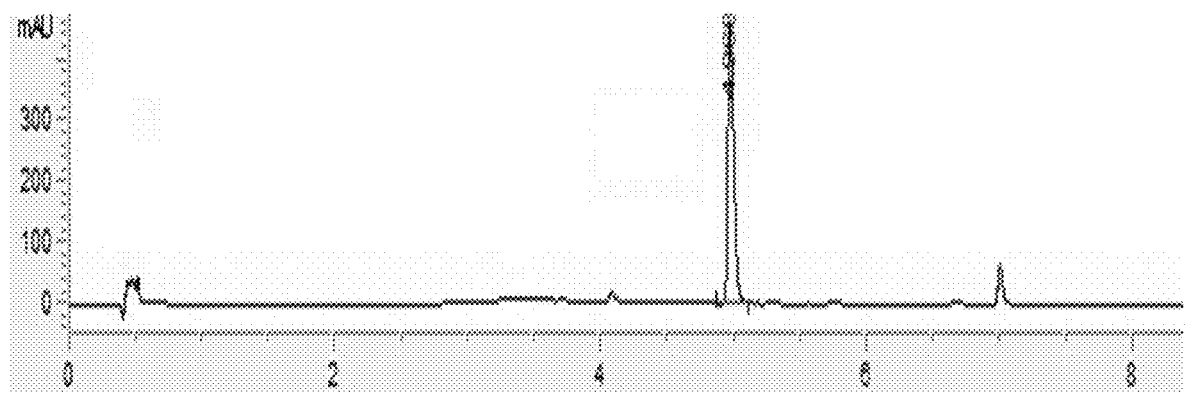
FIG. 17 Chromatogram profile of 126.
Figure 18:
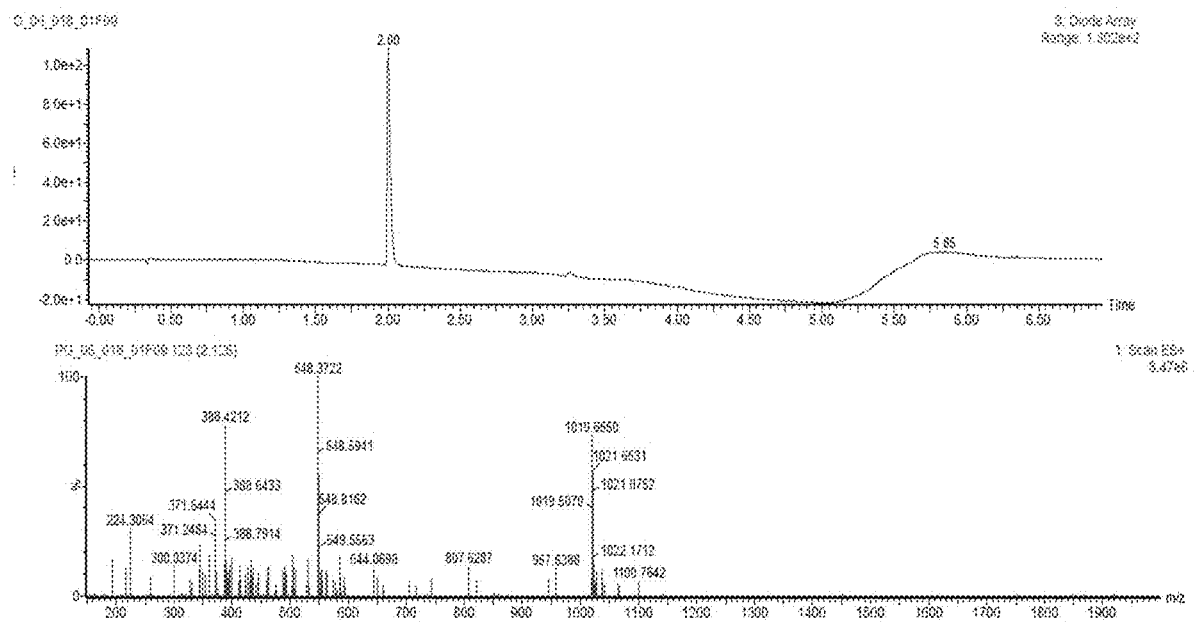
FIG. 18 Chromatogram profile of 127.
Figure 19:
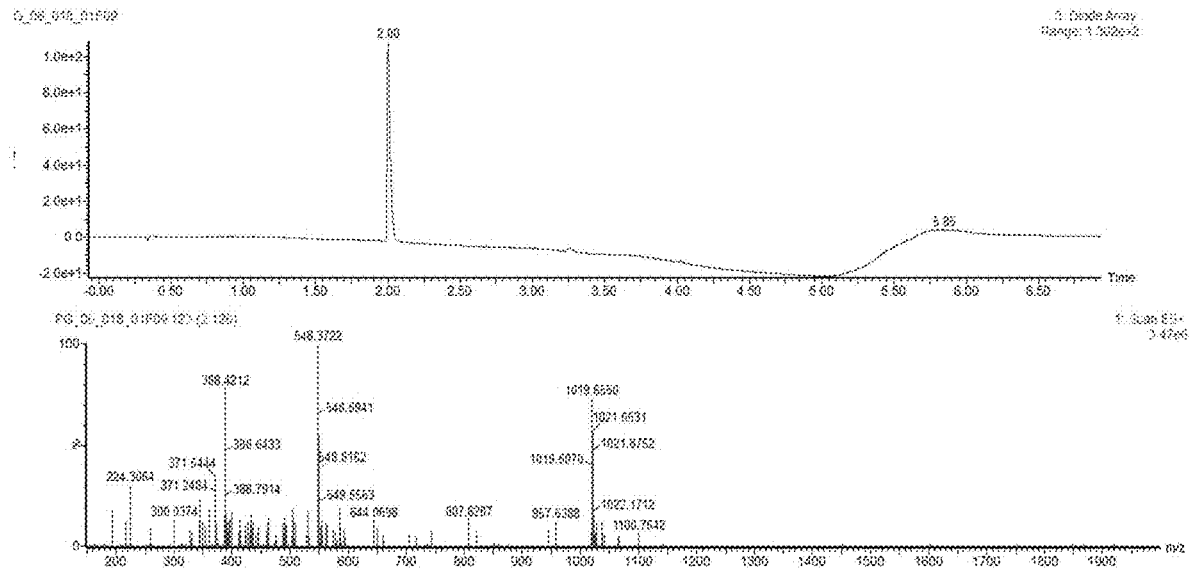
FIG. 19 Chromatogram profile of 128.
Figures 20, 21:
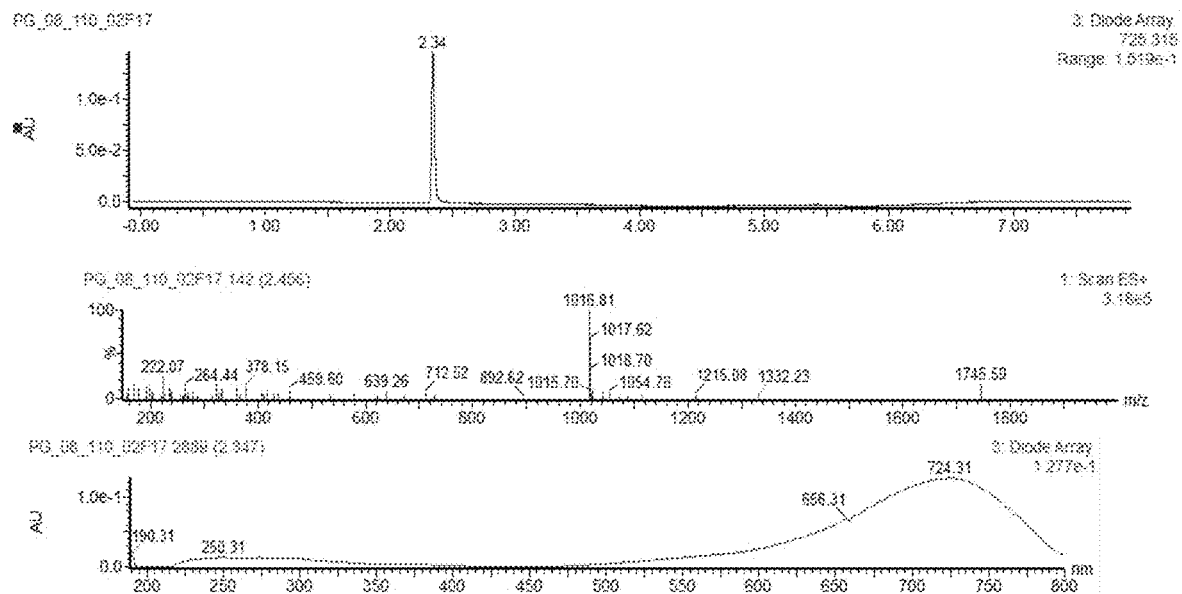
FIG. 20 Chromatogram profile of 129.
FIG. 21 Chromatogram profile of 130.
Figure 22:
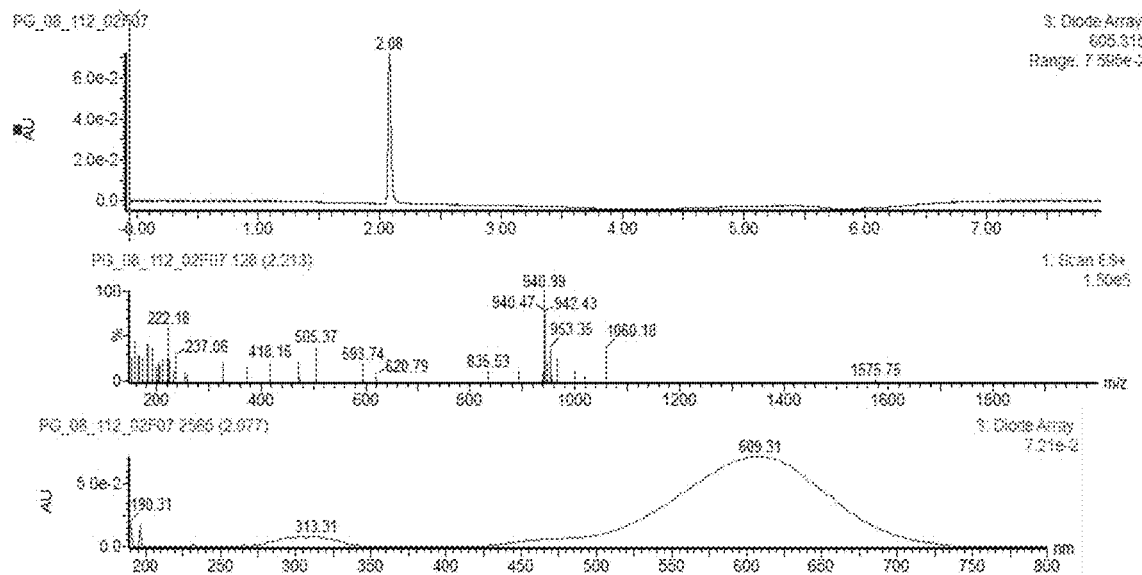
FIG. 22 Chromatogram profile of 131.
Figure 23:
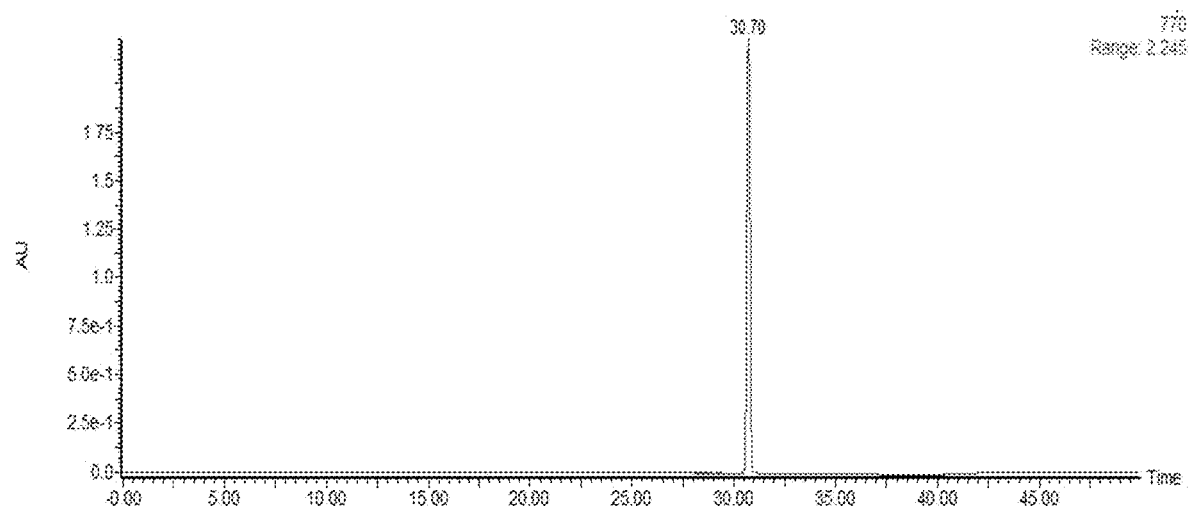
FIG. 23 Chromatogram profile of 132.
Figure 24:
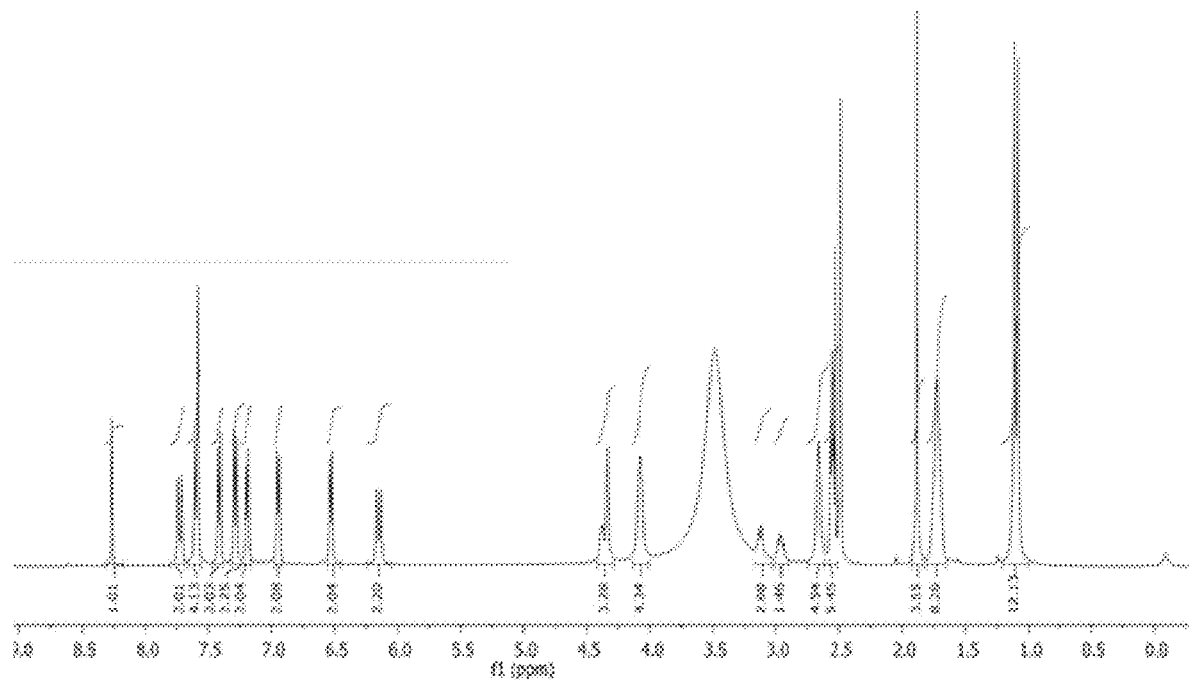
Figure 25:
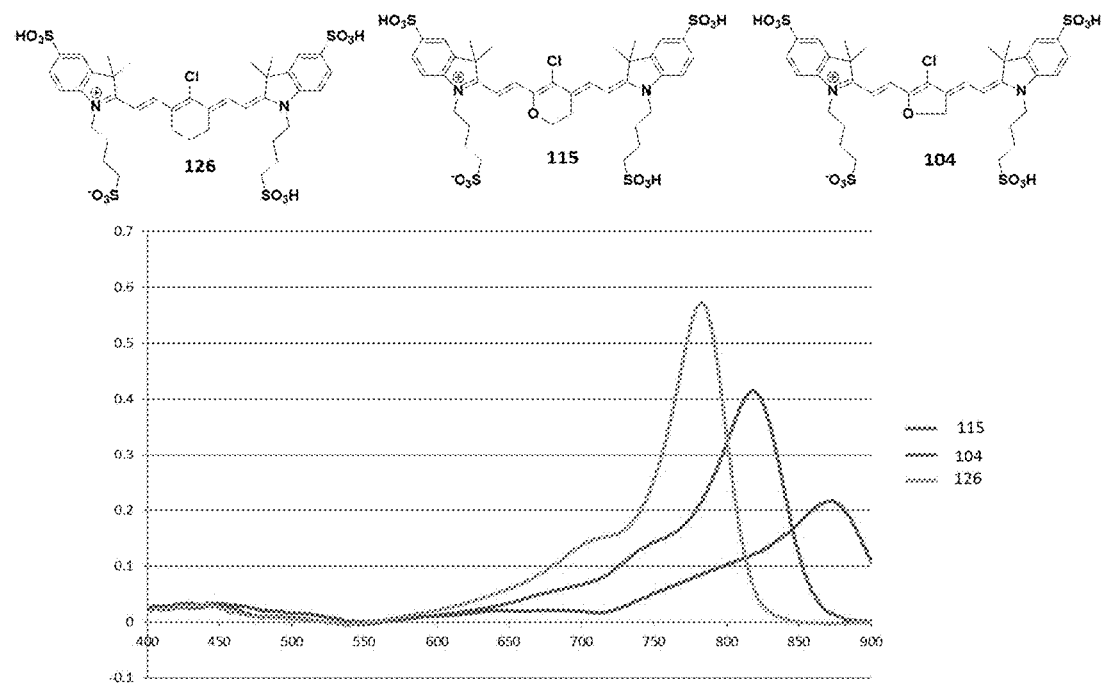
FIG. 25 illustrates the comparative analysis of absorption spectra of compounds 126, 115, and 104 demonstrating decreasing the ring size and increasing the number of electronegative atoms in the middle ring of the conjugated double bond system.
Figure 26:
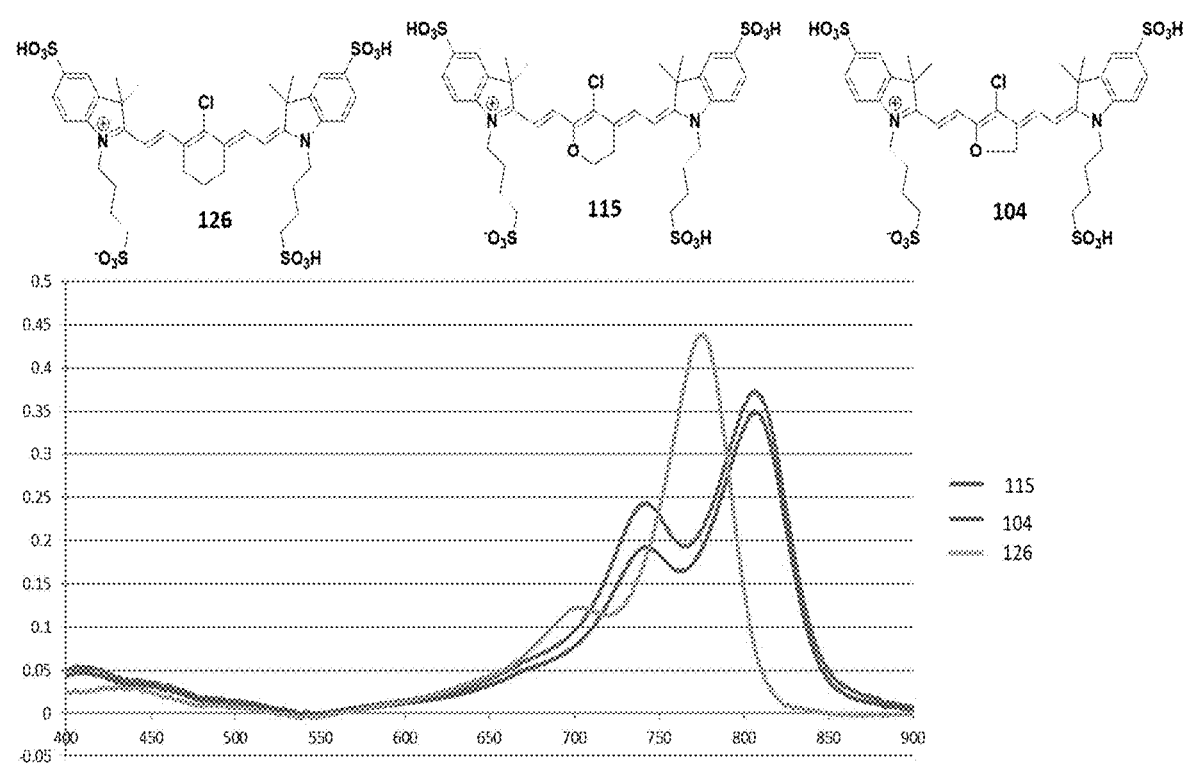
FIG. 26 illustrates the comparative analysis of absorption spectra of compounds 126, 115, and 104 demonstrating decreasing the ring size and increasing the number of electronegative atoms in the middle ring of the conjugated double bond system

FIG. 7 illustrates the absorption of compounds 2, 4, and 5 demonstrating decreasing the ring size and increasing the number of electronegative atoms in the middle ring of the conjugated double bond system. FIG. 8 illustrates the emission of compounds 2, 4, and 5 demonstrating decreasing the ring size and increasing the number of electronegative atoms in the middle ring of the conjugated double bond system.

What is claimed is:

1. A method for synthesizing a compound of formula (I)

Formula (I)

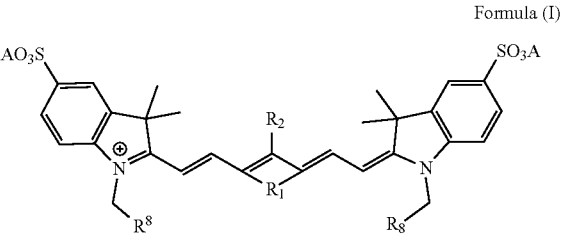

wherein:

$R_1$ is $(CH_2)_n$ and n is 1 or 3, $R_2$ is Br, I, or X—$R_3$, wherein X is $(CH_2)_m$, NH, O, S, or Se, m is 0, 1, 2, or 3, $R_3$ is $(CH_2)_pCH(R_4)COOH$ or $C_6H_4$—$(CH_2)_pCH(R_4)COOH$ or $(CH_2)_pCOOH$ or $(CH_2)_pNH_2$ and p is 0, 1, 2, or 3, $R_4$ is H or $NHR_5$, $R_5$ is H or alkyl group, $R_8$ is $(CH_2)_qSO_3H$ and q is 0, 1, 2, or 3, and A is sodium, calcium, magnesium, lithium, cholinate, lysinium, ammonium, or hydrogen comprising the steps of (a) reacting a compound of a formula

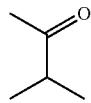

with a compound of a formula

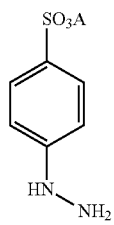

in the presence of an acetate salt to generate a compound of the formula

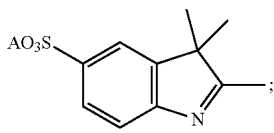

(b) reacting the resulting compound with a compound of the formula

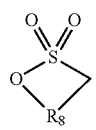

in the presence of 1,2-dichlorobenzene to generate a compound of the formula

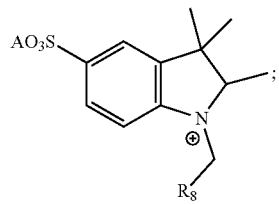

(c) reacting a compound of the formula

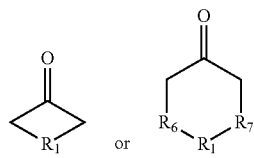

in the presence of an acetate salt, sultone, and 1,2-dichlorobenzene to generate a compound of the formula

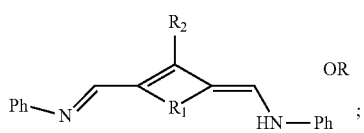

(d) reacting the compound of the formula

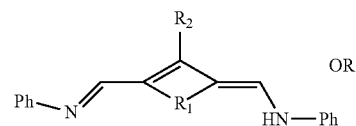

with a compound of the formula

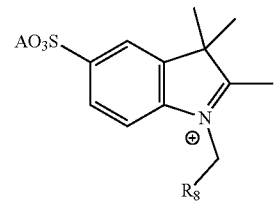

in the presence of an acetate salt to generate a compound of the formula

Formula (I)

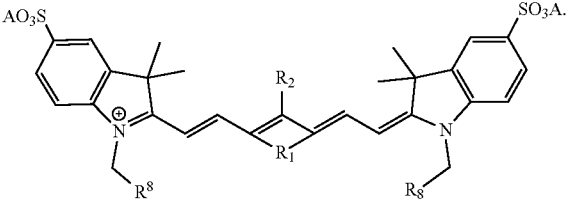

wherein the resulting compound is selected from the group consisting of:
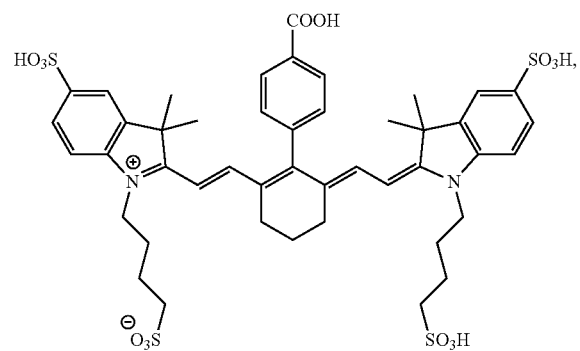
126
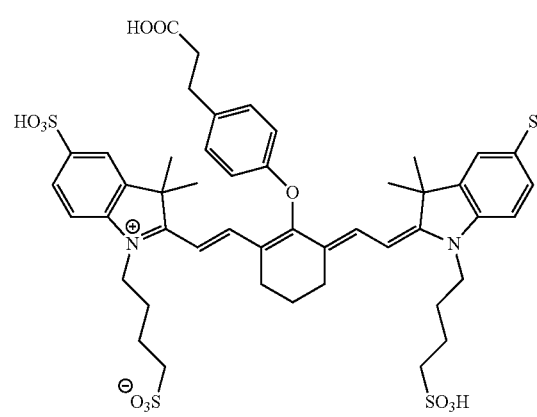
127
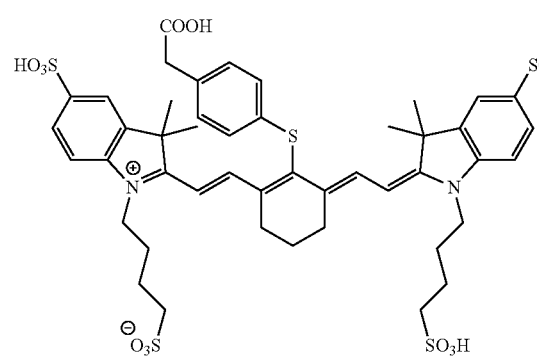
128
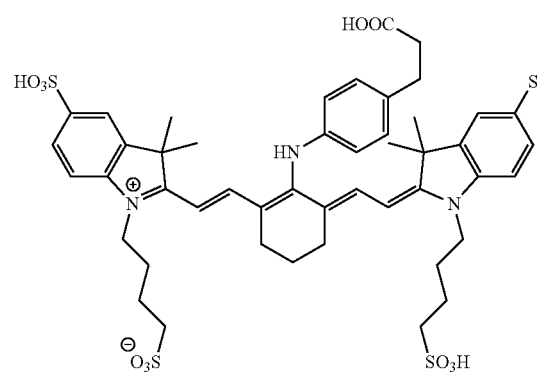
129
-continued
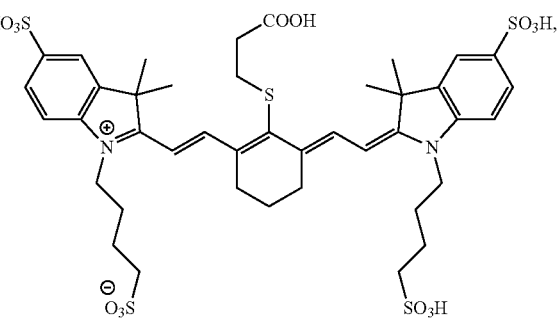
130
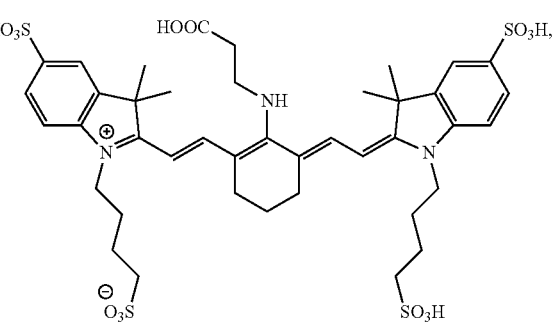
131
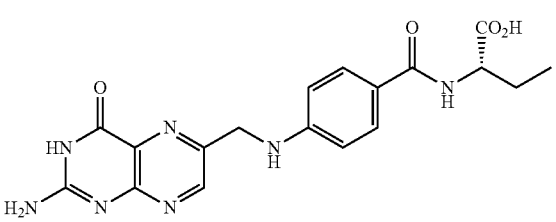
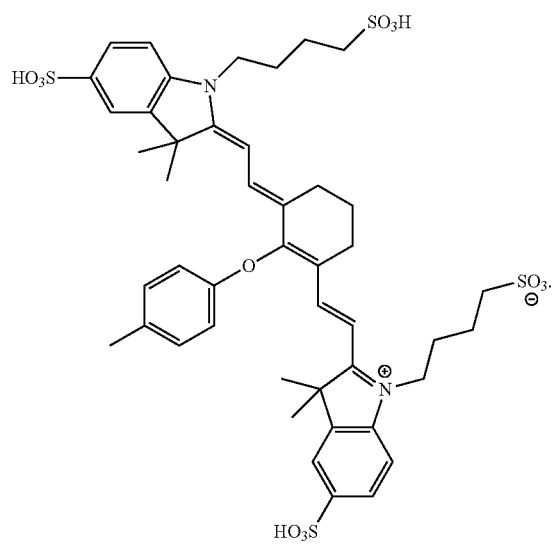

2. The method of claim 1, further comprising step (e) wherein the compound of the formula

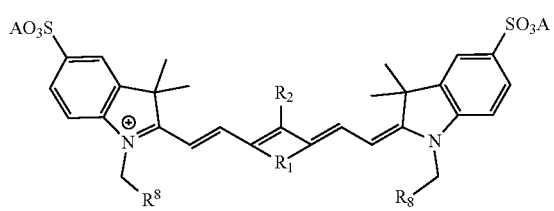

Formula (I)

is reacted with X—R in water, methanol, or DMSO, wherein X=OH, NH2, SH, or SeH to generate a compound of the formula

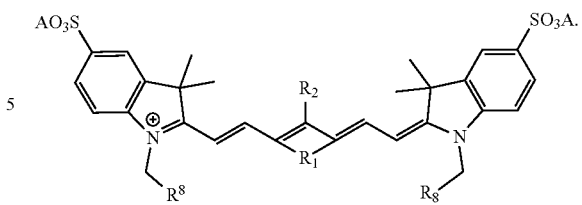

3. The method of claim 2, further comprising reacting the resulting compound of step (e) with a base and a compound of the formula Ligand-Linker-Z, wherein the Ligand-Linker comprises Pteroyl-Tyr-, Pteroyl-Lys-, —NH-Phenyl-CH$_2$—CH$_2$—, NH—CH$_2$—CH$_2$—, O-Phenyl-CH$_2$—CH$_2$, —O-Phenyl, S—CH$_2$—CH$_2$—, or chloro-dyes, and wherein Z is COOH, NH$_2$, OH, or SH.

4. The method of claim 1, wherein the resulting compound is precipitated in the presence of 1,2-dichlorobenzene or purified by chromatographic methods or crystallization method.

5. The method of claim 1, wherein the yield of the resulting compound in is at least 60%.

6. The method of claim 2, wherein the purity of the resulting compound in step (e) is at least 90%.

* * * * *

UNITED STATES PATENT AND TRADEMARK OFFICE
CERTIFICATE OF CORRECTION

Page 1 of 2

PATENT NO. : 11,964,965 B2
APPLICATION NO. : 16/879569
DATED : April 23, 2024
INVENTOR(S) : Sumith A. Kularatne and Pravin Gagare It is certified that error appears in the above-identified patent and that said Letters Patent is hereby corrected as shown below:

In the Specification

Column 16, Lines 55-64, reading:

"(b) reacting the resulting compound with a compound of the formula 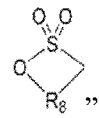 "
Should read: --- (b) reacting the resulting compound with a sultone ---

Column 37, Lines 58-65, reading:

"reacting the resulting compound with a compound of the formula 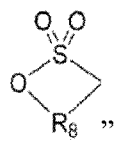 "
Should read: --- reacting the resulting compound with a sultone ---

In the Claims

Claim 1, Column 115, Lines 59-64, the structure reading:

" 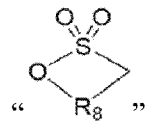 "

Should read: --- 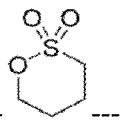 ---

Signed and Sealed this
Sixteenth Day of December, 2025

John A. Squires
*Director of the United States Patent and Trademark Office*

Claim 1, Column 116, Lines 21 and 22, reading:
"acetate salt, sultone, and 1,2-dichlorobenzene"
Should read: --- POCl3, DMF, and aniline ---